US011727086B2

(12) United States Patent
Tan et al.

(10) Patent No.: US 11,727,086 B2
(45) Date of Patent: Aug. 15, 2023

(54) MULTIMODALITY IMAGE PROCESSING TECHNIQUES FOR TRAINING IMAGE DATA GENERATION AND USAGE THEREOF FOR DEVELOPING MONO-MODALITY IMAGE INFERENCING MODELS

(71) Applicant: GE Precision Healthcare LLC, Milwaukee, WI (US)

(72) Inventors: Tao Tan, Eindhoven (NL); Gopal B. Avinash, San Ramon, CA (US); Máté Fejes, Szeged (HU); Ravi Soni, San Ramon, CA (US); Dániel Attila Szabó, Debrecen (HU); Rakesh Mullick, Bengaluru (IN); Vikram Melapudi, Bangalore (IN); Krishna Seetharam Shriram, Bengaluru (IN); Sohan Rashmi Ranjan, Bangalore (IN); Bipul Das, Chennai (IN); Utkarsh Agrawal, Bengaluru (IN); László Ruskó, Budapest (HU); Zita Herczeg, Szeged (HU); Barbara Darázs, Szeged (HU)

(73) Assignee: GE PRECISION HEALTHCARE LLC, Wauwatosa, WI (US)

( * ) Notice: Subject to any disclaimer, the term of this patent is extended or adjusted under 35 U.S.C. 154(b) by 289 days.

(21) Appl. No.: 17/093,960

(22) Filed: Nov. 10, 2020

(65) Prior Publication Data
US 2022/0101048 A1    Mar. 31, 2022

(30) Foreign Application Priority Data

Sep. 29, 2020  (IN) .............................. 202041042184

(51) Int. Cl.
*G06F 18/214*    (2023.01)
*G06T 7/30*    (2017.01)
(Continued)

(52) U.S. Cl.
CPC ............ *G06F 18/214* (2023.01); *A61B 5/055* (2013.01); *A61B 5/7267* (2013.01); *A61B 6/032* (2013.01);
(Continued)

(58) Field of Classification Search
CPC .... G06F 18/214; G06F 18/2178; G06F 18/22; G06F 18/28; G06N 3/045; G06N 5/04;
(Continued)

(56) References Cited

U.S. PATENT DOCUMENTS 8,781,197 B2     7/2014  Wang et al.
2017/0231713 A1*  8/2017  Siewerdsen ............ A61B 5/055
                                                          382/128

OTHER PUBLICATIONS

International Search Report and Written Opinion received for PCT Application Serial No. PCT/US2021/051337 dated May 9, 2022, 21 pages.

(Continued)

*Primary Examiner* — Manuchehr Rahmjoo
(74) *Attorney, Agent, or Firm* — Amin, Turocy & Watson, LLP

(57) ABSTRACT

Techniques are described for generating mono-modality training image data from multi-modality image data and using the mono-modality training image data to train and develop mono-modality image inferencing models. A method embodiment comprises generating, by a system comprising a processor, a synthetic 2D image from a 3D image of a first capture modality, wherein the synthetic 2D image corresponds to a 2D version of the 3D image in a second capture modality, and wherein the 3D image and the synthetic 2D image depict a same anatomical region of a same patient. The method further comprises transferring, by the system, ground truth data for the 3D image to the synthetic 2D image. In some embodiments, the method further comprises employing the synthetic 2D image to
(Continued)

facilitate transfer of the ground truth data to a native 2D image captured of the same anatomical region of the same patient using the second capture modality.

31 Claims, 30 Drawing Sheets

(51) Int. Cl.

| | |
|---|---|
| G06N 5/04 | (2023.01) |
| G16H 30/20 | (2018.01) |
| G16H 30/40 | (2018.01) |
| G16H 50/20 | (2018.01) |
| G16H 50/50 | (2018.01) |
| A61B 6/03 | (2006.01) |
| A61B 6/00 | (2006.01) |
| A61B 5/055 | (2006.01) |
| A61B 5/00 | (2006.01) |
| G06T 5/50 | (2006.01) |
| G06F 18/22 | (2023.01) |
| G06F 18/28 | (2023.01) |
| G06F 18/21 | (2023.01) |

(52) U.S. Cl.
CPC ........ *A61B 6/5223* (2013.01); *G06F 18/2178* (2023.01); *G06F 18/22* (2023.01); *G06F 18/28* (2023.01); *G06N 5/04* (2013.01); *G06T 5/50* (2013.01); *G06T 7/30* (2017.01); *G16H 30/20* (2018.01); *G16H 30/40* (2018.01); *G16H 50/20* (2018.01); *G16H 50/50* (2018.01); *G06T 2200/04* (2013.01); *G06T 2207/10081* (2013.01); *G06T 2207/10116* (2013.01); *G06T 2207/20081* (2013.01); *G06T 2207/20084* (2013.01); *G06T 2207/20212* (2013.01); *G06T 2207/30004* (2013.01); *G06V 2201/03* (2022.01)

(58) Field of Classification Search
CPC ............. G06V 10/7715; G06V 10/772; G06V 10/774; G06V 20/64; G06V 2201/03; G06T 15/10; G06T 2200/04; G06T 2207/10081; G06T 2207/10116; G06T 2207/20081; G06T 2207/20084; G06T 2207/20212; G06T 2207/30004; G06T 2210/41; G06T 5/50; G06T 7/30; G16H 30/20; G16H 30/40; G16H 50/20; G16H 50/50; G16H 50/70

See application file for complete search history.

(56) References Cited

OTHER PUBLICATIONS

Bier et al., "Learning to detect anatomical landmarks of the pelvis in X-rays from arbitrary views", International Journal of Computer Assisted Radiology and Surgery, vol. 14, No. 9, Apr. 20, 2019, pp. 1463-1473.

Van Houtte et al., "A Deep Learning Approach to Horse Bone Segmentation from Digitally Reconstructed Radiographs", 2019 Ninth International Conference on Image Processing Theory, Tools and Applications (IPTA), Nov. 6, 2019, pp. 1-6.

Ying, et al., "X2CT-GAN: Reconstructing CT from Biplanar X-Rays with Generative Adversarial Networks," arXiv:1905.06902v1 [eess.IV] May 16, 2019, 13 pages.

Palenstijn, et al., "The ASTRA tomography toolbox 2D tomography," Jul. 22, 2019, 38 pages.

Moturu, et al., "Creation of Synthetic X-Rays to Train a Neural Network to Detect Lung Cancer," Aug. 20, 2018, 16 pages.

Zhu, et al., "Unpaired Image-to-Image Translation using Cycle-Consistent Adversarial Networks," Oct. 22, 2017, In ICCV 2017, 9 pages.

radiologykey.com, "Imaging the Chest; The Chest Radiograph," Jul. 4, 2019, 34 pages.

mathworks.com, "How to convert/project a stack of CT images to a 2D X ray image," Jul. 27, 2018, 4 pages.

Toussie, et al., "Clinical and Chest Radiography Features Determine Patient Outcomes In Young and Middle Age Adults with COVID-19," May 14, 2020, 24 pages.

Teixeira, et al., "Generating Synthetic X-ray Images of a Person from the Surface Geometry," May 1, 2018, 9 pages.

Barbosa, et al., "Automated detection and quantification of COVID-19 airspace disease on chest radiographs: A novel approach achieving radiologist-level performance using a CNN trained on digital reconstructed radiographs (DRRs) from CT-based ground-truth," Aug. 13, 2020, 29 pages.

International Preliminary Report on Patentability received for PCT Application Serial No. PCT/US2021/051337 dated Apr. 13, 2023, 14 pages.

\* cited by examiner

1702 — Different SXRs Generated from the Same 3D Volume Using Different Projection Parameters 1704 — Corresponding Projected Masks Generated from the Same 3D Ground Truth Data Using the Different Projection Parameters

MULTIMODALITY IMAGE PROCESSING TECHNIQUES FOR TRAINING IMAGE DATA GENERATION AND USAGE THEREOF FOR DEVELOPING MONO-MODALITY IMAGE INFERENCING MODELS

CROSS REFERENCE TO RELATED APPLICATION

This application claims priority to India Patent Application Serial No. 202041042184 filed Sep. 29, 2020 and entitled "MULTIMODALITY IMAGE PROCESSING TECHNIQUES FOR TRAINING IMAGE DATA GENERATION AND USAGE THEREOF FOR DEVELOPING MONO-MODALITY IMAGE INFERENCING MODELS", the entirety of which is herein incorporated by reference.

TECHNICAL FIELD

This application relates to multimodality image processing techniques for training image data generation and usage thereof for developing mono-modality image inferencing models.

BACKGROUND

Machine learning (ML) models are used in many medical image processing and analysis tasks like organ segmentation, anomaly detection, diagnosis classification, risk prediction, temporal analysis, image reconstruction, and so on. However, one of the fundamental problems in data-driven based machine learning approaches is that the final model inferencing capability is limited by the scope of the training data used to develop the model. With respect to the medical imaging sector, it can be difficult to obtain enough medical images for model training that provide a comprehensive representation of a target medical condition across different patient populations.

SUMMARY

The following presents a summary to provide a basic understanding of one or more embodiments of the invention. This summary is not intended to identify key or critical elements or delineate any scope of the different embodiments or any scope of the claims. Its sole purpose is to present concepts in a simplified form as a prelude to the more detailed description that is presented later.

In one or more embodiments described herein, systems, computer-implemented methods, apparatus and/or computer program products are described that provide multimodality image processing techniques for training image data generation and usage thereof for developing mono-modality image inferencing models. Various embodiments of the disclosed subject matter are exemplified with respect to medical images and applications in the medical image processing domain. However, it should be appreciated that the disclosed techniques are not limited to the medical imaging domain and can be applied to facilitate generating and annotating training images for usage in training and developing various types of machine learning models in various domains.

According to an embodiment, a system is provided that comprises a memory that stores computer executable components, and a processor that executes the computer executable components stored in the memory. The computer executable components comprise a transformation component that generates a synthetic 2D image from a 3D image of a first capture modality, wherein the synthetic 2D image corresponds to a 2D version of the 3D image in a second capture modality, and wherein the 3D image and the synthetic 2D image depict a same anatomical region of a same patient. For example, in various implementations, the first capture modality can comprise a computed tomography (CT) modality and the second capture modality can comprise an X-ray (XR) modality. In accordance with this example, the synthetic 2D image can comprise a synthetic X-ray (SXR) and the 3D image can comprise a CT volume image (e.g., generated/computed based on a plurality of CT scan slices). The computer executable components further comprise an annotation transfer component that transfers ground truth data for the 3D image to the synthetic 2D image to generate an annotated synthetic 2D image with the ground truth data.

The computer executable components can further comprise a training module that employs the synthetic 2D image and the annotated synthetic 2D image to train one or more machine learning models to perform a medical inferencing task related to a medical condition reflected in the same anatomical region. In various embodiments, the training involves training at least one machine learning model to perform the medical inferencing task on 2D images as input as opposed to 3D images. The computer executable components can further comprise and inferencing module that applies the at least one machine learning model to the 2D images to generate inference outputs.

In some implementations, the transformation component can employ a trained 3D to 2D transformation model to generate the synthetic 2D image from the 3D image (e.g., generative adversarial network (GAN) or another type of generative machine learning model). Additionally, or alternatively, the transformation component can generate the synthetic 2D image using the 3D image and a projection process such as a parallel projection process and/or point source projection process. The projection process can also involve removing one or more objects from the 3D image that are excluded from 2D images captured using the second modality. In accordance with these embodiments, the 3D image can be or correspond to a 3D volume image and the ground truth data can comprise projected ground truth data. In some implementations of these embodiments, the computer executable components further comprise a pre-projection processing component that determines optimal projection parameters for the projection process based on segmentation of one or more 3D objects taken from the 3D volume image, and the transformation component performs the projection process using the optimal projection parameters. The pre-projection processing component can also refine the 3D volume image prior to projection processing to remove one or more objects from the 3D volume image that are typically not included in 2D images captured using the second modality. The projection component can also generate the projected ground truth data based using the projection process and the optimal projection parameters.

In various embodiments, the computer executable components can further comprise an enhancement component that enhances the synthetic 2D image as a post-processing step, resulting in an enhanced synthetic 2D image. With these embodiments, the annotation transfer component can further transfer the ground truth data for the 3D image to the enhanced synthetic 2D image to generate an enhanced annotated synthetic 2D image with the ground truth data. The training module can additionally or alternatively employ the enhanced synthetic 2D image and the enhanced annotated synthetic 2D image to train the one or more machine learning models.

In some implementations, the enhancement component can harmonize the synthetic 2D image with one or more reference images to generate the enhanced synthetic 2D image. Additionally, or alternatively, the enhancement component can harmonize the synthetic 2D image with a native 2D image to generate the enhanced synthetic 2D image, wherein the native 2D image comprises an image captured of the same anatomical region of the same patient using the second capture modality. Additionally, or alternatively, the enhancement component can apply a style translation model to the synthetic 2D image to generate the enhanced synthetic 2D image, wherein the style translation model comprises a neural network model configured to change an appearance of the synthetic 2D image to appear more similar to that of the a native 2D image captured of the same anatomical region using the second capture modality. Additionally, or alternatively, the enhancement component can register the synthetic 2D image with a native 2D image to generate the enhanced synthetic 2D image, wherein the native 2D image comprises an image captured of the same anatomical region of the same patient using the second capture modality.

In various embodiments, the annotation transfer component can also employ the synthetic 2D image to facilitate transfer of the ground truth data to a native 2D image captured of the same anatomical region of the same patient using the second capture modality to generate an annotated native 2D image. The training module can additionally, or alternatively, employ the native 2D image and the annotated native 2D image to train the one or more machine learning models. In some implementations of these embodiments, the computer executable components can further comprise an annotation component that presents the annotated native 2D image to one or more annotators for manual review and optional adjustment.

In one or more additional embodiments, the transformation component can comprise a projection component that projects the 3D image using different projection parameters to generate different synthetic 2D images respectively corresponding to 2D versions of the 3D image in the second capture modality, the different synthetic 2D images including the synthetic 2D image. In some implementations of these embodiments, the projection component can further generate transferred ground truth data for the different synthetic 2D images from ground truth data applied to the 3D image using the corresponding projection parameters used to generate different annotated synthetic 2D images. The training module can additionally or alternatively employ the different synthetic 2D images and the different annotated synthetic 2D images to train the machine learning model.

In other implementations of these embodiments, the computer executable components can further comprise a selection component that selects the synthetic 2D image from amongst the different synthetic 2D images based on a determination that, relative to other synthetic 2D images of the different synthetic 2D images, the synthetic 2D provides a closest match to a native 2D image captured of the same anatomical region of the same patient using the second capture modality. For example, the selection component can determine that the synthetic 2D image provides the closest match based on comparison of the native 2D image to the different synthetic 2D images using one or more similarity evaluation metrics. In accordance with these implementations, based on selection of the synthetic 2D image, the annotation transfer component can further transfer the ground truth data to the native 2D image using a subset of the different projection parameters used to generate the synthetic 2D image, resulting in generation of an annotated native 2D image. The training module can additionally or alternatively employ the native 2D image and the annotated native 2D image to train the one or more machine learning models.

The computer executable components can further comprise a registration component that registers the different synthetic 2D images with the native 2D image prior to the comparison to facilitate determining the closest match. This registration results in transformation of the different synthetic 2D images into registered synthetic 2D images. In some embodiments, the annotation transfer component can further transfer the ground truth data to the registered synthetic 2D image selected as the closest match using the subset of the different projection parameters used to generate synthetic 2D image, resulting in generation of an annotated registered synthetic 2D image. The training module can additionally or alternatively employ the registered synthetic 2D image and the annotated registered synthetic 2D image to train the one or more machine learning models.

In some embodiments, elements described in the disclosed systems can be embodied in different forms such as a computer-implemented method, a computer program product, or another form.

DETAILED DESCRIPTION

Figure 1:
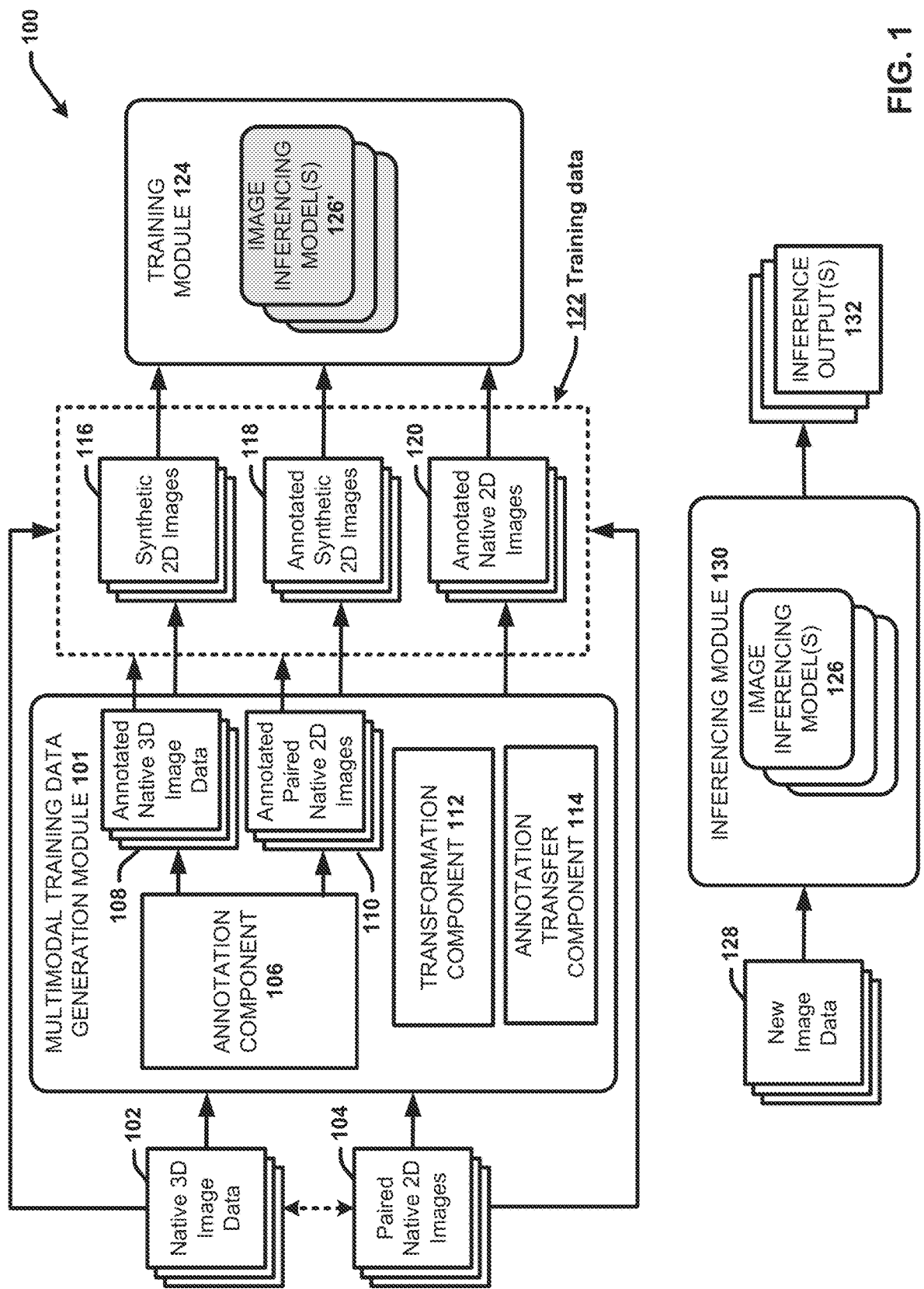
FIG. 1 illustrates a block diagram of an example, non-limiting multimodality image processing system for training image data generation and model development in accordance with one or more embodiments of the disclosed subject matter.

The following detailed description is merely illustrative and is not intended to limit embodiments and/or application or uses of embodiments. Furthermore, there is no intention to be bound by any expressed or implied information presented in the preceding Background section, Summary section or in the Detailed Description section.

The disclosed subject matter is directed to systems, computer-implemented methods, apparatus and/or computer program products that provide multimodality image processing techniques for training image data generation and usage thereof for developing mono-modality image inferencing models. In various embodiments, the mon-modality image inferencing models can include ML models configured to perform medical image processing tasks, such as disease classification/diagnosis, disease triaging, organ segmentation, anomaly detection, quantification, image reconstruction models, and the like. However, the disclosed techniques can also be extended to AI/ML image analysis/processing models configured to perform similar inferencing tasks on images in non-medical domains.

One or more embodiments of the disclosed subject matter are directed to techniques for generating corresponding synthetic 2D capture modality images for 3D modality images in scenarios in which the amount and/or diversity of native 2D capture modality images for model training is limited compared to the amount and/or diversity of 3D modality images. The synthetic 2D images can then be used to augment training datasets for model training and development. For example, since its initial outbreak in China between December 19 and March 2020, the novel coronavirus designated SARS-CoV-2 has caused an international and rapidly growing pandemic of respiratory illness termed COVID-19 (also referred to as coronavirus disease). Healthcare systems around the world have taken measure on all fronts to provide safe and effective treatment for COVID-19, including the development of medical imaging processing models that facilitate diagnosing and treating COVID-19 patients based on analysis of captured medical images of their respiratory systems. There is an increasing need for such models configured to process chest XR images, as XR provides the most efficient imaging modality for screening and diagnosing various lung diseases such as pneumonia. However, the majority of available of COVID-19 patient chest images for model training have been captured in China where CT imaging is more prevalent. Accordingly, the majority of available of COVID-19 patient chest images for model training include CT images.

With this example scenario in mind, the disclosed subject matter provides techniques for generating synthetic 2D images from a 3D image of a first capture modality, wherein the one or more synthetic 2D images correspond to 2D versions of the 3D image in a second capture modality. In various implementations, the first capture modality can comprise a CT modality and the second capture modality can comprise an XR modality. In this regard, the disclosed techniques can be applied to generate one or more SXR images that depict a medical condition manifested in an anatomical region of a patient from a CT image scan for the same patient that depicts the medical condition manifested in the anatomical region. For example, as applied to the COVID-19 scenario described above, the disclosed techniques can be used to generate synthetic COVID-19 chest XRs from a CT COVID-19 chest image captured for a patient.

In some embodiments, the disclosed techniques can employ projection processing of a 3D volume image to generate a corresponding synthetic 2D image. For example, the projection processing can include various known projection processing techniques such as point source projection processing and/or parallel projection processing. In this regard, as applied to generation of an SXR from a CT imaging study for an anatomical region of a patient, a CT volume image can be computed/generated from the individual CT scan slices. A synthetic 2D output image can be generated from the 3D volume image based on projection of the 3D volume image data onto a 2D projection plane using point source projection, parallel projection, or another image projection processing method. The resulting 2D output image corresponds to a 2D version of the 3D volume image. The disclosed techniques can further improve the quality and realistic appearance of the synthetic 2D output image using one or more pre-projection processing steps and/or one or more post-projection processing steps.

In various implementations, the one or more pre-processing steps can include estimating the optimal projection parameters for generating the 2D image from the 3D volume image. In some embodiments, the optimal projection parameters can be determined based on segmentation processing of the 3D volume and/or one or more 3D images used to generate the 3D volume. In another embodiment, the optimal projection parameters can be determined based on comparative analysis of different synthetic 2D images generated from the same 3D volume image using different projection parameters. In some implementations of these embodiments in which a native 2D image corresponding to the 3D volume image is available, the different synthetic 2D images can be compared to the native 2D image and evaluated using one or more similarity metrics to identify the best matching synthetic 2D image. With these embodiments, the parameters used to generate the best matching synthetic 2D image can be used as the optimal projection parameters. Other techniques for estimating the optimal projection parameters are also provided.

The one or more pre-projection processing techniques can also include performing object removal processing of the 3D volume image to refine the 3D volume image to remove objects and/or image features that interfere with the quality of the output image and/or that are not desired in the output image. For example, the object removal process can involve removing objects in the 3D image data that are typically not present in 2D images captured in the desired 2D capture modality for the 2D output image. In this regard, as applied to generating synthetic medical images depicting a target anatomical region of interest, the object removal process can involve removing non-body parts included in the 3D image data (e.g., the imaging table or the like), removing anatomical features/parts outside the region of interest, and the like.

The one or more post-processing steps can involve processing the initial 2D output image to enhance the quality of the synthetic 2D image and/or to make the synthetic 2D image appear more realistic relative to a desired native 2D capture modality (e.g., to appear more like a real XR image in implementations in which the desired native 2D capture modality is XR). Some post-processing techniques for 2D synthetic image enhancement can include, but are not limited to, image harmonization processing using one or more reference images, image style transfer processing using one or more pretrained style transfer models, and/or image registration processing in implementations in which a native 2D image corresponding to the 3D volume image is available). The one or more post-processing steps can also include adapting the appearance of the synthetic 2D image (and/or the enhanced synthetic 2D image) to generate different versions of the synthetic 2D image to reflect variations that appear in the field. For example, as applied to medical images, in some embodiments, different versions of the synthetic 2D image can be generated with different appearance variations for different patient populations, different acquisition protocols, and the like.

One or more embodiments of the disclosed subject matter further provide techniques for transferring ground truth data from 3D modality images to 2D modality images, including synthetic 2D modality images and native 2D modality images paired with the 3D modality images. In some implementations of these embodiments, this ground truth transfer can be facilitated using paired 3D image data captured using a 3D capture modality and native 2D image data captured using a 2D capture modality of the same object or environment in a same or similar state. The 3D and 2D images can be considered paired because they both depict the same object or environment in a same or similar state. In this regard, an ideal pair of native 3D modality image data and native 2D modality image data would include image data respectively captured using the different capture modalities of the same object/environment at the same time and from the same viewpoint.

For example, as applied to medical image processing, in some implementations the paired 3D and 2D images can include a CT image study (e.g., including one or more CT scan slices) for an anatomical region of a patient and an XR image of the same anatomical region of the same patient. In embodiments in which the disclosed techniques are used to generate training image data for training an inferencing model to perform a medical inferencing task related to a medical condition reflected in the same anatomical region, both the native 3D image data and the native 2D image data correspond to images acquired of the anatomical region with a similar state of at least one medical condition of the patient. In other words, both the native 3D image data and the native 2D image data should depict the same medical condition/disease of the patient in a same or similar state. For fast moving medical diseases/conditions such as respiratory disease/pneumonia in patients with COVID-19, the closer in time the respective 3D image data and 2D image data are captured from the patient the better (e.g., preferably less than 48 hours and more preferably less than 24 hours).

In one or more implementations in which paired 3D image data and 2D image data is available, the 3D image data include previously annotated 3D image data with the ground truth marked thereon and/or otherwise associated therewith. Additionally, or alternatively, the 3D image data can be presented to one or more annotators for manual application of the ground truth data. The 3D image data can further be projected using different projection parameters to generate different candidate synthetic 2D images. One or more of the pre-projection processing techniques can also be applied in association with generating the candidate synthetic 2D images. The different candidate synthetic 2D images can be compared to the native 2D image and evaluated using one or more similarity metrics to identify the best matching synthetic 2D image. The projection parameters used to generate the best matching synthetic 2D image can then be used to transfer the ground truth data associated with the 3D image data to the native 2D image and/or the best matching synthetic 2D image.

For example, in one implementation as applied to classifying disease regions in medical images, the 3D image data can comprise 3D volume image data with the disease region marked thereon. In accordance with this example, the disease region as marked in the 3D image data can be projected onto a 2D projection plane using the projection parameters of the best matching synthetic 2D image to generate projected 2D ground truth data. The projected 2D ground truth data can further be transferred to the native 2D image and/or the best matching synthetic 2D image. The best matching synthetic 2D image (with and without ground truth transfer data) can also be enhanced and/or augmented using one or more of the various post-processing techniques describe herein. This process can further be repeated for additional pairs of 3D/2D image data to generate high quality annotated 2D modality training data.

In one or more embodiments, the synthetic 2D images with and without transferred ground truth data, the native 2D images with and without transferred ground truth data, and the 3D image data can further be used to train and develop mono-modality and multimodality image inferencing models to perform various tasks.

The term "image inferencing model" is used herein to refer to an AI/ML model configured to perform an image processing or analysis task on images. The image processing or analysis task can vary. In various embodiments, the image processing or analysis task can include, (but is not limited to): a segmentation task, an image reconstruction task, an object recognition task, a motion detection task, a video tracking task, an optical flow task, and the like. The image inferencing models described herein can include 2D image processing models as well as 3D image processing models. The image processing model can employ various types of AI/ML algorithms, including (but not limited to): deep learning models, neural network models, deep neural network models (DNNs), convolutional neural network models (CNNs), generative adversarial neural network models (GANs) and the like. The terms "image inferencing model," "image processing model," "image analysis model," and the like are used herein interchangeably unless context warrants particular distinction amongst the terms.

The term "image-based inference output" is used herein to refer to the determination or prediction that an image processing model is configured to generate. For example, the image-based inference output can include a segmentation mask, a reconstructed image, an adapted image, an annotated image, a classification, a value, or the like. The image-based inference output will vary based on the type of the model and the particular task that the model is configured to perform. The image-based inference output can include a data object that can be rendered (e.g., a visual data object), stored, used as input for another processing task, or the like. The terms "image-based inference output", "inference output" "inference result" "inference", "output", "predication", and the like, are used herein interchangeably unless context warrants particular distinction amongst the terms.

As used herein, a "medical imaging inferencing model" refers to an image inferencing model that is tailored to perform an image processing/analysis task on one or more medical images. For example, the medical imaging processing/analysis task can include (but is not limited to): disease/condition classification, disease region segmentation, organ segmentation, disease quantification, disease/condition staging, risk prediction, temporal analysis, anomaly detection, anatomical feature characterization, medical image reconstruction, and the like. The terms "medical image inferencing model," "medical image processing model," "medical image analysis model," and the like are used herein interchangeably unless context warrants particular distinction amongst the terms.

The types of medical images processed/analyzed by the medical image inferencing models described herein can include images captured using various types of image capture modalities. For example, the medical images can include (but are not limited to): radiation therapy (RT) images, X-ray (XR) images, digital radiography (DX) X-ray images, X-ray angiography (XA) images, panoramic X-ray (PX) images, computerized tomography (CT) images, mammography (MG) images (including a tomosynthesis device), a magnetic resonance imaging (MRI) images, ultrasound (US) images, color flow doppler (CD) images, position emission tomography (PET) images, single-photon emissions computed tomography (SPECT) images, nuclear medicine (NM) images, and the like. The medical images can also include synthetic versions of native medical images such as synthetic X-ray (SXR) images, modified or enhanced versions of native medical images, augmented versions of native medical images, and the like generated using one or more image processing techniques. The medical imaging processing models disclosed herein can also be configured to process 3D images.

A "capture modality" as used herein refers to the specific technical mode in which an image or image data is captured using one or more machines or devices. In this regard, as applied to medical imaging, different capture modalities can include but are not limited to: a 2D capture modality, a 3D capture modality, an RT capture modality, a XR capture modality, a DX capture modality, a XA capture modality, a PX capture modality a CT, a MG capture modality, a MRI capture modality, a US capture modality, a CD capture modality, a PET capture modality, a SPECT capture modality, a NM capture modality, and the like.

The term "target capture modality," is used herein to refer to the specific capture modality for which training image data is desired. In accordance with various embodiments, the target capture modality can refer to the modality in which an image in a first modality is transformed into using the techniques disclosed herein. In this context, the first modality is referred to herein as the "source capture modality." The terms "target capture modality," "target modality," "target image capture modality," and the like are employed interchangeably throughout, unless context warrants particular distinctions among the terms. The terms "source capture modality," "source modality," "source image capture modality," and the like are employed interchangeably throughout, unless context warrants particular distinctions among the terms.

In this regard, reference to a "target image" as used herein refers to an image that was captured using the target capture modality or a realistic synthetic image that appears as if it was captured using the target capture modality. Similarly, reference to a "source image" as used herein refers to an image that was captured using the source capture modality or a realistic synthetic image that appears as if it was captured using the source capture modality. The terms "target image," "target domain image," "image in the target modality," "image of the target modality," and the like are employed interchangeably throughout, unless context warrants particular distinctions among the terms. The terms "source image," "source domain image," "image in the source modality," "image of the source modality," and the like are employed interchangeably throughout, unless context warrants particular distinctions among the terms.

As used herein, a "3D image" refers to digital image data representing an object, space, scene, and the like in three dimensions, which may or may not be displayed on an interface. 3D images described herein can include data representing positions, geometric shapes, curved surfaces, and the like. In an aspect, a computing device, such as a graphic processing unit (GPU) can generate a 3D image based on the data, performable/viewable content in three dimensions. For example, a 3D image can include a collection of points represented by 3D coordinates, such as points in a 3D Euclidean space (e.g., a point cloud). The collection of points can be associated with each other (e.g. connected) by geometric entities. For example, a mesh comprising a series of triangles, lines, curved surfaces (e.g. non-uniform rational basis splines ("NURBS")), quads, n-grams, or other geometric shapes can connect the collection of points. In an aspect, portions of the mesh can include image data describing texture, color, intensity, and the like.

In various embodiments, captured 2D images (or portions thereof) can be associated with portions of the mesh. A 3D image can thus be generated based on 2D image data, 2D sensory data, sensory data in combination with raw 2D data, 3D spatial data (e.g. spatial depth and distance information), computer generated positional data, and the like. In an aspect, data used to generate 3D images can be collected from scans (e.g. utilizing sensors) of real-world scenes, spaces (e.g. houses, office spaces, outdoor spaces, etc.), objects (e.g. furniture, decorations, goods, etc.), anatomical regions of the body, and the like. Data can also be generated based on computer implemented 3D modeling systems. In some embodiments, a 3D image can be or include a 3D volume image that provides a 3D representation or model of an object or environment generated from a plurality of 2D images captured along different planes. For example, a CT volume image can be or correspond to a 3D representation of an anatomical region of a patient generated/computed from a series of CT scan slices captured along different planes. In this regard, as applied to medical imaging, a 3D image can be or include a 3D volume image of anatomical region of a patient.

In this regard, a 3D medical image refers to a 3D representation of an anatomical region of a patient. In some implementations, a 3D medical image can be captured in 3D directly by the acquisition device and protocol. In other implementations, a 3D medical image can comprise a generated image that was generated from 2D and/or 3D image data captured of the anatomical region of the patient. Some example 3D medical images include 3D volume images generated from CT image data, MRI image data, and US image data.

It is noted that the terms "3D image," "3D volume image," "volume image," "3D model," "3D object,", "3D reconstruction," "3D representation," "3D rendering," and the like are employed interchangeably throughout, unless context warrants particular distinctions among the terms. It should be appreciated that such terms can refer to data representing an object, an anatomical region of the body, a space, a scene, and the like in three dimensions, which may or may not be displayed on an interface. The terms "3D data," can refer to data utilized to generate a 3D image, data describing a 3D image, data describing perspectives or points of view of a 3D image, capture data (e.g. sensory data, images, etc.), meta-data associated with a 3D image, and the like. It is noted that the term a "2D image" as used herein can refer to data representing an object, an anatomical region of the body, a space, a scene, and the like in two dimensions, which may or may not be displayed on an interface.

The term "native" image is used herein to refer to an image in its original capture form and/or its received form prior to processing by the disclosed systems. In this regard, a native 3D image refers to a 3D image in its received state prior to pre-projection processing, transformation processing, projection processing, and post-projection/transformation processing. For example, a native 3D image can include a received 3D volume image, such a s CT volume image. The term "synthetic" image is used herein to distinguish from native images and refers to an image generated or derived from a native image using one or more transformation processing techniques disclosed herein. In various embodiments, a synthetic image refers to a second modality image generated and/or derived from a first modality image. For example, in some embodiments, the second modality image comprises a 2D modality image (e.g., an XR modality) and the first modality image comprises a 3D modality image (e.g., a CT modality).

One or more embodiments are now described with reference to the drawings, wherein like referenced numerals are used to refer to like elements throughout. In the following description, for purposes of explanation, numerous specific details are set forth in order to provide a more thorough understanding of the one or more embodiments. It is evident, however, in various cases, that the one or more embodiments can be practiced without these specific details.

Turning now to the drawings, FIG. 1 illustrates a block diagram of an example, non-limiting multimodality image processing system for training image data generation and model development in accordance with one or more embodiments of the disclosed subject matter. Embodiments of systems described herein can include one or more machine-executable components embodied within one or more machines (e.g., embodied in one or more computer-readable storage media associated with one or more machines). Such components, when executed by the one or more machines (e.g., processors, computers, computing devices, virtual machines, etc.) can cause the one or more machines to perform the operations described.

For example, multimodality image processing system 100 includes multimodal training data generation module 101, training module 124 and inferencing module 130 which can respectively be and include computer/machine executable components. These computer/machine executable components (and other described herein) can be stored in memory (not shown) associated with the one or more machines (not shown). The memory can further be operatively coupled to at least one processor (not shown), such that the components (e.g., the multimodal training data generation module 101, the training module 124, the inferencing module 130, and other components described herein), can be executed by the at least one processor to perform the operations described. Examples of said and memory and processor as well as other suitable computer or computing-based elements, can be found with reference to FIG. 26, and can be used in connection with implementing one or more of the systems or components shown and described in connection with FIG. 1 or other figures disclosed herein.

The deployment architecture of multimodality image processing system 100 can vary. For example, in some embodiments, the multimodal training data generation module 101 (and/or one or more components associated therewith), the training module 124, and the inferencing module 130 can be deployed at different computing devices/machines in a distributed computing environment and communicatively coupled via one or more networks (e.g., a wide area network (WAN), a local area network (LAN), or the like). In other embodiments, the respective modules can be deployed at a same computing device in a local deployment architecture. Various alternative deployment architecture variations can also be used.

The multimodal training data generation module 101 can provide various multimodality image processing functionalities to generate high quality training data 122 that can be used by the training module 124 to train and develop one or more image inferencing models 126'. As described in greater detail below, these multimodality image processing functionalities can include generating and/or annotating training data images of a target capture modality (e.g., a 2D capture modality) from image data captured and/or generated using a different source capture modality (e.g., a 3D capture modality).

Once trained, the inferencing module 130 can apply the one or more image inferencing models 126 to new image data 128 in the field to generate one or more inference outputs 130 for corresponding use cases and applications. In the embodiment shown, the image inferencing models 126' associated with the training module 124 are distinguished from the image inferencing models 126 associated with the inferencing module 130 to indicate their respective development status. In this regard, the image inferencing models 126' associated with the training module 124 are shown in grey to indicate they under training and development, while the image inferencing models 126 associated with the inferencing module 130 are shown in white to indicate they have completed training and are ready for deployment in the field. In this regard, it should be appreciated that the image inferencing models 126' and the image inferencing models 126 are the same models.

The type of the one or more image inferencing models 126' can vary. In some embodiments, the one or more image inferencing models 126' can be or include one or more medical image inferencing models configured to perform one or more medical inferencing tasks related to a medical condition reflected in one or more medical images. In some implementations, the medical inferencing tasks can include tasks related to triage, such as classification of the medical condition, segmentation of a disease region associated with the medical condition, segmentation of an organ associated with the medical condition or the like. For instance, as applied to triage of COVID-19 disease based on chest XR images, the one or more image inferencing models 126' can include a model for classifying XR images with and without the disease, a model for segmenting the COVID-19 disease region to facilitate further inspection by radiologists, a model for segmenting the entire lung even in the presence of lung consolidation and other abnormalities, and the like.

The medical inferencing tasks can include tasks related to disease quantification, staging and risk prediction. For example, in some implementations, the one or more image inferencing models 126' can include a model for computing biomarker metrics such as disease region/total lung region expressed as a ratio in XR images. In another example, the one or more image inferencing models 126' can include a model that uses volumetric measures in paired CT and XR image data to build a regression model in XR to obtain volumetric measurements from chest XR images. In another example, the one or more image inferencing models 126' can include a model that determines whether a patient needs a ventilator or not based on chest XR data using regression analysis when outcomes data is available in addition to the image data for training. In another example, the one or more image inferencing models 126' can include a model configured to perform temporal analysis and monitor changes in the disease region over time.

It should be appreciated that the different medical image ML models described above are merely exemplary and not intended to limit the scope of the disclosed subject matter. Furthermore, the one or more image inferencing models 126' can additionally or alternatively include AI/ML image analysis/processing model configured to process images in non-medical domains.

In accordance with various embodiments of the disclosed subject matter, the multimodal training data generation module 101 (and other multimodal training data generation modules described herein) provides multimodality image processing techniques for generating mono-modality training image data that can be used for developing mono-modality image inferencing models. Thus, in various embodiments, the one or more image inferencing models 126' can include at least one model that is designed/trained to receive and process mono-modality image data as input as opposed to multi-modality image data. The one or more image inferencing models 126' can also include at least one model trained to receive and process 2D image data of a specific target capture modality (e.g., XR or another 2D image capture modality), wherein the training image data used to train and develop the model was generated by the multimodal training data generation modules 101 from images of a 3D modality. In this regard, at least one of the one or more image inferencing models 126' can be designed/trained to receive and process 2D image data as input as opposed to 3D image data.

Additionally, or alternatively, the one or more image inferencing models 126' can be trained to receive and process a combination of 2D image data and 3D image data as input. this regard, the type of the new image data 128 can vary depending on the target domain of the one or more image inferencing models 126 and the type of image data available training data 122.

In accordance with various embodiments of the disclosed subject matter, the target domain of at least some of the one or more image inferencing models 126 includes 2D images of a specific 2D target capture modality. With these embodiments, the new image data 128 can be or correspond to new native 2D images captured using the target capture modality. For example, as applied to the COVID-19 example uses cases describe above, the target domain can include XR images as opposed to CT images. In this example, the new image data 128 can be or correspond to new native XR images.

With these embodiments, the multimodal training data generation module 101 can facilitate generating and annotating high quality 2D images in the target 2D capture modality for addition to the training data 122. For example, in the embodiment shown, the training data 122 can include synthetic 2D images 116, annotated synthetic 2D images 118, and annotated native 2D images 120. The synthetic 2D images 116, the annotated synthetic 2D images 118, and the annotated native 2D images 120 can respectively be or correspond to images captured using the target 2D capture modality. For example, in implementations in which the target 2D capture modality is an XR modality, the synthetic 2D images 116 can comprise SXR images, the annotated synthetic 2D images 118 can comprise annotated SXR images, and the annotated native 2D images can comprise native annotated XR images. The training module 124 can further use the target modality 2D images generated by the multimodal training data generation module 101 to train and develop the one or more inferencing models 126'.

In some implementations, the input data (e.g., the native 3D image data 102 and/or the paired native 2D image data 104) used by the multimodal training data generation module 101 to generate the synthetic 2D images 116, the annotated synthetic 2D images 118, and annotated native 2D can also be added to the training data 122 and used by the training module 124 to train and develop the one or more inferencing models 126'. Any ground truth information received and/or generated by the multimodal training data generation model 101 can also be added to the training data 122 and used by the training module in association with training and developing the one or more inferencing models 126' (e.g., annotated native 3D image data 108, and/or annotated paired native 2D images 110).

In various embodiments, the multimodal training data generation module 101 can facilitate generating and annotating high quality training images in the target 2D capture modality using corresponding image data captured and/or generated in a different source capture modality. In one or more embodiments, this different source capture modality can comprise a 3D capture modality (e.g., CT, MRI, and/or other types of 3D capture modalities in the medical or non-medical domain). The multimodal training data generation module 101 can further employ the native 3D images to facilitate generating and annotating high quality training images in the target 2D capture modality. (However, in some embodiments, the different source modality can include other 2D imaging modalities). To facilitate this end, the multimodal training data generation module 101 can include annotation component 106, transformation component 112 and annotation transfer component 114.

In this regard, the multimodal training data generation module 101 can receive native 3D image data 102 comprising 3D images of an object or environment captured and/or generated in a 3D capture modality. For example, the 3D images can comprise 3D volume images, 3D models, 3D representations or the like. In some implementations, image data used to generate the 3D images can also be included in the native 3D image data 102 and respectively associated with the 3D images. For example, as applied to CT volume images, MRI volume images and the like, the individual CT and MRI scans used to generate the 3D volume images can also be included in the native 3D image data 102 and associated with the respective volume images. The 3D images can also be associated with metadata describing relevant information associated with the respective 3D images, including but not limited to: patient information (e.g., demographics, medical history, current medical condition, etc.), capture modality information, capture parameter information, capture protocol information, and image feature information (e.g., orientation, field of view, resolution, etc.).

In one or more embodiments, the transformation component 112 can generate one or more synthetic 2D images from a native 3D image included in the native 3D image data 102, wherein the synthetic 2D images correspond to a 2D version of the native 3D image. In this regard, the transformation component 112 can essentially transform a native 3D image captured and/or generated in a 3D capture modality into one or more corresponding synthetic 2D images that correspond to 2D versions of the 3D image in the target capture modality. For example, in some implementations, the 3D image can be a CT volume image and the transformation component 112 can transform the CT volume image into an SXR image. The transformed synthetic 2D images are represented in FIG. 1 as synthetic 2D images 116.

To facilitate generating a plurality of image exemplars for the purpose of ML training and development, the native 3D image data 102 can comprise different 3D images captured using a source capture modality and depicting same or similar subject matter. For example, as applied to the medical imaging domain, the native 3D image data 102 can comprise 3D images captured for different patients and respectively depicting a same anatomical region for a medical condition manifested in the anatomical region. In accordance with this example, for each patient, the transformation component 112 can generate one or more synthetic 2D images from the corresponding 3D image for the patient, wherein the one or more synthetic 2D images correspond to 2D versions of the 3D image.

In some implementations, the transformation component 112 can generate the synthetic 2D images 116 from the native 3D image data 102 alone. For example, in various implementations in which the native 3D image data 102 comprises CT image data (e.g., CT volume data) for different patients, the transformation component 112 can generate SXR images from the corresponding CT image data alone.

Additionally, or alternatively, the transformation component 112 can receive and employ paired native 2D images 104 from the target capture modality to facilitate generating the synthetic 2D images 116 in the target capture modality. With these embodiments, the paired native 2D images 104 can comprise native 2D images captured in the target capture modality that are paired with corresponding 3D images in the native 3D image data 102. The respective native 3D and 2D images included in a pair can be considered paired because they both depict the same object or environment in a same or similar state. In this regard, an ideal pair of native 3D modality image data and native 2D modality image data would include image data respectively captured using the different capture modalities of the same object/environment at the same time and from the same viewpoint.

For example, as applied to medical image processing, the native 3D image data 102 and the paired native 2D images 104 can respectively include paired 3D images from a source modality and 2D images from a target modality of a number of different patients, wherein each image pair corresponds to images acquired of the same anatomic region with a similar state of at least one medical condition of the patient. In some example implementations, the native 3D image data of a pair can comprise a CT image study (e.g., including the computed CT volume and optionally the individual CT scan slices) of an anatomical region of a patient and the native 2D image data of the pair can comprise an XR image of the same anatomical region of the same patient, wherein both the CT image data and the XR image depict the same medical condition/disease of the patient in a same or similar state. For fast moving medical diseases/conditions such as respiratory disease/pneumonia in patients with COVID-19, the closer in time the respective 3D image data and 2D image data are captured from the patient the better (e.g., preferably less than 48 hours and more preferably less than 24 hours). In some embodiments, the native 3D image data and the native 2D image data of a pair can respectively be associated with timestamps indicating their capture times to facilitate calibrating differences between the image data during processing and/or determining the best processing pathway for the image data.

In accordance with embodiments in which a paired native 2D image is provided (e.g., in the paired native 2D images 104) for a 3D image included in the native 3D image data 102, the transformation component 112 can employ the paired native 2D image 104 to facilitate generating more realistic synthetic 2D images (e.g., synthetic 2D images 116) from the 3D image. The annotation transfer component 114 can also employ the paired native 2D image to facilitate accurately transferring ground truth annotation data applied to or otherwise associated with a native 3D image to the synthetic 2D image (or images) generated therefrom and/or the paired native 2D image.

In this regard, in various embodiments, the annotation transfer component 114 can transfer ground truth data for a 3D image to a synthetic 2D image generated therefrom. Synthetic 2D images annotated in this manner are represented in FIG. 1 annotated synthetic 2D images 118. As described below, with reference to the annotation component 106, this ground truth data can be manually applied to the 3D image after reception by the multimodal training data generation module 101 or previously applied to the 3D image and included with the 3D image in the native 3D image data. In some implementations, the annotation transfer component 114 can transfer ground truth data for a 3D image to a synthetic 2D image generated therefrom without the assistance or guidance provided by a paired native 2D image for the 3D image (e.g., in implementations in which a paired native 2D image is not available). In other embodiments in which a paired 2D image is provided for the 3D image, the annotation transfer component 114 can employ the native 2D image to facilitate accurately positioning and sizing the ground truth data on the synthetic 2D image in association with transfer of the ground truth data from the 3D image.

The annotation transfer component 114 can also transfer ground truth data for a 3D image to a paired native 2D image. Native 2D images annotated in this manner are represented in FIG. 1 annotated native 2D images 120. In some embodiments, the annotation transfer component 114 can similarly employ one or more corresponding synthetic 2D images generated from the 3D image to facilitate accurately positioning and sizing the ground truth data on the paired native 2D image in association with transfer of the ground truth data from the 3D image. In some embodiments, the annotation transfer component 114 can also transfer ground truth data applied to a paired native 2D image to one or more corresponding synthetic 2D images generated from its paired 3D image. Synthetic 2D images annotated in this manner can be included in the annotated synthetic 2D images 118.

In the embodiment shown, the multimodal training data generation module 101 can include annotation component 106 to facilitate manually applying ground truth data to one or more of the 3D images included in the native 3D image 102 and/or one or more of the paired native 2D images 104. Native 3D images annotated in this manner are represented in FIG. 1 as annotated native 3D image data 108 and paired native 2D images annotated in this manner a represented in FIG. 1 as annotated paired native 2D images. In this regard, in some embodiments, the annotation component 106 can provide the native 3D image data 102 and/or the paired 2D images 104 to one or more annotators for manual application of ground truth data. For example, in one embodiment, the annotation component 106 can include and/or interface with a manual annotation application that presents (e.g., via a device display or another suitable output device 2636) one or more manual annotators (humans) with unannotated (or in some implementations previously annotated) native images for annotation. For instance, in implementations in which the images comprise medical images, the annotation application can provide for rendering the unannotated medical images to a manual annotator (e.g., a radiologist) and receiving input from the manual annotator that identifies or indicates a desired ground truth interpretation for the medical image. For example, the ground truth data can include manually applied classifiers, labels, segmentation masks (e.g., organ segmentation masks), marked regions of interest (ROI) such as disease regions in medical image data, measurement data indicating one or more dimensions of features in the image, and the like.

The annotation application can further generate ground truth data for the annotated images and associated the ground truth data with the respective images in accessible memory storage (e.g., as annotated native 3D image data 108 and/or annotated paired native 2D images 110). Thus, in some embodiments, the annotated native 3D image data 110 can include marked-up versions of the 3D image data with the ground truth marked thereon. Additionally, or alternatively, the ground truth data can be separated from the native 3D image data and associated therewith as a separate file, metadata, or the like. The annotation component 106 can generate and associate ground truth annotation data for the paired native 2D images 104 in the same manner.

Additionally, or alternatively, the native 3D image data 102 (and optionally the paired native 2D images 104) can be received with previously applied ground truth data. With these embodiments, the previously applied ground truth data can be received for respective 3D images included in the native 3D image data 102 as marked up versions of the respective 3D images (e.g., both an annotated and original version of the 3D images can be received), as metadata associated with respective 3D images, as separate annotation files associated with the respective 3D images, or the like. In some implementations, previously applied ground truth annotation data for one or more of the paired native 2D images can be received in a same or similar manner.

In various embodiments, the annotation component 106 can also provide for manual review of transferred annotations. In particular, the annotation component 106 can present transferred ground truth data that was transferred by the annotation transfer component 114 from an annotated 3D image to a corresponding native 2D image and/or a corresponding synthetic 2D image to one more manual annotators for optional manual review and adjustment.

Additional details regarding the features and functionalities of the transformation component 112 and the annotation transfer component 114 are described in greater detail in the with reference to FIGS. 2-25.

Figure 2:
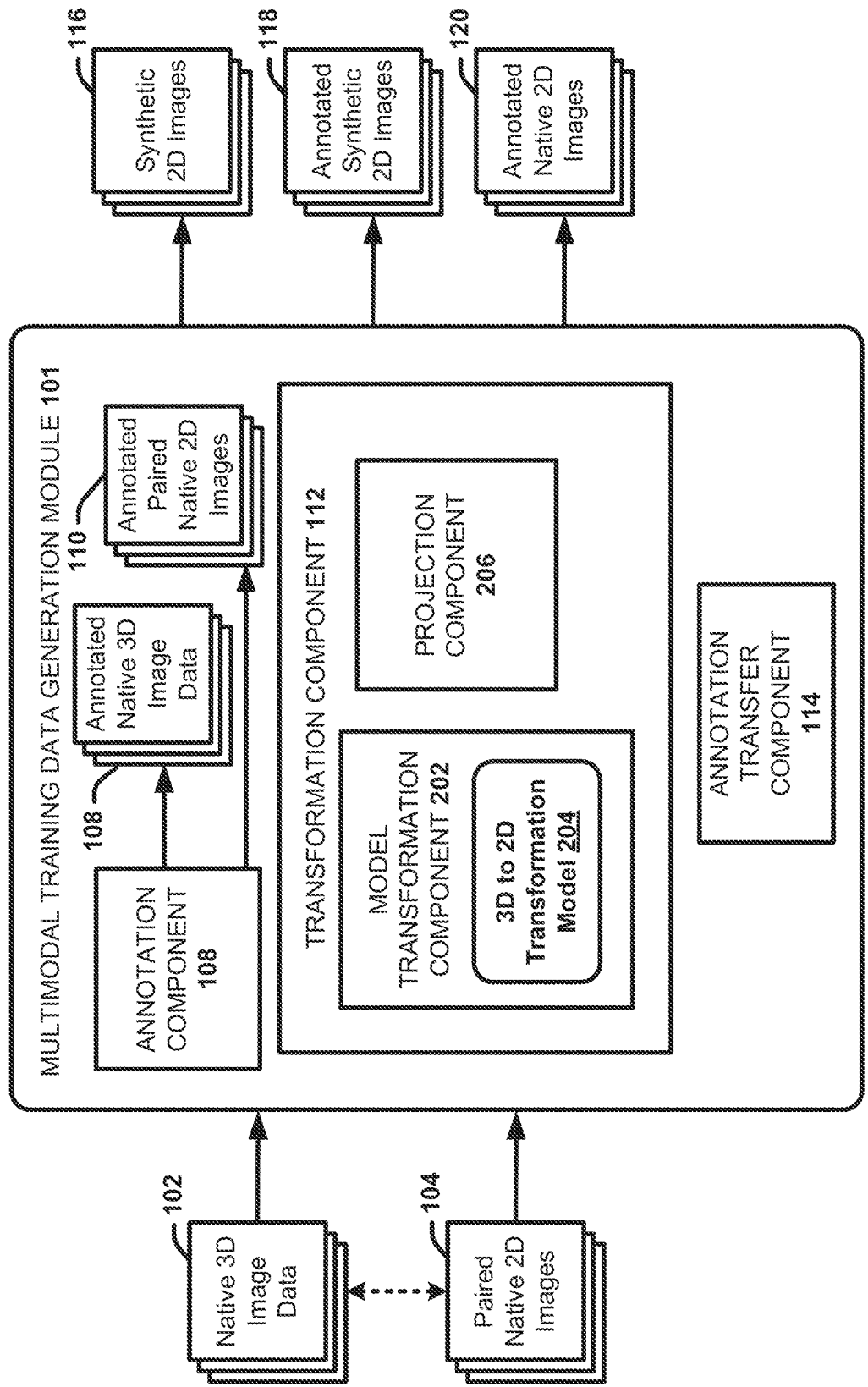
FIG. 2 presents an example multimodal training data generation module in accordance with one or more embodiments of the disclosed subject matter.

FIG. 2 presents an example multimodal training data generation module 101 in accordance with one or more embodiments of the disclosed subject matter. In accordance with the embodiment shown, the multimodal training data generation module 101 can receive and process native 3D image data 102 and/or paired native 2D images 104 to generate synthetic 2D images 116, annotated synthetic 2D images 118 and/or annotated native 2D images for addition to the training data 122. To facilitate this end, the transformation component 112 can include model transformation component 202 and projection component 206. Repetitive description of like elements employed in respective embodiments is omitted for sake of brevity.

In some embodiments, transformation component 112 can employ model transformation component 202 to generate one or more synthetic 2D images from a 3D image using a 3D to 2D transformation model 204. With these embodiments, the 3D to 2D transformation model 204 can comprise a previously trained neural network model configured to transform a 3D image into a 2D image that corresponds to a 2D version of the 3D image in a target capture modality. In some implementations, in addition to generating a 2D image in the target capture modality, the 3D to 2D transformation model 204 can also tailor one or more visual appearance properties of the output images, including but not limited to: color, saturation, contrast, hue, density, brightness, field of view (FOV), orientation, dimensionality, demography, or the like.

Figure 3:
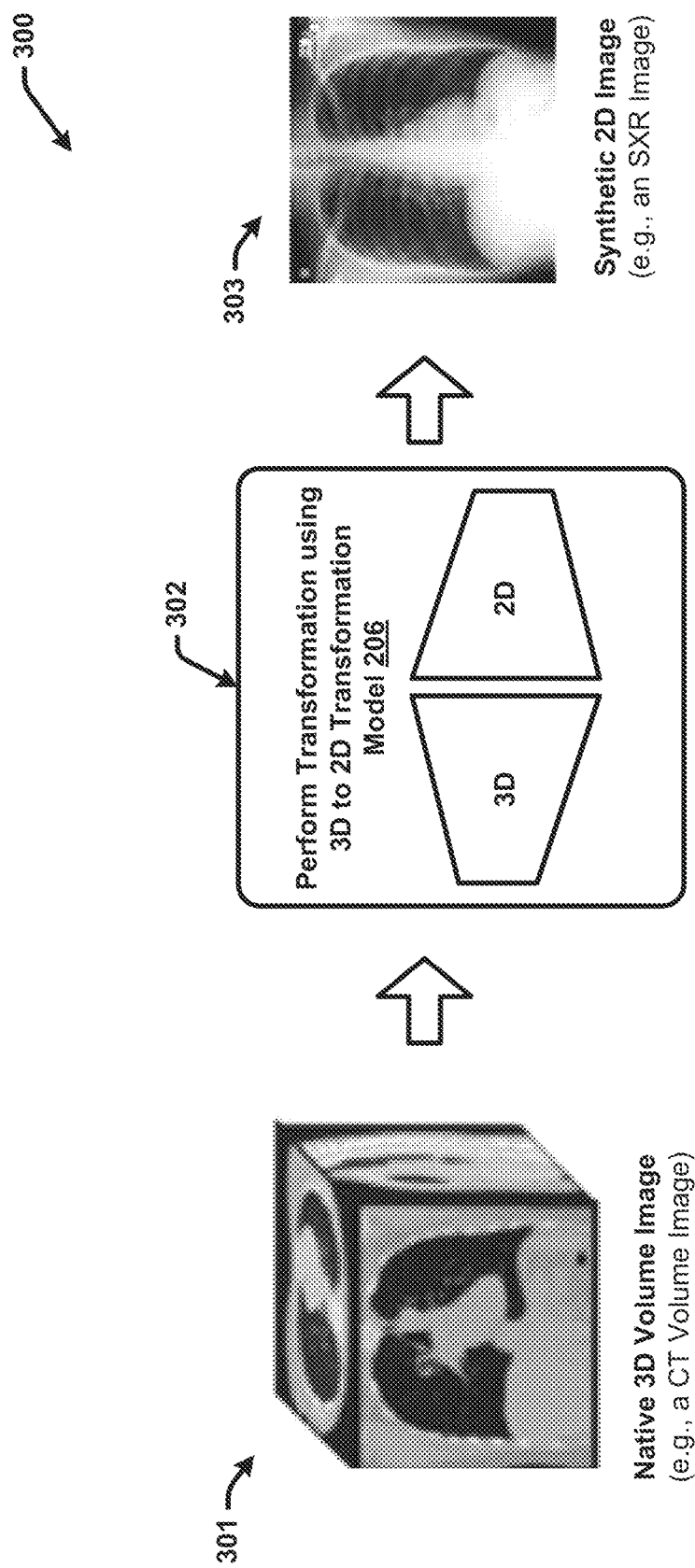
FIG. 3 presents a high-level flow diagram of an example process for generating a synthetic 2D image from a 3D image using a transformation model in accordance with one or more embodiments of the disclosed subject matter.

FIG. 3 presents a high-level flow diagram of an example process 300 for generating a synthetic 2D image from a 3D image using a 3D to 2D transformation model 204 in accordance with one or more embodiments of the disclosed subject matter. With reference to FIGS. 2 and 3, in accordance with process 300, the model transformation component 202 can directly transform a native 3D volume image 301 into a synthetic 2D image 303 by applying the 2D to 3D transformation model to the native 3D volume image at 302. In the embodiment shown, the native 3D volume image 301 comprises a CT image volume image of a patient's chest and the synthetic 2D image 303 comprises an SXR image.

In one or more embodiments, the 3D to 2D transformation model 206 comprises a generative adversarial network (GAN). In this regard, GAN models can be configured to generate realistically looking synthetic images after learning the training image data distribution. As applied to 3D image to 2D image transformation, the training distribution can comprise a plurality of 3D images (e.g., 3D volume images) and corresponding accurate synthetic 2D images for the respective 3D images. In various embodiments, this training data can be generated by the multimodal training data generation module 101 and/or additional multimodal training data modules discussed herein using the projection component 206 and the various multimodality image processing techniques discussed infra. In this regard, as described in greater detail infra, the disclosed subject matter provides various projection processing-based transformation techniques to generate realistic synthetic 2D images from 3D images with a wide distribution of variations. Thus, in various embodiments, the training module 124 (or another training system) can train and develop the 3D to 2D transformation model 206 using these synthetic 2D images and their corresponding 3D images.

A GAN generally involves two neural networks, a generative network (also referred to as the encoder) and a discriminative network (also referred to as the decoder). In various implementations, the mean squared error (MSE) loss and adversarial loss can be combined to train the generator network of the 3D to 2D transformation model 206. In some implementations, the discriminator network of the 3D to 2D transformation model 206 can perform 2D convolutions and up-sampling operations, wherein skip connection can occur between the generator network and the decoder network.

The 3D to 2D transformation model 204 however is not limited to a GAN. In this regard, various other types of machine learning models can be used for the 3D to 2D transformation model 204 and trained using the synthetic 2D images generated via the projection processing techniques described herein and their corresponding 3D volumes. For example, the 3D to 2D transformation model 204 can include various other types of network models, DNNs, CNNs, GANs, and combinations thereof. Other suitable machine learning models that can be used for the 3D to 2D transformation model 204 can include (but are not limited to): nearest neighbor (NN) models (e.g., k-NN models, replicator NN models, etc.), statistical models (e.g., Bayesian networks, etc.), clustering models (e.g., k-means, etc.), neural networks (e.g., reservoir networks, artificial neural networks, etc.), support vector machines (SVMs), and combinations thereof.

With reference again to FIG. 2, in various embodiments, in addition or alternative to using the model transformation component 202 to generate synthetic 2D images 116, the transformation component 112 can employ projection component 206 to generate the synthetic 2D images. In this regard, the projection component 206 can perform projection processing of a 3D volume image included in the native 3D image data 102 to generate one or more corresponding synthetic 2D images (e.g., synthetic 2D images 116). Projection processing involves projection a three-dimensional object view onto a two-dimensional plane. With these embodiments, the projection processing employ various known projection processing techniques to generate a synthetic 2D image from a 3D volume image. For example, in some implementations, the projection component 206 can employ parallel projection processing. Additionally, or alternatively, the projection component 206 can employ point source projection processing (also referred to as perspective projection processing). These projection processes are illustrated in FIGS. 4A and 4B.

Figure 4A:
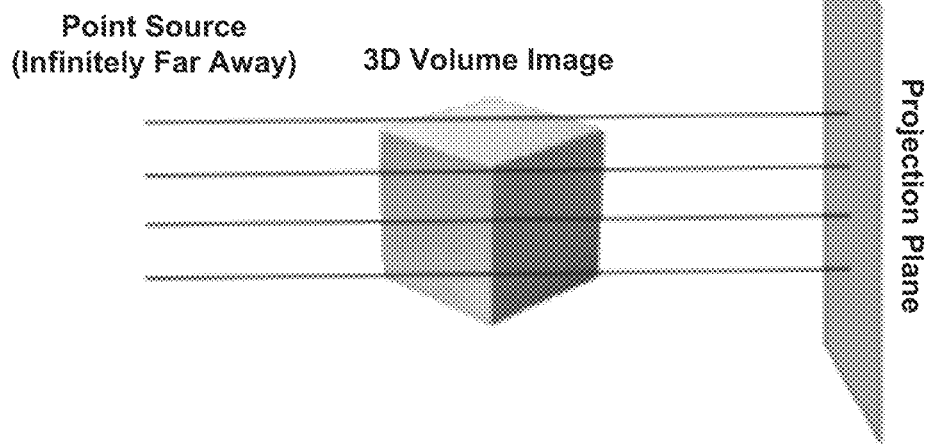
FIGS. 4A and 4B illustrate example projection processes for generating a synthetic 2D image from a 3D image in accordance with one or more embodiments of the disclosed subject matter.
Figure 4B:
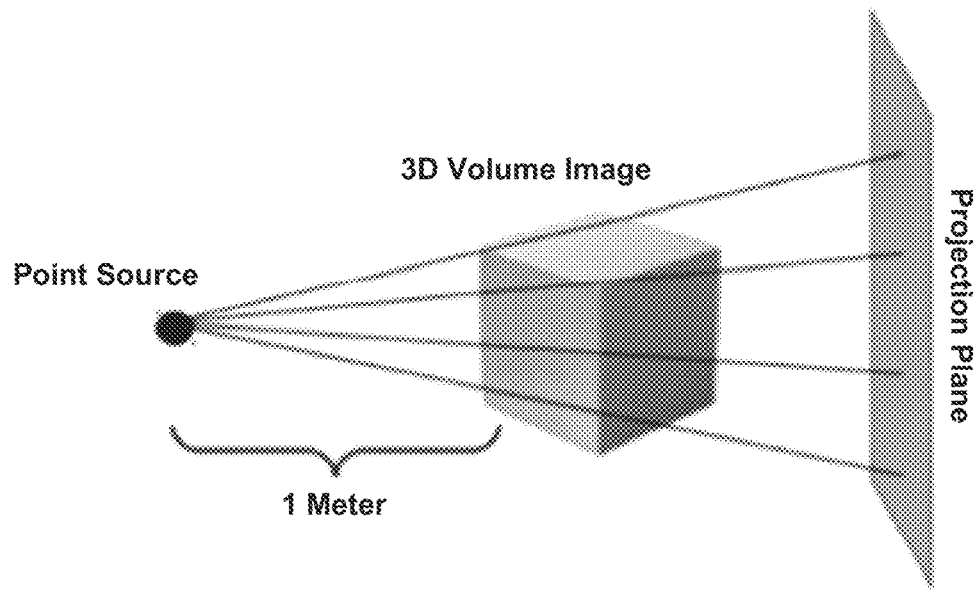

In this regard, FIG. 4A provides an example illustration of parallel projection processing and FIG. 4B provides an example illustration of point source projection processing. With reference to FIG. 4A, parallels projection processing involves projection of an object in three-dimensional space onto a fixed plane, known as the projection plane or image plane, where the rays, known as lines of sight or projection lines, are parallel to each other. With parallel projection, the point source can be infinitely far away from the 3D volume image. With reference to FIG. 4B point source projection also involves projection of an object in three-dimensional space onto a fixed plane projection plane. Point source projection differs from parallel projection in that the points source is located at a fixed viewpoint of the 3D object. In this regard, the point source corresponds to the viewpoint of an observer and the projection rays fan out from the viewpoint in accordance with lines of sight of a viewer from the viewpoint.

Figure 5:
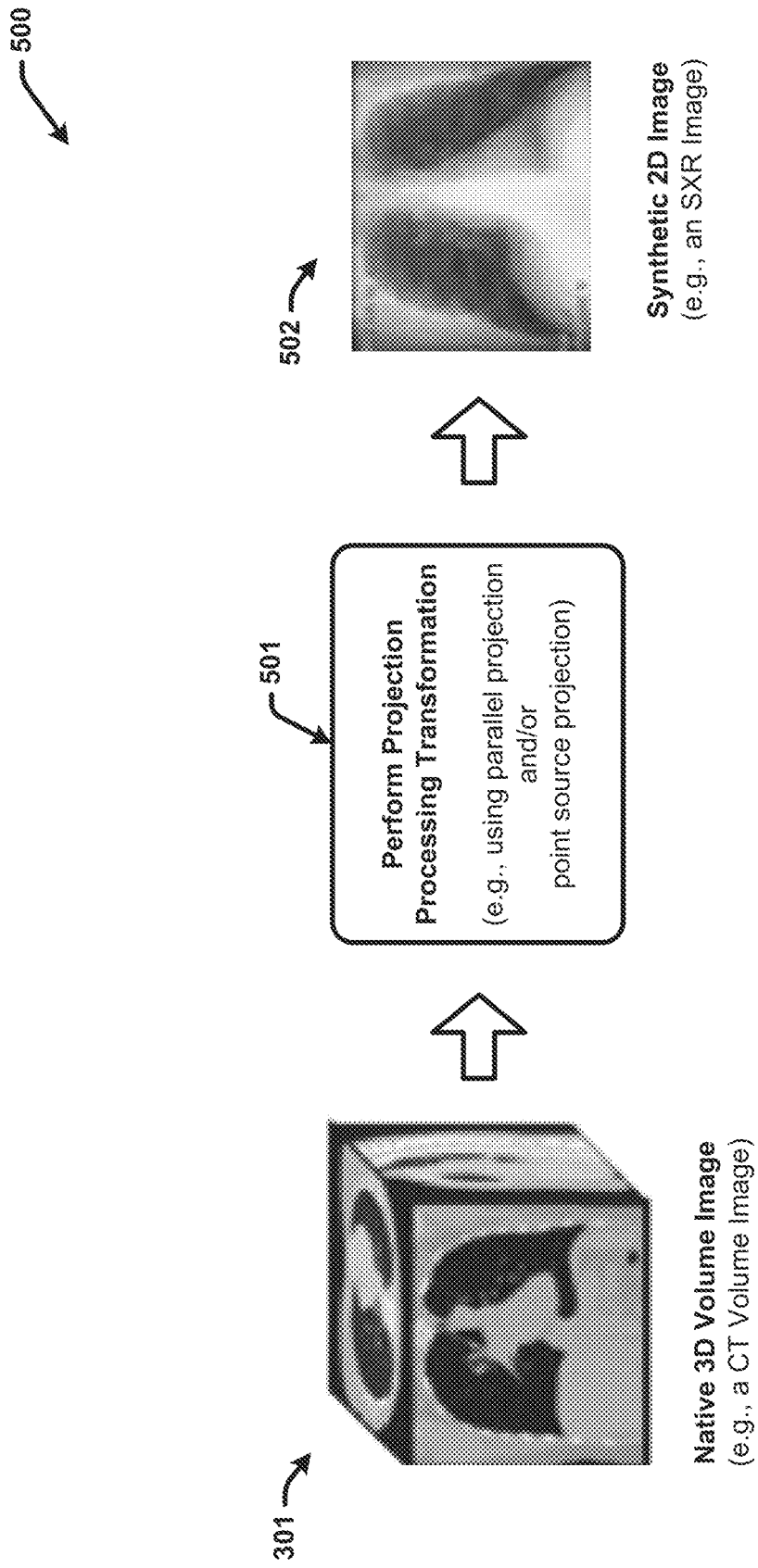
FIG. 5 presents a high-level flow diagram of an example process for generating a synthetic 2D image from a 3D image using projection processing in accordance with one or more embodiments of the disclosed subject matter.

FIG. 5 presents a high-level flow diagram of an example process 500 for generating a synthetic 2D image from a 3D image using projection processing in accordance with one or more embodiments of the disclosed subject matter. With reference to FIGS. 4 and 5, in accordance with process 500, the projection processing component 206 can generate a synthetic 2D image 502 from the native 3D volume image 301 by performing projection processing using parallel projection processing and/or point source projection processing at 501. In this regard, using parallel projection or points source projection, the projection component can project the 3D image data of the 3D volume image onto a projection plane and generate a 2D representation of 3D image data as projected onto the projection plane. The projection component 206 can employ various known projection algorithms to compute the 3D to 2D image transformation based on the source 3D image modality and the target 2D image modality, the projection process used, and the projection parameters used. In the embodiment shown, the native 3D volume image 301 comprises a CT image volume image of a patient's chest and the synthetic 2D image 502 comprises an SXR image.

Figure 6:
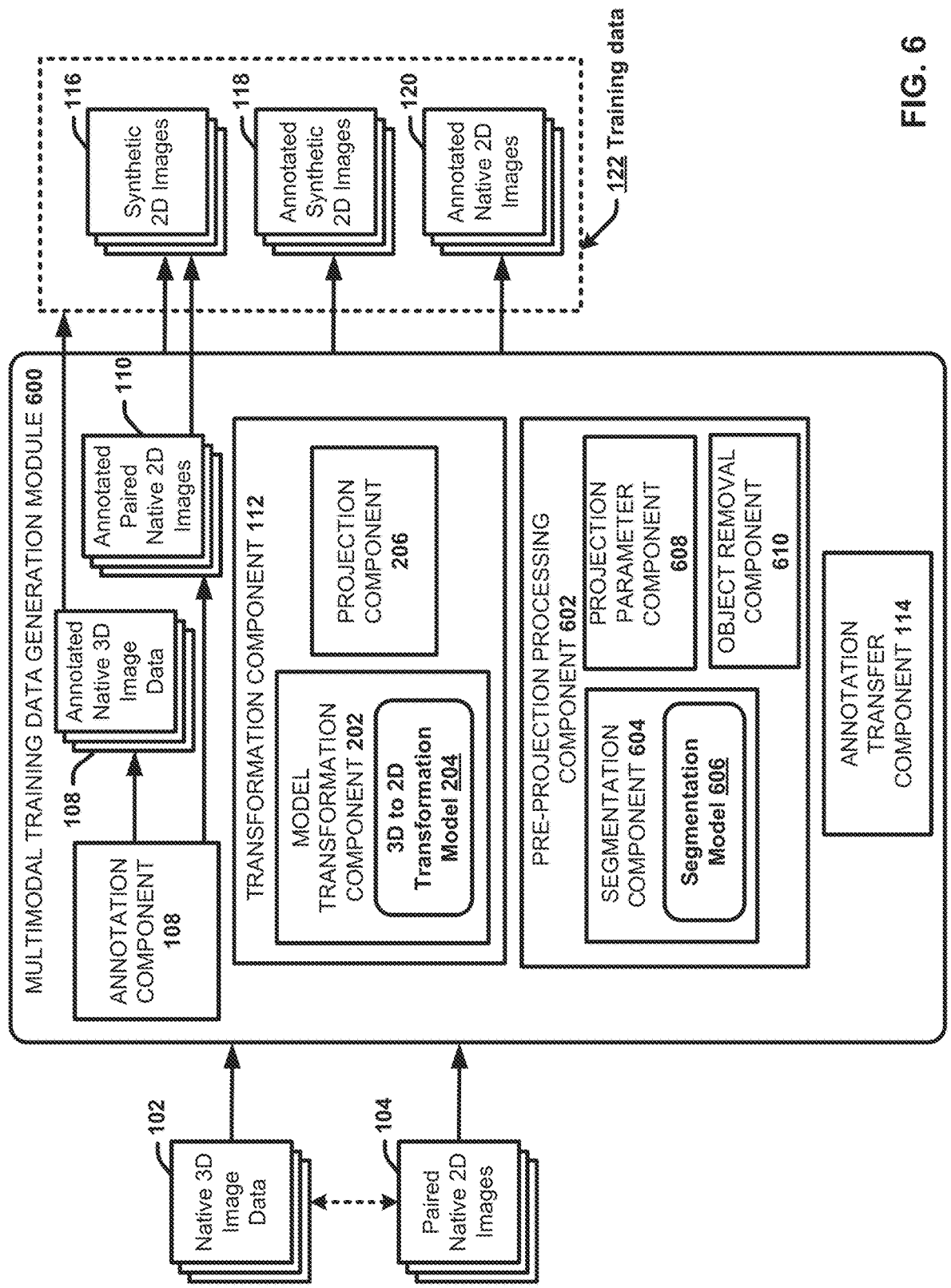
FIG. 6 presents another example multimodal training data generation module in accordance with one or more embodiments of the disclosed subject matter.

FIG. 6 presents another example multimodal training data generation module 600 in accordance with one or more embodiments of the disclosed subject matter. Multimodal training data generation module 600 can include same or similar features and functionalities as multimodal training data generation module 101 with the addition of pre-projection processing component 602. Repetitive description of like elements employed in respective embodiments is omitted for sake of brevity.

The pre-projection processing component 602 can perform various techniques to further improve the quality and realistic appearance of synthetic 2D images generated by the projection component 206 using one or more pre-projection processing steps. To facilitate this end, pre-projection processing component 602 can include segmentation component 604, projection parameter component 608, and object removal component 610.

In one or more embodiments, the projection parameter component 608 can determine the optimal projection parameters for the 3D to 2D projection that will result in the best quality output 2D image. In this regard, as applied to generation of an a synthetic 2D image in a target capture modality from a 3D volume image in a source capture modality, the projection parameter component 608 can determine the optimal projection parameters for the projection that will result in the most realistic synthetic 2D image in the target modality (e.g., wherein realistic in this context refers to the synthetic image looking as if it was actually captured using the target capture modality). For example, as applied to generation of an SXR image from a CT volume image, the projection parameter component 608 can determine the optimal projection parameters for the projection that will result in the most realistic looking SXR.

In addition to considering the target capture modality for the synthetic 2D image, the projection parameter component 206 can also determine the optimal projection parameters based various other desired factors for the output image, such as orientation, FOV, ROI, and the like. For example, as applied to the generation of SXR images, the optimal projection parameters will vary based on whether the desired SXR image should be an anterior-posterior (AP) projection or a posterior-anterior (PA) projection.

In embodiments in which the projection component 206 employs point source projection, the projection parameters determined can include, but are not limited to: the source point and position, the projection plan position, and the projection angle. In this regard, with reference to FIG. 4B, in some implementations the point source position can include the distance between the point source and the intersection point between the 3D model and the center projection ray. Additionally, or alternatively, the point source position can include the distance between the point source and the intersection point between a specific point, object, plane or region within the 3D volume image. For example, as applied to medical images, the specific point can refer to a location of a specific anatomical body part. The projection plane position refers to the distance between the back surface of the 3D volume image and the projection plane. The projection angle can refer to the intersection angle of the center projection ray and the intersection point on or within the 3D volume image.

In some embodiments, the projection component 206 can determine the optimal projection parameters based on segmentation of one or more 3D objects take from the 3D volume image. For example, as applied to medical images, the projection component 206 can determine the optimal projection parameters based on organ and body segmentation data for the 3D volume image that segments the organs from the body in 3D. In this regard, the 3D volume image can comprise a 3D representation of an anatomical region of a patient in which a medical condition is present. For example, in various implementations, the 3D volume image can comprise a CT volume image, an MRI volume image, an US volume image or the like. With these implementations, the 3D volume images can be generated based on a plurality of sequential 2D scan image captured at different planes. The 3D volume image can thus provide a 3D model of the anatomical region depicting various internal body parts within the anatomical region.

In various embodiments, the organ and body segmentation data can include information that identifies the relative positions and geometry (e.g., dimensions, size and shape, etc.) of one or more organs and/or anatomical body parts included in the 3D volume data. Additionally, or alternatively, the organ and body segmentation data can include image data (e.g., in 2D or 3D) that segments and isolates the one organs and/or body parts from one another. For example, as applied to a CT volume image of a patient's chest, the organ and body segmentation data can include lung segmentation data that segments the patient's lungs in the image data from the rest of the body in the image data. The lung segmentation data can also indicate the relative position of the lungs to the back of the body, the side of the body, the front of the body, and so on.

In the embodiment shown, the pre-projection processing component 602 can include segmentation component 202 to perform the organ/body segmentation and generate the organ and body segmentation data for the 3D volume image. For example, the segmentation component 202 can employ a segmentation model 606 configured to process 3D volume data and/or associated 3D data (e.g., one or more CT scan slices or the like) and generate segmentation data that isolates and segments one or more target organs and/or body parts from one another in image data in 3D (and optionally in 2D). Additionally, or alternatively, the organ and body segmentation data can be previously generated and provided with the 3D volume image in the native 3D image data 102.

Regardless of how the organ and body segmentation data is generated and/or received, the projection parameter component 608 can employ the organ and body segmentation data to determine the optimal projection parameters. In this regard, in implementations in which point source projection is used, the projection parameter component 608 can employ the organ and body segmentation data to determine the optimal point source position and the projection angle. In particular, the projection parameter component 608 can employ information in the segmentation data identifying the relative positions of one or more organs to other parts of the body and/or dimensions/geometry of the one or more organs to determine the optimal projection point and projection angle. The projection parameter component 608 can also employ predefined and/or learned criteria for determining the optimal projection point and projection angle based on the relative position and dimension information.

For example, in one implementation as applied to a chest CT volume image the projection parameter component 608 can be configured to determine the projection point and projection angle such that the center projection of the point source intersects in the middle of the lungs. In another example, the projection parameter component 608 can position the point source such that the distance between the point source and the back of the body is N centimeters (cm) (e.g., 90 cm) for generating an SXR with anterior-posterior imaging. In this regard, the projection parameter component 608 can employ the organ segmentation data as a reference to normalize the projection point and the projection angle.

In another embodiment, the projection parameter component 608 can determine the optimal projection based on comparative analysis of different synthetic 2D images generated from the same 3D volume image using different candidate projection parameters. In some implementations of these embodiments in which a native 2D image corresponding to the 3D volume image is available, the different synthetic 2D images can be compared to the native 2D image and evaluated using one or more similarity metrics to identify the best matching synthetic 2D image. With these embodiments, the parameters used to generate the best matching synthetic 2D image can be used as the standard projection parameters for all (or in some implementations one or more) 3D volume images when used for generating a synthetic 2D image in the same target modality.

The object removal component 610 can also facilitate enhancing the quality of the output synthetic 2D image in association with projection generation by performing object removal processing on the 3D volume image prior to projection. In this regard, the object removal component 610 can remove unwanted objects and/or artifacts appearing in the 3D volume image prior to projection, resulting in a refined 3D volume image. For example, in some implementations as applied to medical images, the object removal component 610 can remove objects or features appearing in the 3D volume image that are not body parts (e.g., part of the imaging table, part of the imaging equipment, etc.). The object removal component 610 can also remove objects or artifacts appearing in the 3D volume image that are not typically depicted in the target capture modality for the synthetic 2D image. For example, as applied to generation of an SXR image from a CT volume image, the object removal component 610 can remove high detail anatomical features present in the CT volume image data that are not captured in XR data.

Figure 7:
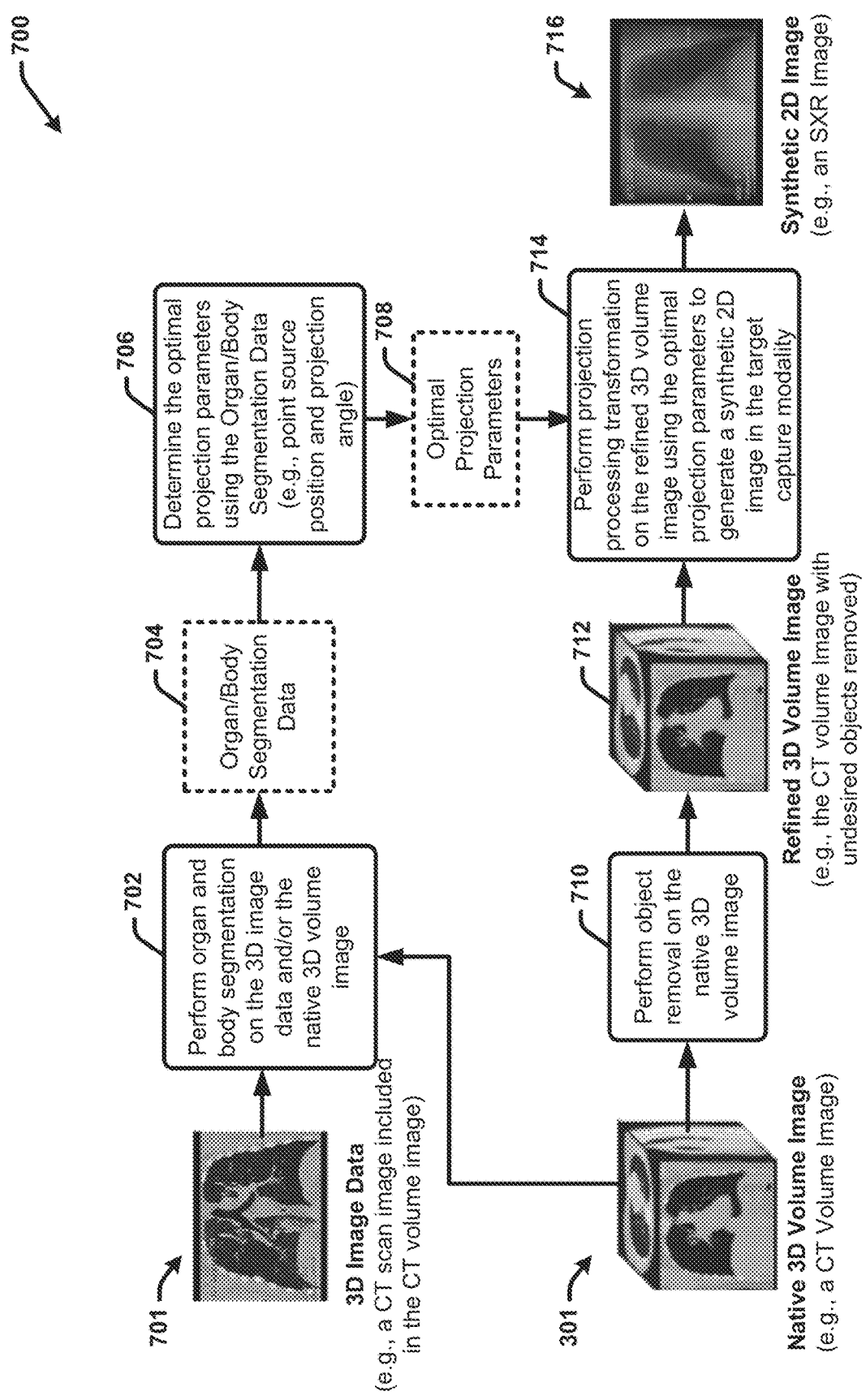
FIG. 7 presents an example process for generating a synthetic 2D image from a 3D image using projection processing in accordance with one or more embodiments of the disclosed subject matter.

FIG. 7 presents an example process 700 for generating a synthetic 2D image from a 3D image using projection processing in accordance with one or more embodiments of the disclosed subject matter. In this regard, process 700 demonstrates the some of the high-level features and functionalities of the projection component 206 and the pre-projection processing component 602 discussed above as applied to the generation of an SXR image from a CT volume image. Repetitive description of like elements employed in respective embodiments is omitted for sake of brevity.

With reference to FIGS. 6 and 7, in accordance with process 700 the multimodal training data generation module 600 can receive/acquire (e.g., from the native 3D image data 102) a CT volume image (e.g., native volume image 301) for a patient and associated 3D image data 701 for the 3D volume image 301. The associated 3D image data can include one or more of the individual CT scan images used to generate the CT volume image. In the embodiment shown, the CT image data depicts the patient's chest.

In this regard, at 702, the segmentation component 604 can perform organ and body segmentation on the 3D image data 701 to generate organ/body segmentation data 704. For example, in some embodiments, the segmentation component 604 can apply a segmentation model (e.g., segmentation model 606) to the CT scan image to generate the organ/body segmentation data 704. In accordance with this example, the segmentation model can be configured to process CT scan images of the chest to generate segmentation data that isolates the lungs from the body and/or determines the relative position of the lungs to the back of the body, the front of the body, etc. Additionally, or alternatively, the at 702, the segmentation component 604 can process the native 3D volume image 301 to generate the organ/body segmentation data 704 (e.g., using a different segmentation model tailored to chest CT volume segmentation). The resulting segmentation data can include one or more objects (e.g., organs, body parts, etc.) segmented from the native 3D volume image 301, and/or geometry and position information derived therefrom that defines the geometry of the segmented objects in 3D and/or the relative positions of the objects to one another in 3D.

At 706, the projection parameter component 608 can determine the optimal projection parameters 708 using the organ/body segmentation data. For example, in implementations in which point source projection is used, the projection parameter component 608 can determine the optimal point source position and projection angle). In association or in parallel with performing the organ and body segmentation and determining the optimal projection parameters, at 710, the object removal component 610 can perform object removal on the native 3D volume image to generate a refined 3D volume image 712 (e.g., the CT volume image with undesired objects removed). At 714, the projection component can perform projection processing transformation of the refined 3D volume image 712 using the optimal projection parameter 708 to generate a synthetic 2D image 716 in the target capture modality. In the embodiment shown, the target capture modality comprises XR and thus the resulting synthetic 2D image 716 is realistic SXR image.

Figure 8:
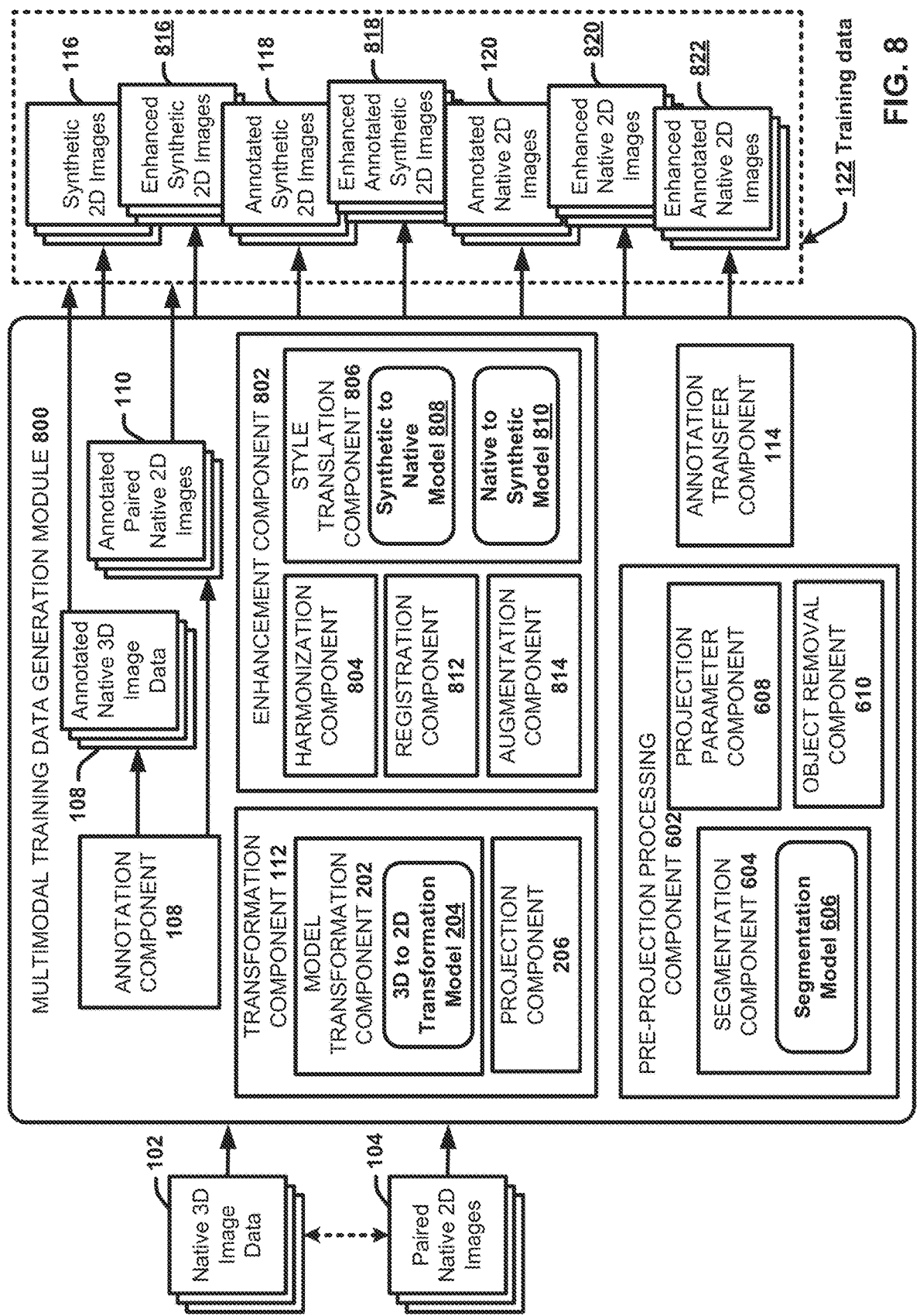
FIG. 8 presents another example multimodal training data generation module in accordance with one or more embodiments of the disclosed subject matter.

FIG. 8 presents another example multimodal training data generation module 800 in accordance with one or more embodiments of the disclosed subject matter. Multimodal training data generation module 800 can include same or similar features and functionalities as multimodal training data generation module 600 with the addition of enhancement component 802. Repetitive description of like elements employed in respective embodiments is omitted for sake of brevity.

The enhancement component 802 can perform various techniques to further improve the quality and realistic appearance of synthetic 2D images 116 generated by the transformation component 112 using one or more post-projection processing steps. In this regard, the enhancement component 802 can facilitate further enhancing the quality and diversity of the training data included in the training data dataset 122. For example, in the embodiment shown, the training data 122 can further include enhanced synthetic 2D images 816, enhanced annotated synthetic 2D images 818, enhanced native 2D images 820, and/or enhanced annotated native 2D images 822. To facilitate this end, enhancement component 802 can include harmonization component 804, style translation component 806, registration component 812, and augmentation component 814.

The harmonization component 804 can perform image harmonization on synthetic 2D images 116 using one or more reference images of the target capture modality to make the appearance of the synthetic 2D images 116 more similar to that of the one or more reference images. For example, in implementations in which the synthetic 2D images comprise SXR images, the harmonization component 804 can harmonize the SXR images with one or more reference native SX images to make the SXR images look more similar in appearance to the one or more reference native SX images. In this regard, the image harmonization process can involve adapting/adjusting the visual appearance of the synthetic 2D images 116 to be more similar to that of the one or more reference images, resulting in transformation of the synthetic 2D images into harmonized synthetic 2D images. In accordance with the disclosed subject matter, harmonized synthetic 2D images can be considered enhanced images and can be included in the enhanced synthetic 2D images 816.

In implementations in which a paired native 2D image is provided for a 3D image used to generate the corresponding synthetic 2D image, the harmonization component 804 can employ the paired native 2D image as the reference image. In implementations in which a paired native 2D image is not available, the one or more reference images can comprise one or more preselected reference images that are representative of native 2D images in the target capture modality. Additionally, or alternatively, the harmonization component 804 can select the one or more representative reference images during the harmonization process (e.g., as part of the harmonization process). In this regard, the harmonization process employed by the harmonization component 804 can vary.

For example, in one or more embodiments, the harmonization component 804 can employ a harmonization process that involves decomposing the synthetic 2D image into sub-images and harmonizing the sub-images with corresponding reference sub-images decomposed from one or more reference images. In particular, the sub-images can be harmonized with the corresponding reference sub-images by adapting or modifying the sub-images to appear more similar to the corresponding reference sub-images, resulting in modified sub-images for the synthetic 2D image. In various embodiment the harmonization process can involve changing one or more features of each sub-image to make them more similar to the corresponding features of a corresponding reference sub-image. The modified sub-images can then be re-combined to generate a reconstructed, harmonized image that is a modified version of the synthetic 2D image having a more similar visual appearance to the one or more reference images relative to the synthetic 2D image.

In various embodiments, the style translation component 806 can further enhance the appearance of a synthetic 2D image using a style translation model configured to translate or transform a synthetic 2D image into the appearance style of the target 2D capture modality. This style translation model is represented in FIG. 8 as synthetic to native model 808. In this regard, the synthetic to native model 808 can comprise a GAN model (or another type of ML model) that has been trained to translate synthetic 2D images 116, and more preferably enhanced synthetic 2D images 816 (e g, enhanced via image harmonization and/or image registration), into the style of native 2D images in the target capture modality. The output of the synthetic to native model 808 includes an enhanced version of the synthetic 2D image that appears more similar to the native 2D images of the target capture modality relative to the synthetic 2D image. In various embodiments, the style translation component 806 (and/or the training module 124 or another model training system) can train and develop the synthetic to native model 808 using (at least some of) the paired native 2D images 104 and the corresponding enhanced synthetic 2D images 816 (e.g., preferably with harmonization and/or registration enhancement) generated from the from the 3D images respectively paired therewith. In accordance with the disclosed subject matter, style translated synthetic 2D images generated using the synthetic to native model 808 can be considered enhanced images and can be included in the enhanced synthetic 2D images 816.

In some embodiments, the style translation component 806 can also include a native to synthetic style translation model configured to perform the reverse transformation, represented in FIG. 8 as native to synthetic model 810. With these embodiments, the native to synthetic model 810 can also include a GAN model (or another ML model type) trained using the same training data used to train the synthetic to native model 808, yet configured to perform the reverse transformation, that is from a native 2D image to a synthetic 2D image or an enhanced synthetic 2D image. With these embodiments, the style translation component 802 can transform at least some of the paired native 2D images 104 (e.g., those not used for training) into enhanced native 2D images 820 with an appearance that is more similar to that of an enhanced synthetic 2D image. The style translation component 802 can also receive additional native 2D images that are not paired with corresponding 3D image data and transform them into enhanced native 2D images 820 with an appearance that is more similar to that of an enhanced synthetic 2D. These enhanced native 2D images 820 can be used to augment the amount and diversity of training images included in the training data pool.

Figure 9:
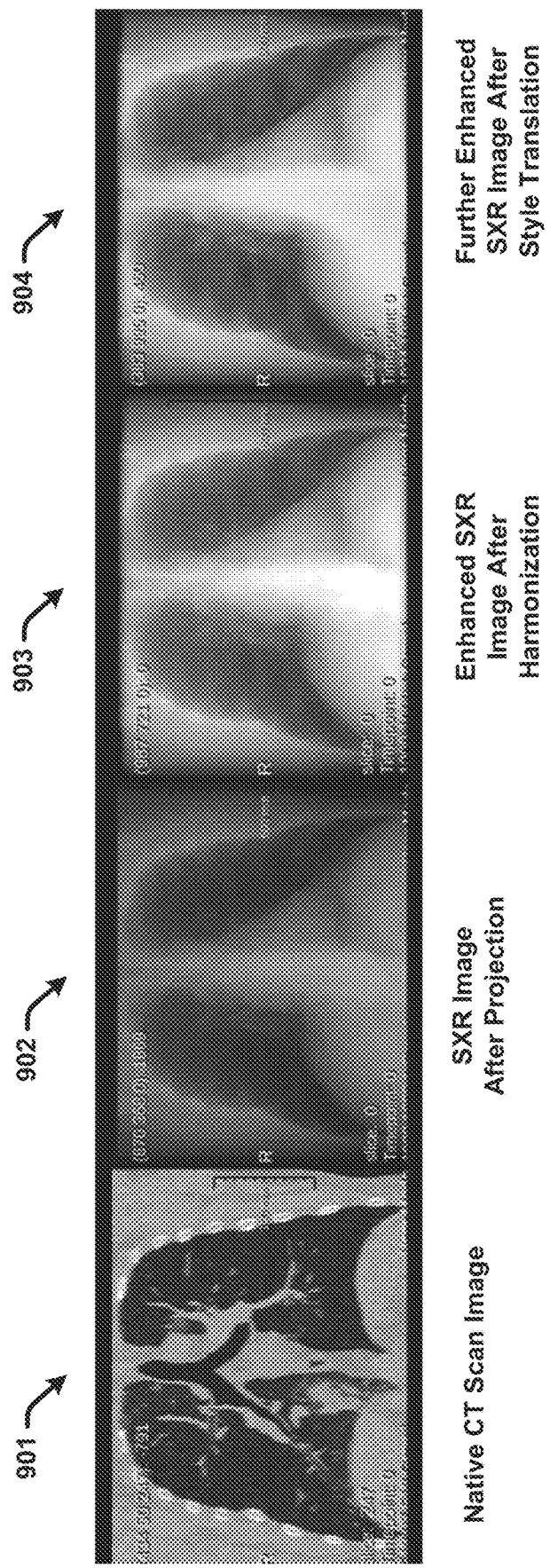
FIG. 9 present an example CT image and comparative SXR images generated after projection and post-processing enhancement in accordance with one or more embodiments.

FIG. 9 present an example native CT scan image (e.g., image 901) and comparative SXR images (e.g., images 902-904) generated after projection and post-processing enhancement in accordance with one or more embodiments. In the embodiment shown, image 901 depicts a native CT scan image/slice for a CT study of a patient's chest. Image 902 depicts an SXR image generated from a corresponding CT volume image after projection in accordance with process 700 (e.g., without any enhancement). For example, with reference to FIG. 7, image 901 can be or correspond to 3D image data 701 and image 902 can be or correspond to synthetic 2D image 716.

With reference again to FIG. 9, image 903 depicts an enhanced SXR image after harmonization, which corresponds to a harmonized version of the image 902. Image 904 depicts a further enhanced SXR image after style translation (e.g., using synthetic to native model 808), which corresponds to a style translated version of image 903. As can be seen by comparison of the respective SXR images 901-903 relative to one another, image 903 corresponding to the harmonized version of image 902 is more realistic XR image relative to the initial output SXR image after projection. In addition, image 904 corresponding to the style translated version of image 903 provides an even more realistic and higher quality SXR image compared to that of the SXR image with only harmonization.

Figure 10:
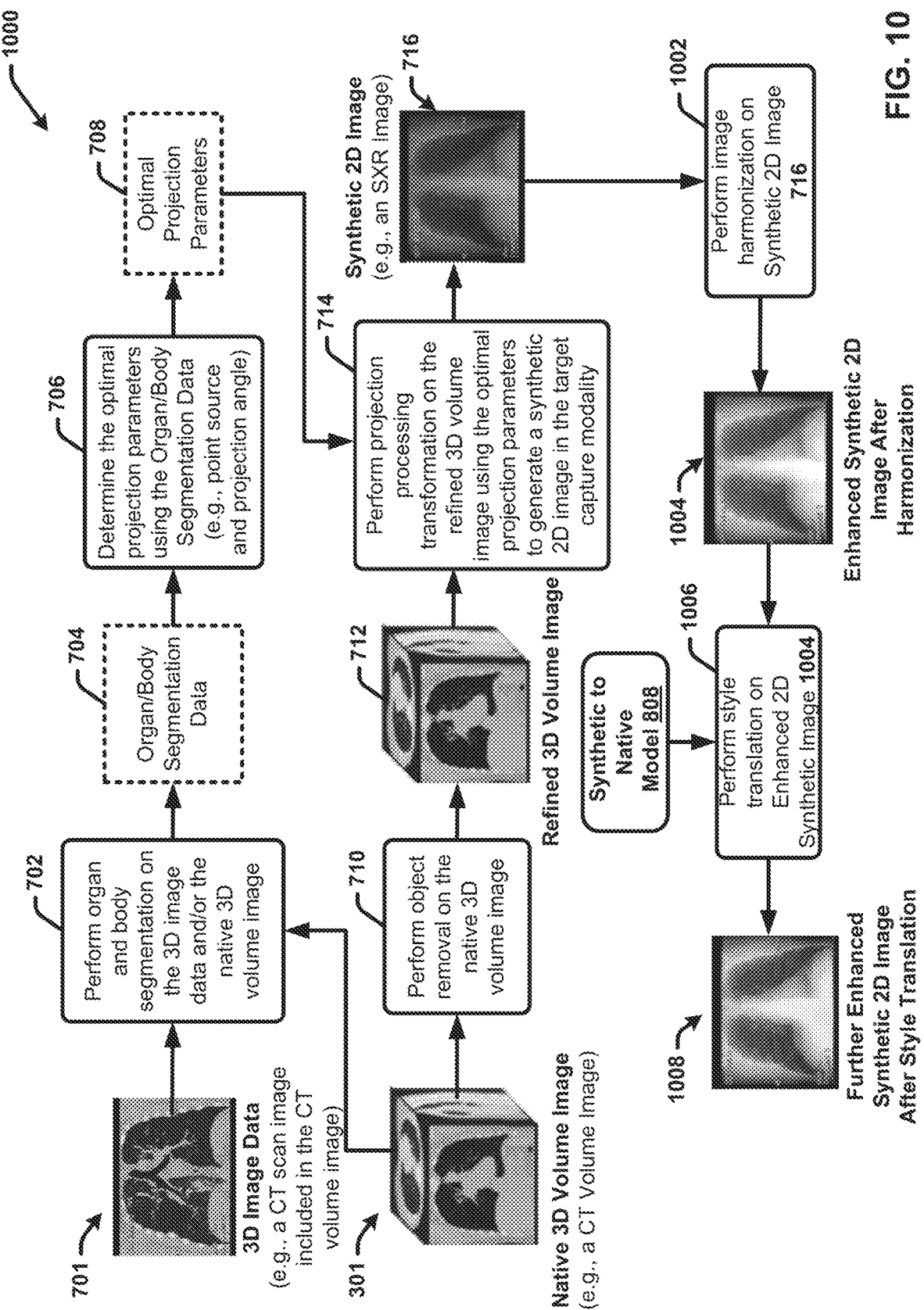
FIG. 10 presents an example process for generating an enhanced synthetic 2D image from a 3D image using projection processing in accordance with one or more embodiments of the disclosed subject matter.

FIG. 10 presents an example process 1000 for generating an enhanced synthetic 2D image from a 3D image using projection processing in accordance with one or more embodiments of the disclosed subject matter. Process 1000 is similar to process 700 with the addition of post-processing enhancement steps. Repetitive description of like elements employed in respective embodiments is omitted for sake of brevity.

In accordance with process 1000, after the initial synthetic 2D image 716 has been generated as described with reference to FIG. 7, at 1002, the harmonization component 804 can perform image harmonization on the synthetic 2D image 716 to generate an enhanced synthetic 2D image 1004 after harmonization (e.g., which can be or correspond to image 903). At 1006, the style translation component 806 an perform style translation on the enhanced synthetic 2D image 1004 using the synthetic to native model 808 to generate an even further enhanced synthetic 2D image 1006 after style translation and harmonization (e.g., which can be or correspond to image 904).

With reference again to FIG. 8, in some implementations in which a paired native 2D image is provided for a 3D image used to generate the corresponding a synthetic 2D image, the registration component 812 can perform image registration to enhance the synthetic 2D image using the corresponding native 2D image. The image registration process involves shifting or morphing the geometry (e.g., shape, size, orientation, FOV, etc.) of the synthetic 2D image to be more similar to that of the corresponding native 2D image. The result of the registration process is a transformation of the synthetic 2D image into a registered synthetic 2D image that is more geometrically similar to that of the corresponding native 2D image. In accordance with the disclosed subject matter, registered synthetic 2D images can also be considered enhanced images and can be included in the enhanced synthetic 2D images 816.

Figure 11:
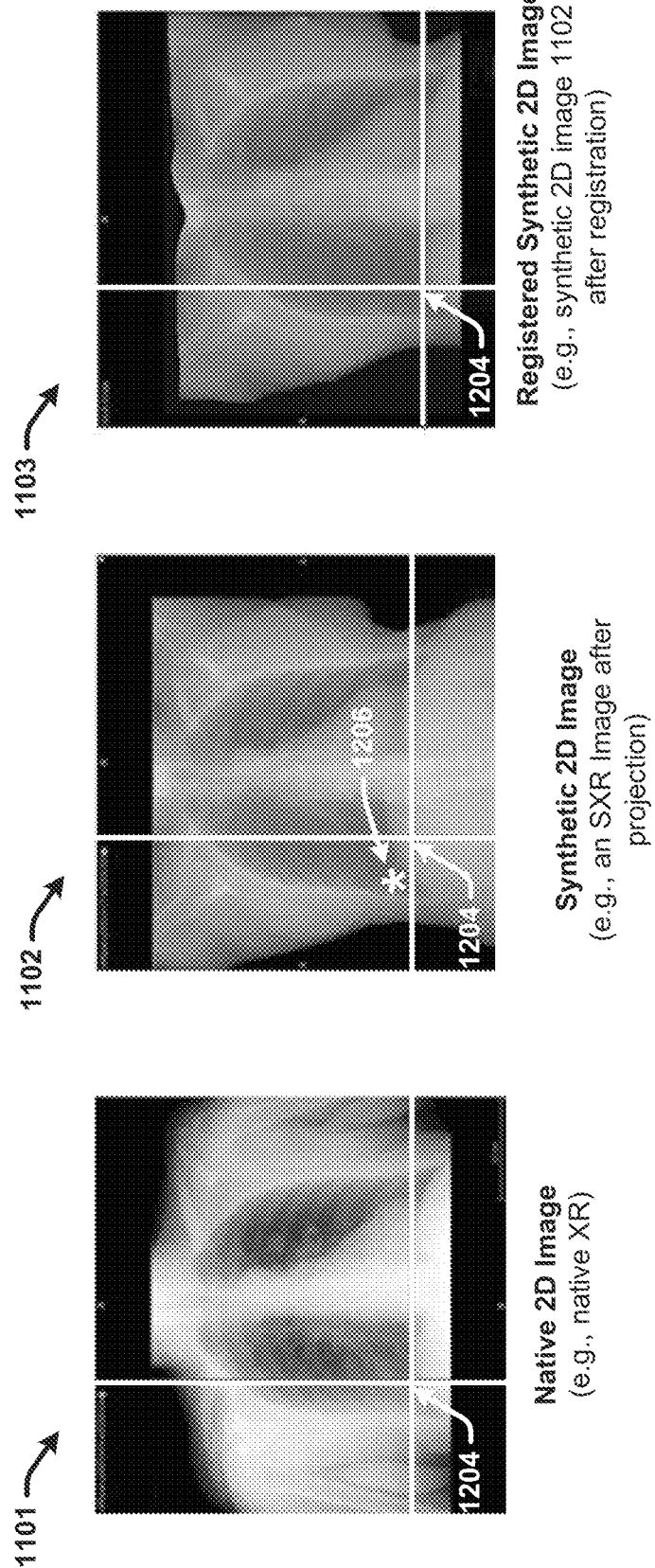
FIG. 11 illustrates image registration in accordance with one or more embodiments of the disclosed subject matter.

FIG. 11 illustrates image registration in accordance with one or more embodiments of the disclosed subject matter. FIG. 11 presents a native 2D image 1101, a synthetic 2D image 1102, and a registered synthetic 2D image 1103. The native 2D image 1101 is a native XR image that was paired with a corresponding 3D image for the same patient capture of the chest in a source 3D modality (e.g., a CT modality) within a 48-hour timeframe. The synthetic 2D image 1102 corresponds to an SXR image generated from the corresponding 3D image by the multimodal training data generation module 800 (or other multimodal training data generation modules disclosed herein) using transformation component 112 and optionally enhancement component 802. For example, the synthetic 2D image 1102 can be or correspond to one of the synthetic 2D images 116, synthetic 2D image 303, synthetic 2D image 502, synthetic 2D image 716, image 903 or image 904.

The registered synthetic 2D image 1103 correspond to a registered version of the synthetic 2D image 1102 after adjustment by the registration component 812 in accordance with an image registration process. In this regard, the registration process can involve adjusting or morphing shape or geometry of the synthetic 2D image 1102 to be more similar to that of the native 2D image 1101 (e.g., moving and cropping, rotating, magnifying, reducing, etc.). In the embodiment shown, white reference lines are used to mark reference position information of reference anatomical features in the native 2D image, which in this example include the border of the baseline of the patient's chest cavity and the right side of the patient's next. In this regard, the vertical reference line in the native 2D image extends along the right side of the patient's neck and intersects at a 90° degree angle with the horizontal reference line at intersection point 1204.

As can be seen by comparison of the same reference lines when applied to the synthetic 2D image 1102, the position of the patient's chest in the image data relative to the reference line intersection point 1204 is off. In particular, it should be shifted further to the left in line with marker 1206 (e.g. as it appears in the native 2D image 1101). In accordance with this example, the registration process can involve moving the position of the synthetic 2D image using the respective reference lines as applied to the native 2D image 1101 as a guide such that the position of the synthetic 2D image 1102 relative to the intersection point 1204 and reference lines is more similar to that of the native 2D image 1101. In accordance with this example, this would involve shifting the synthetic 2D image 1102 slightly downwards and to the right to move the marker position 1206 in the image to the intersection point 1204. The registration process can also involve cropping any excess portion of the synthetic 2D image 1102 that is not present in the native 2D image 1102. As can be seen by comparison of the registered synthetic 2D image 1103 to the synthetic 2D image 1102 and the native 2D image 1101, the registered synthetic 2D image 1103 is much more similar in appearance to the native 2D image 1101 relative to the synthetic 2D image 1102. The specific algorithm or algorithms used for the registration process to register the synthetic 2D image with the native 2D image can vary and include known registration algorithms.

Figure 12:
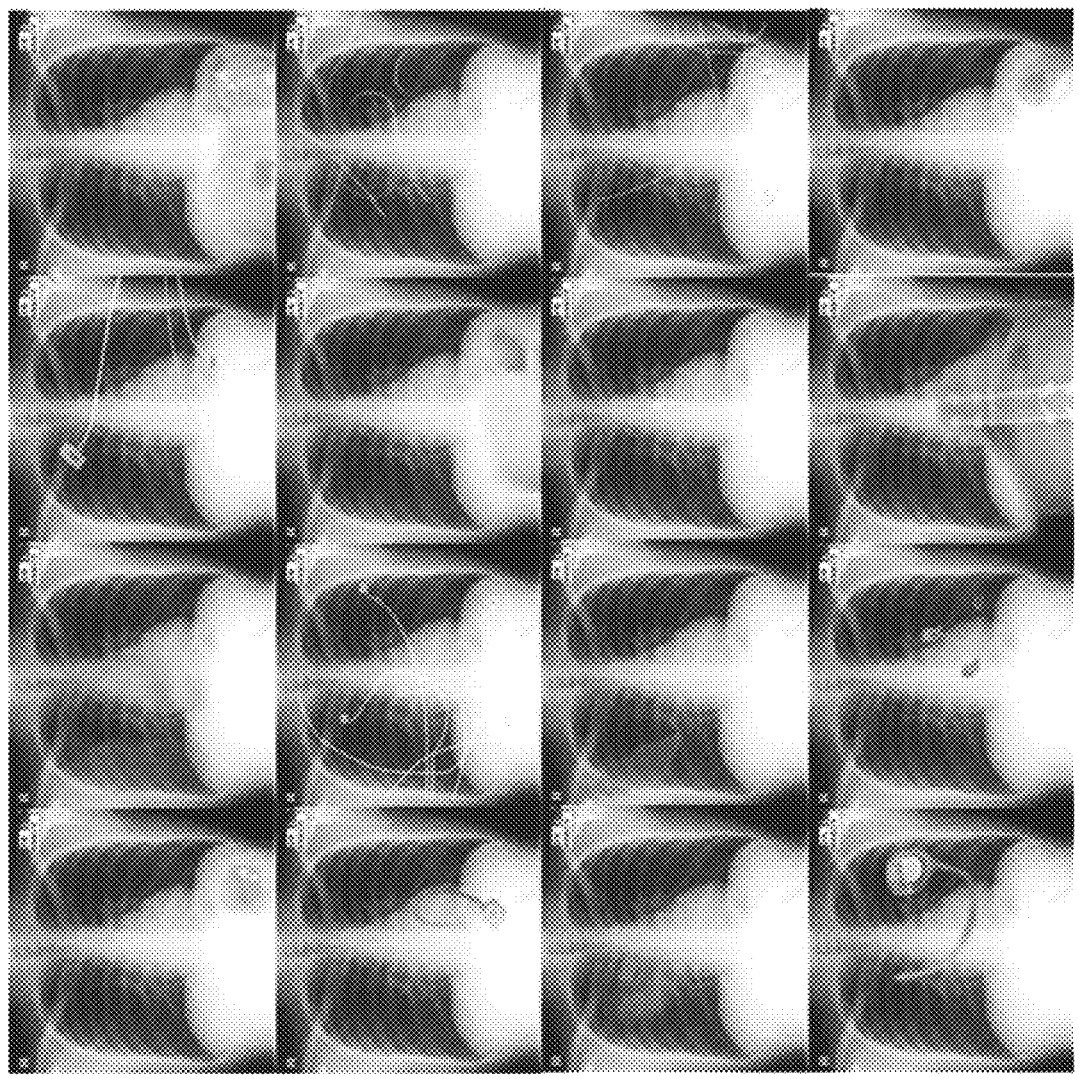
FIG. 12 illustrates generating different synthetic 2D image version with different augmented data transfers in accordance with one or more embodiments of the disclosed subject matter.
Figure 12:
Figure 12:
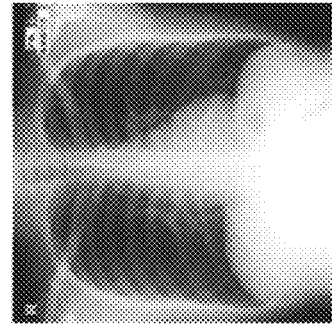

With reference again to FIG. 8, the enhancement component 802 can also include augmentation component 814 to facilitate generating different versions of a synthetic 2D image or an enhanced synthetic 2D image to increase the variety and amount of the synthetic 2D images in the training data 122, as illustrated in FIG. 12.

In this regard, FIG. 12 illustrates generating different synthetic 2D image version with different augmented data transfers in accordance with one or more embodiments of the disclosed subject matter. With reference to FIGS. 8 and 12, the augmentation component 814 can generate multiple copies 1204 of a synthetic 2D image 1202 (or an enhanced synthetic 2D image) and apply various augmented features and/or additional adjustments to the respective copies 1204 to generate variational training data images that are more representative of the different native 2D images that will be encountered in the field (e.g., to simulate different patient data). For example, the augmentation component 814 can transfer known augmented features such implanted medical devices, wires, tubes, cables, stomach gas, pacemaker, scars, empty spaces, metal objects, comorbidities (e.g., masses, fluid-filled regions, etc.) and the like to the different copies of the synthetic 2D image.

In some embodiments, the augmentation component 814 can employ same or similar transfer techniques as the annotation transfer component 114 to accurately transfer these augmented features to the respective copies 1204 (e.g., using optimal and/or selected projection parameters as discussed in greater detail infra). In some implementations, the augmentation component 814 can also modify other visual properties of the respective copies 1204, such as changing the size, gender, position, intensity, border thickness, co-locations, and the like. In accordance with the disclosed subject matter, augmented synthetic 2D images can also be considered enhanced images and can be included in the enhanced synthetic 2D images 816.

With reference again to FIG. 8, it should be appreciated that the enhancement component 802 can perform one or more of the enhancement procedures described above on a same synthetic 2D image to transform it into an enhanced synthetic 2D image. In this regard, in implementations in which a paired native 2D image is provided for a 3D image used to generate the corresponding a synthetic 2D image, the enhancement component 802 enhance the native 2D image using image registration (e.g., via the registration component 812), image harmonization (e.g., via the image harmonization component 804), style translation (e.g., via the style translation component 806), image augmentation (e.g., via augmentation component 814), or a combination thereof. In other implementations in which a paired native 2D image is not available, the enhancement component 802 can still perform image harmonization, style translation and/or augmentation of the synthetic 2D image to transform it into an enhanced synthetic 2D image.

The annotation transfer component 114 can further transfer ground truth data associated with the respective 3D images used to generate the corresponding enhanced synthetic 2D images 816 from the respective 3D images to the corresponding enhanced synthetic 2D images 816 to generate enhanced annotated synthetic 2D images 818. In some implementations, the annotation transfer component 114 can also transfer ground truth data associated with 3D images paired with style translated native 2D images (e.g., using native to synthetic model 110) to the corresponding style translated native 2D images to generate enhanced annotated native 2D images 822. In this regard, discussion of transferring ground truth data to a synthetic 2D image hereinafter assumes the synthetic 2D image can enhanced. The annotation transfer component 114 can also transfer ground truth data associated with the native 2D images (e.g., included in the annotated paired native 2D images 110) to the translated native 2D images to generate enhanced annotated native 2D images 822.

In one or more embodiments, the annotation transfer component 114 can transfer ground truth data associated with a 3D image to a corresponding synthetic 2D image generated or derived therefrom using projection processing. With these embodiments, the projection component 206 can project the ground truth data associated with the 3D image onto the synthetic 2D image to generate projected ground truth data that is spatially and anatomically aligned with the synthetic 2D image. In some implementations in which the synthetic 2D image was generated by the projection component 206 using projection processing (e.g., point source projection or parallel projection), the projection component 206 can generate the projected ground truth data using the same projection process and projection parameters used to generate the synthetic 2D image. The annotation transfer component 114 can then transfer the projected ground truth data to the synthetic 2D image, resulting in an annotated synthetic 2D image.

Figure 13:
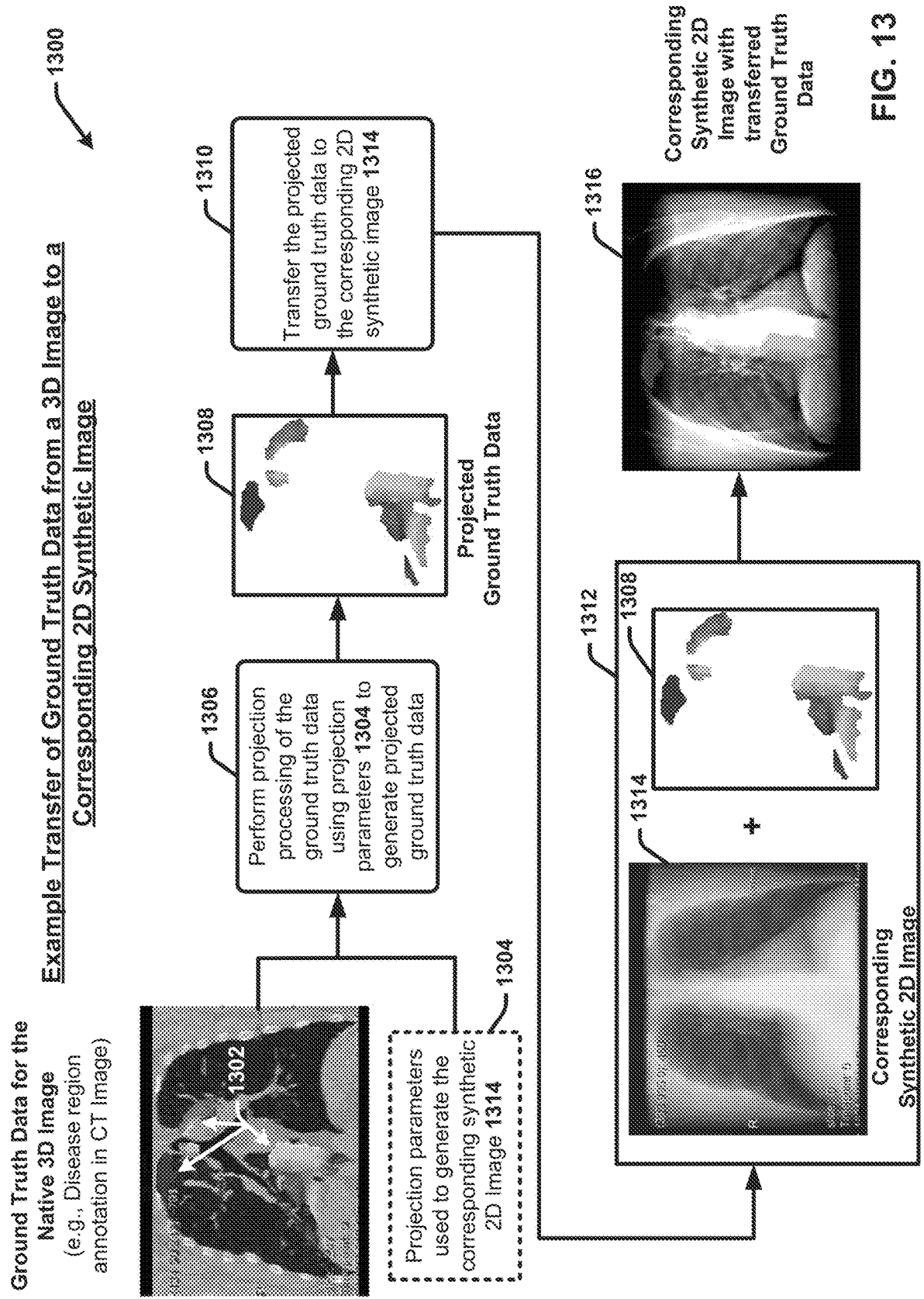
FIG. 13 presents an example process for transferring ground truth data from a 3D image to a corresponding synthetic 2D image in accordance with one or more embodiments of the disclosed subject matter.

FIG. 13 presents an example process 1300 for transferring ground truth data from a native 3D image to a corresponding synthetic 2D image in accordance with one or more embodiments of the disclosed subject matter. In this regard, process 1300 provides an example process that can be performed by the annotation transfer component 114 to generate annotated synthetic 2D images 118 and enhanced annotated synthetic 2D images 818. Repetitive description of like elements employed in respective embodiments are omitted for sake of brevity.

With reference to FIGS. 8 and 13, in accordance with process 1300, the corresponding synthetic 2D image 1304 comprises a SXR image that was generated based on projection of a CT volume image for a patient onto a projection plane using projection processing and the techniques described with reference to the projection component 206. In this regard, the CT volume image can be or correspond to the native 3D image used to generate the corresponding synthetic 2D image 1304. Process 1300 involves transferring ground truth data 1302 for the native 3D image onto the corresponding synthetic 2D image 1304 to generate a corresponding synthetic 2D image 1316 with transferred ground truth data. In the embodiment shown, the ground truth data 1302 for the native 3D image comprises a mask mark-up of the disease region in the lungs as applied to a representative CT image included in the CT volume image (e.g., a CT image used to generate the CT volume image). In other embodiments, the ground truth data can be applied directly to the 3D volume image.

In accordance with process 1300, at 1306, the projection component 206 can perform projection processing of the ground truth data 1302 using projection parameters 1304 to generate projected ground truth data 1308. In this regard, the projection parameters 1304 include the projection parameters used to generate the corresponding synthetic 2D image 1314. For example, the projection parameters 1304 can include the optimal or standard projection parameters as determined by the projection parameter component 608 (e.g., the optimal point source location and projection angle). By using the same projection parameters, the projected ground truth data 1308 will have the correct dimensionality and alignment when applied to the corresponding synthetic 2D image 1304. At 1310, the annotation transfer component 114 can further transfer the projected ground truth data 1308 onto the corresponding synthetic 2D image as shown in box 1312, resulting in the generation of the corresponding synthetic 2D image 1316 with transferred ground truth data. For example, the annotation transfer component 114 can overlay the projected ground truth data 1308 onto the corresponding synthetic 2D image 1314 and generate a copy of the corresponding synthetic 2D image 1316 with the ground truth data applied.

Figure 14:
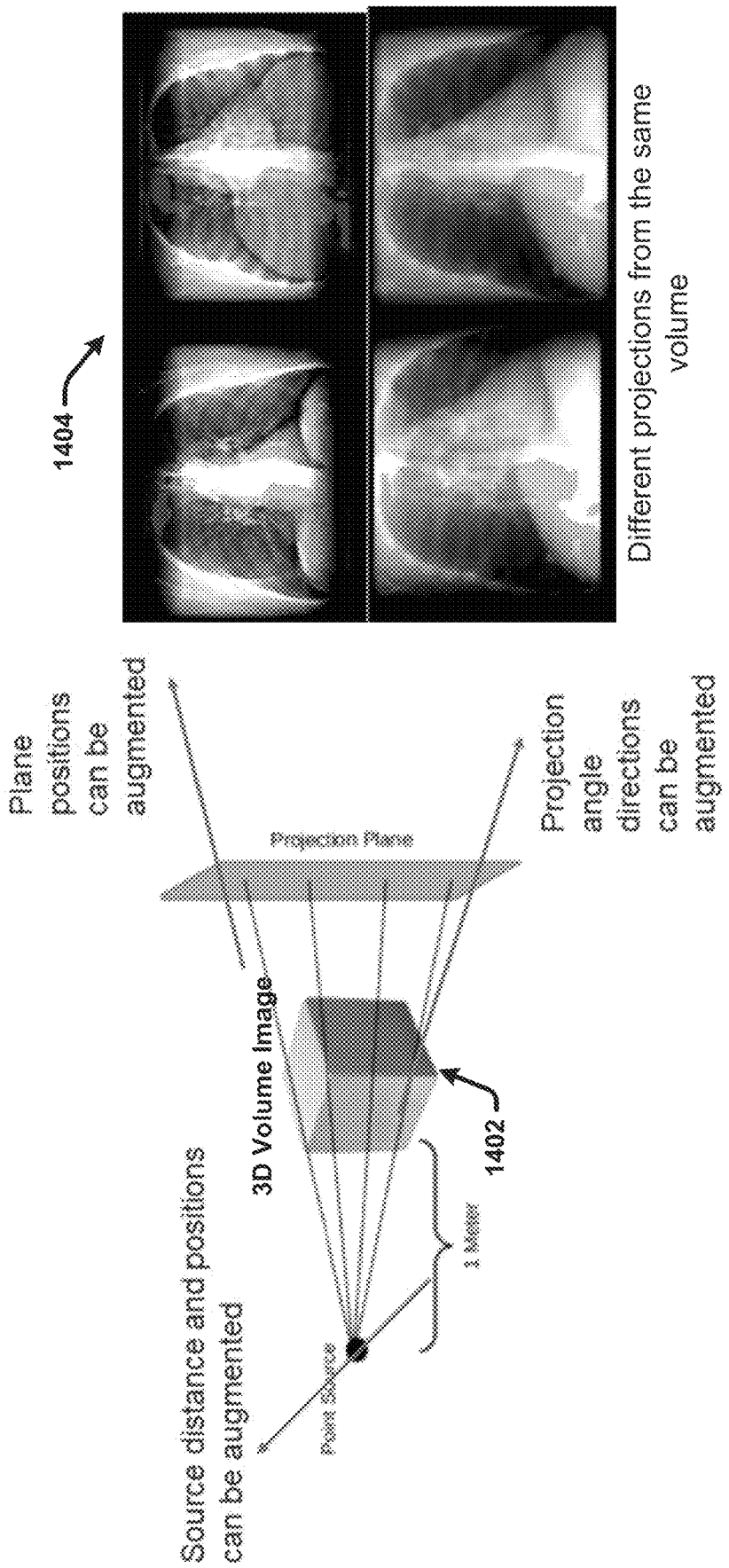
FIG. 14 illustrates generating different synthetic 2D images with ground truth data using different projection parameters in accordance with one or more embodiments of the disclosed subject matter.

FIG. 14 illustrates generating different ground truth marked synthetic 2D images 1402 generated from the same 3D volume image 1402 using different projection parameters in accordance with one or more embodiments of the disclosed subject matter. In the embodiment shown, the images comprise SXR images generated from a CT volume with the corresponding ground truth applied. For example, the respective images can be or correspond to ground truth annotated synthetic 2D image 1316 yet respectively generated with different projection parameters, resulting in different projections from the same volume.

In this regard, with reference to FIGS. 8 and 14, in some embodiments, once the projection parameter component 608 has determined the optimal projection parameters for generating a synthetic 2D image from a 3D image, the parameter projection component 608 can augment or adjust the projection parameters around the optimal projection parameters to generate as many as possible projections to further boost the number of synthetic 2D images with corresponding ground-truth. For example, as applied to point source projection, the projection parameter component 608 can slightly adjust one or more projection parameters, including but not limited to: the point source distance and position, the projection plan position, and the projection angle. In this regard, the parameter projection component 608 can generate different sets of projection parameters from the optimal projection parameters. The projection component 206 can further generate different synthetic 2D images and corresponding projected ground truth data from the same 3D volume using the different sets of projection parameters. The annotation transfer component 114 can further transfer the projected ground truth data generated for the different synthetic 2D using the different synthetic 2D images thereto (e.g., in accordance with process 1300) to generate different ground truth annotated synthetic 2D images from the same 3D volume, as shown in FIG. 14.

Figure 15:
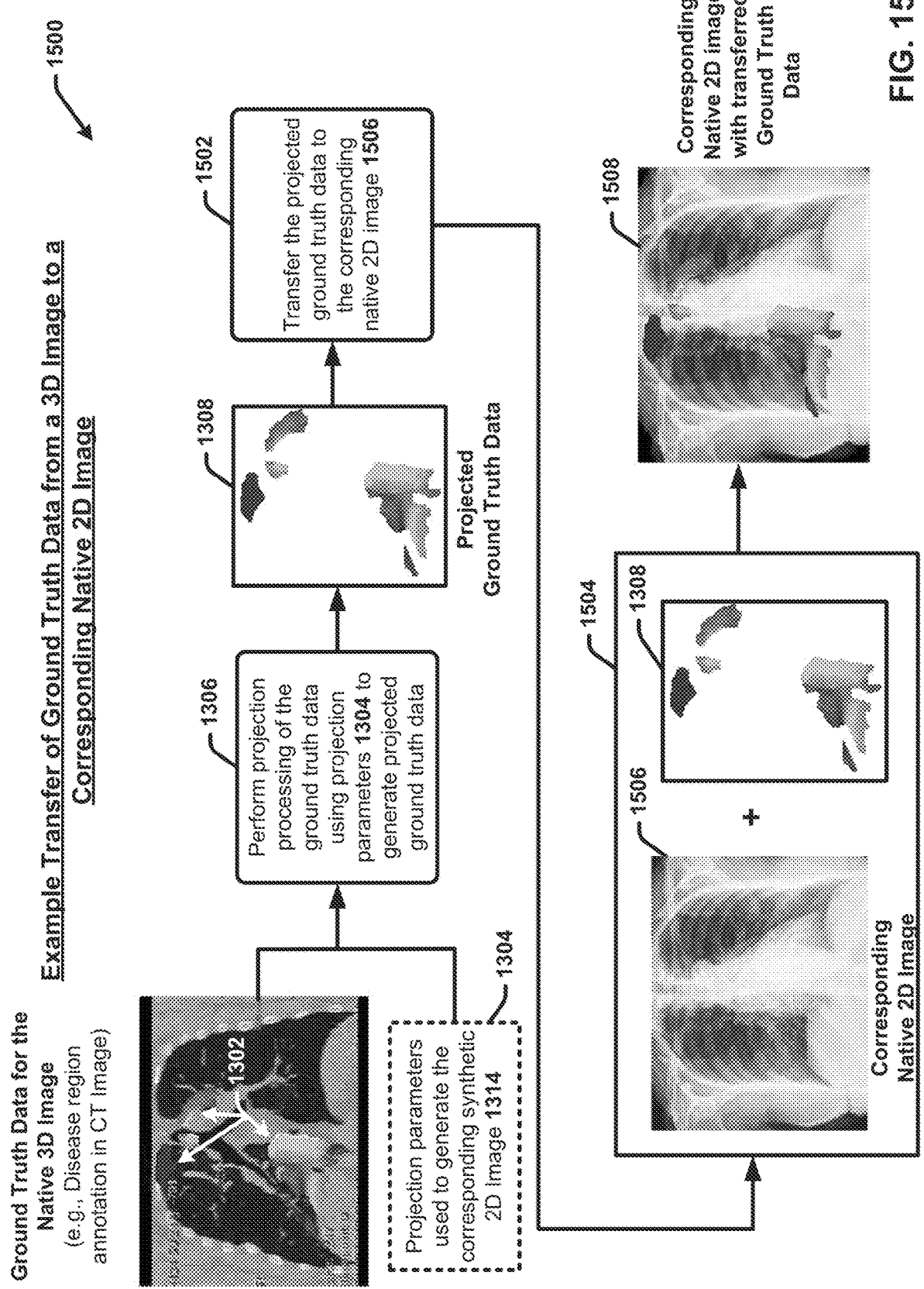
FIG. 15 presents an example process for transferring ground truth data from a 3D image to a corresponding native 2D image in accordance with one or more embodiments of the disclosed subject matter.

FIG. 15 presents an example process 1500 for transferring ground truth data from a 3D image to a corresponding native 2D image in accordance with one or more embodiments of the disclosed subject matter. In this regard, process 1500 provides an example process that can be performed by the annotation transfer component 114 to generate annotated native 2D images 120. Repetitive description of like elements employed in respective embodiments are omitted for sake of brevity.

With reference to FIGS. 8 and 15, in some embodiments in which a paired native 2D image is provided for a 3D image used to generate a corresponding synthetic 2D image, the annotation transfer component 114 can transfer annotation data thereto from the 3D image using the same projection parameters used to generate the corresponding synthetic 2D image. In this regard, the process for transferring annotation data associated with a 3D image to a paired native 2D image can be substantially the same as the process for transferring the annotation data to a synthetic 2D image generated or derived from the 3D image.

For example, process 1500 is substantially the same as process 1300 with the difference being that the projected ground truth data 1308 is transferred to the corresponding native 2D image 1506 as opposed to the corresponding synthetic 2D image 1314. In this regard, process 1300 can involve generating the projected ground truth data 1308 in the same manner as process 1300. At 1502, the annotation transfer component 114 can further transfer the projected ground truth data 1308 onto the corresponding native 2D image 1506 as shown in box 1504, resulting in the generation of the corresponding native 2D image 1508 with transferred ground truth data. For example, the annotation transfer component 114 can overlay the projected ground truth data 1308 onto the corresponding native 2D image 1506 and generate a copy of the corresponding native 2D image 1508 with the ground truth data applied.

In other embodiments in which a paired native 2D image is provided for a 3D image used to generate a corresponding synthetic 2D image, the paired native 2D image can be used to determine the optimal projection parameters, as described below with reference to FIGS. 16-20.

Figure 16:
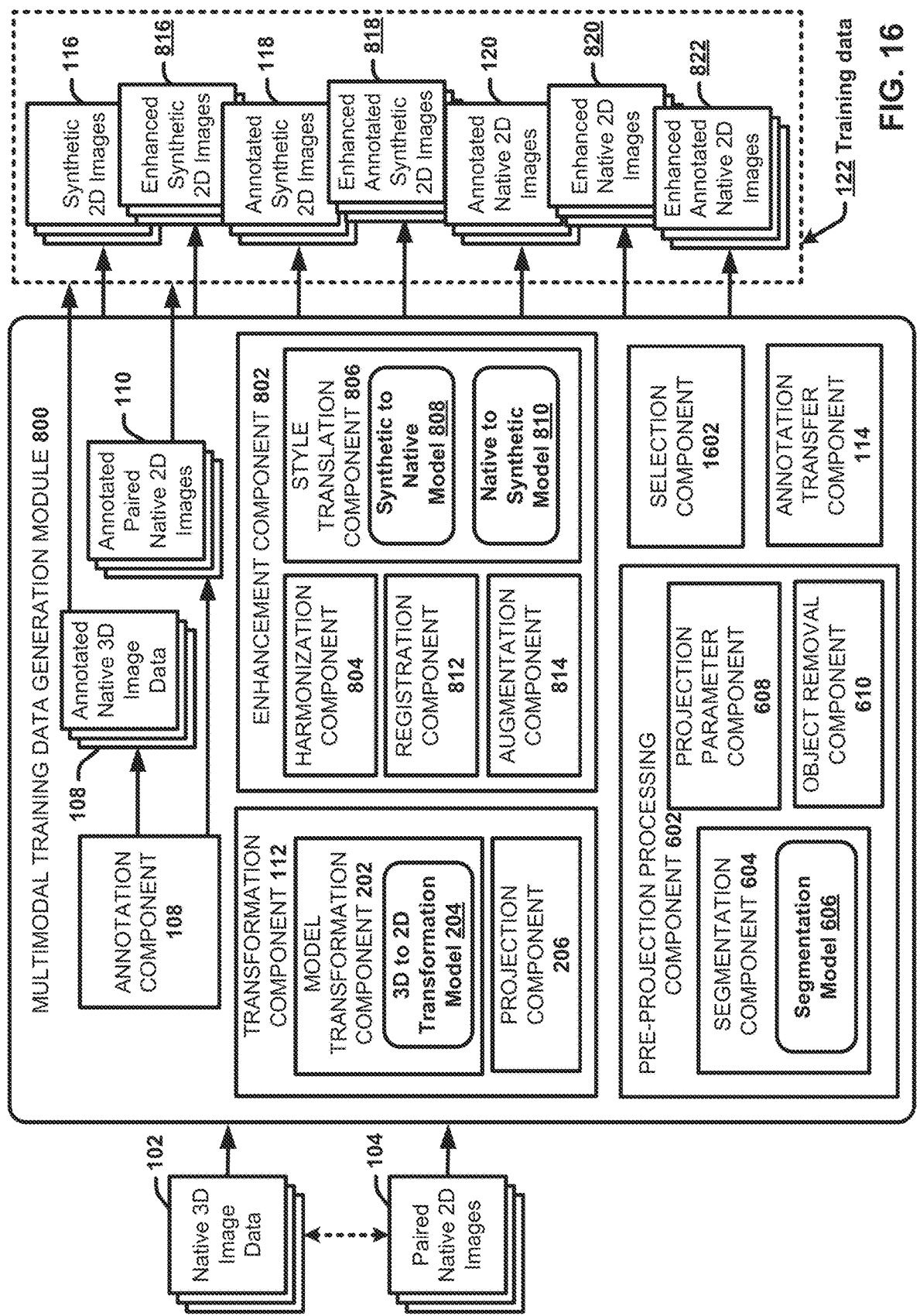
FIG. 16 presents another example multimodal training data generation module in accordance with one or more embodiments of the disclosed subject matter

FIG. 16 presents another example multimodal training data generation module 1600 in accordance with one or more embodiments of the disclosed subject matter. Multimodal training data generation module 1600 can include same or similar features and functionalities as multimodal training data generation module 800 with the addition of selection component 1602. Repetitive description of like elements employed in respective embodiments is omitted for sake of brevity.

In some embodiments in which a paired native 2D image is provided for a 3D image, the projection component 206 can generate a plurality of different candidate synthetic 2D images using different projection parameters. In particular, the projection parameter component 608 can generate different sets of candidate projection parameters randomly and/or with some predefined constraints (e.g., predefined ranges for possible projection parameter values). The projection component 206 can further project the 3D image using the different sets of projection parameters to generate different candidate synthetic 2D images respectively corresponding to 2D versions of the 3D image in the second capture modality.

Figure 17:
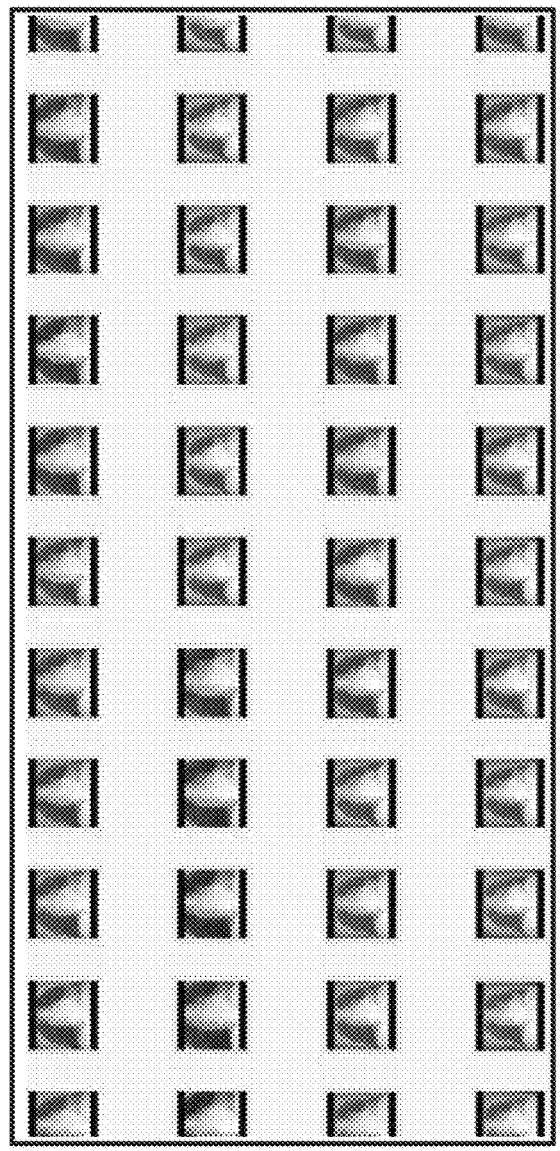
FIG. 17 presents different SXR images and corresponding masks generated from a same 3D image using different projection parameters in accordance with one or more embodiments of the disclosed subject matter.
Figure 17:
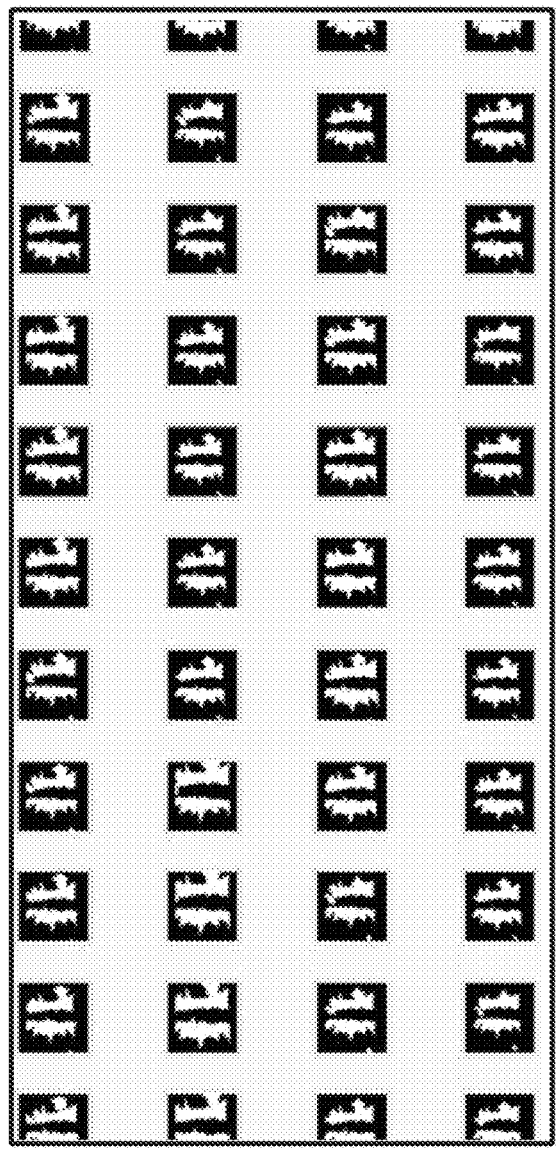

For example, FIG. 17 presents different candidate SXR images 1702 and corresponding projected masks 1704 generated from a same 3D image using different projection parameters in accordance with one or more embodiments of the disclosed subject matter. In accordance with this example implementation, for each set of candidate projection parameters, the projection component 206 can employ the 3D volume image and its associated ground truth data to generate a corresponding SXR and projected ground truth data, which in this case is a lung segmentation mask.

With reference to FIGS. 16 and 17, the selection component 1602 can further compare the different candidate synthetic 2D images to the paired native 2D image using one or more similarity evaluation metrics to identify and select the best candidate synthetic 2D image that provides the closest match to the native 2D image. In this regard, the selection component 1602 can identify and select one of the candidate synthetic 2D images that most closely matches the appearance and geometry of the native 2D image. For instance, in accordance with the example shown in FIG. 17, the selection component can select one of the candidate SXR images 1702 that best matches the paired native 2D image. The similarity metrics used and the manner in which the selection component 1602 generates the similarity values for the metrics can vary. In some implementations, the similarity metrics can include a structural similarity index metric, a mutual information metric or the like. The selection component 1602 can also employ one or more ML models configured to compare respective images and generate similarity scores for the pairs using one or more similarity metrics/criteria.

In some implementations of these embodiments, the registration component 812 can register the different candidate synthetic 2D images with the native 2D image prior to the comparison to facilitate determining the closest match. As discussed with reference to FIG. 11, this registration results in transformation of the candidate synthetic 2D images into registered synthetic 2D images.

Figure 18:
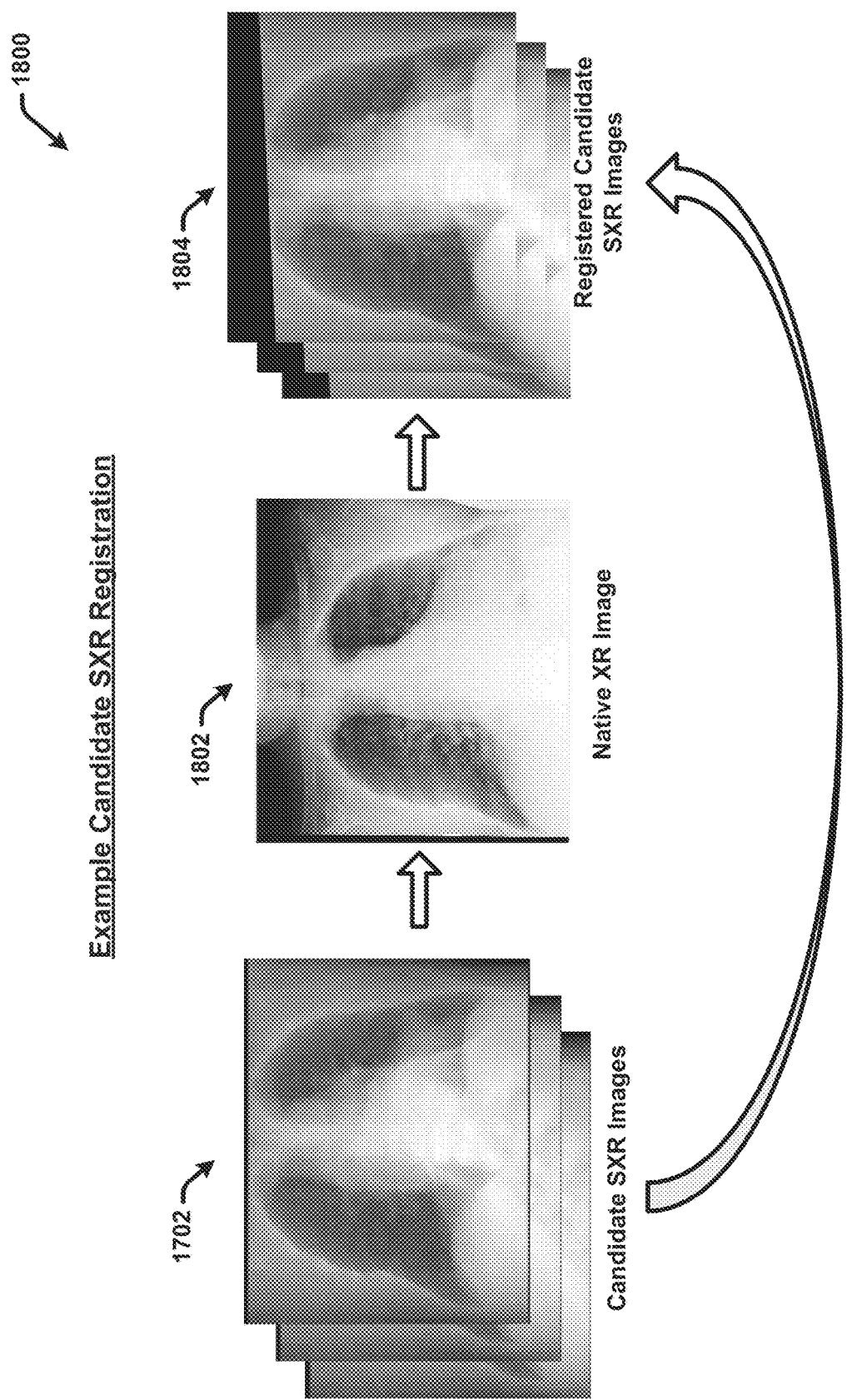
FIG. 18 illustrates registration of candidate SXR images with a corresponding native XR in accordance with one or more embodiments of the disclosed subject matter.

For example, FIG. 18 illustrates registration of the candidate SXR images 1702 with a corresponding native XR image 1802 in accordance with one or more embodiments of the disclosed subject matter. In the embodiment shown, each of the candidate SXR images 1702 can be registered with the native XR image 1802 to transform them into registered candidate SXR images 1804. With this example, the XR image 1802 is the paired native 2D image for the 3D image (e.g., a CT volume image) used to generate the respective candidate SXR images 1702, wherein the XR image 1802 and the 3D image were capture of the same patient and the same anatomical region, both showing the same medical condition in a same or similar state (e.g., within 48 hours for fast moving disease).

Once the best matching candidate synthetic 2D image has been selected, the projection parameter component 608 can obtain the set of projection parameters used to generate the best matching candidate synthetic 2D image. This set of projection parameters can then be used to transfer ground truth data associated with the 3D image to the native 2D image and/or the selected synthetic 2D image. For example, in accordance with the example embodiment shown in FIG. 17, the projection mask generated for the best matching candidate synthetic image included amongst the projection masks 1704 can be selected and transferred to the native 2D image. These projection parameters can also be used as the optimal or baseline projection parameters from which the projection parameter component 608 can adjust the projection parameters to generate additional synthetic 2D images in accordance with the techniques described with reference to FIG. 14.

Figure 19A:
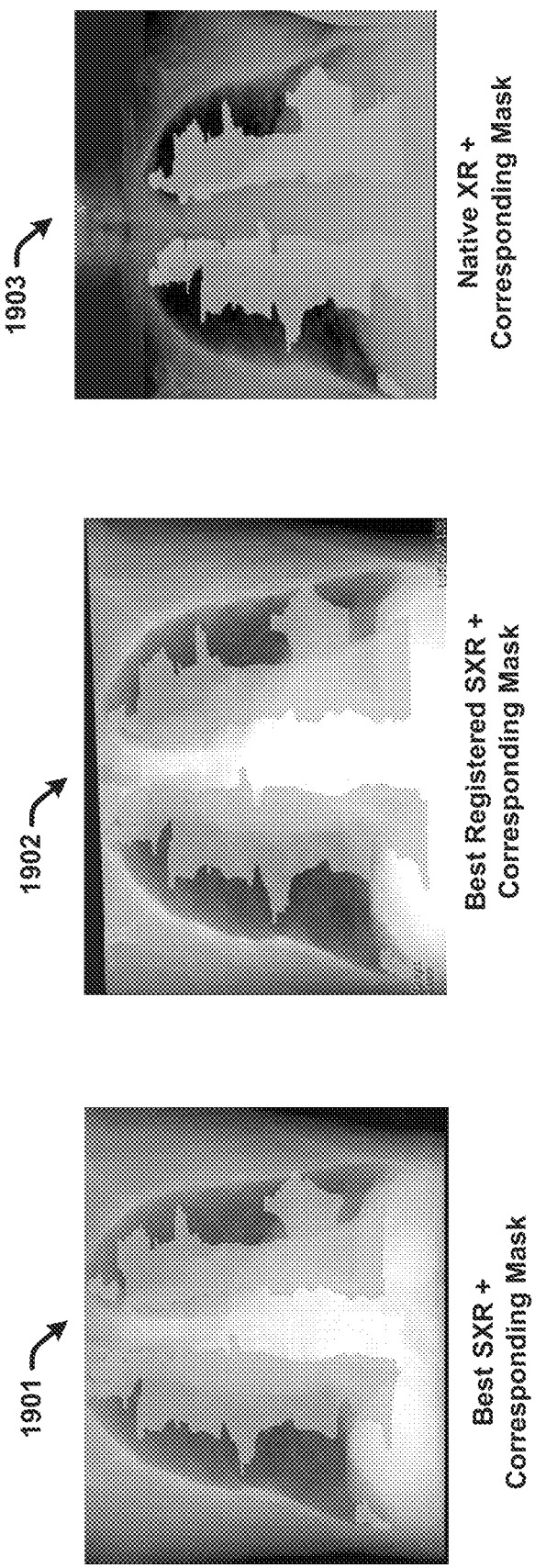
FIG. 19A presents images of the best match SXR, the registered best match SXR and the corresponding native XR with transferred masks in accordance with one or more embodiments of the disclosed subject matter.
Figure 19B:
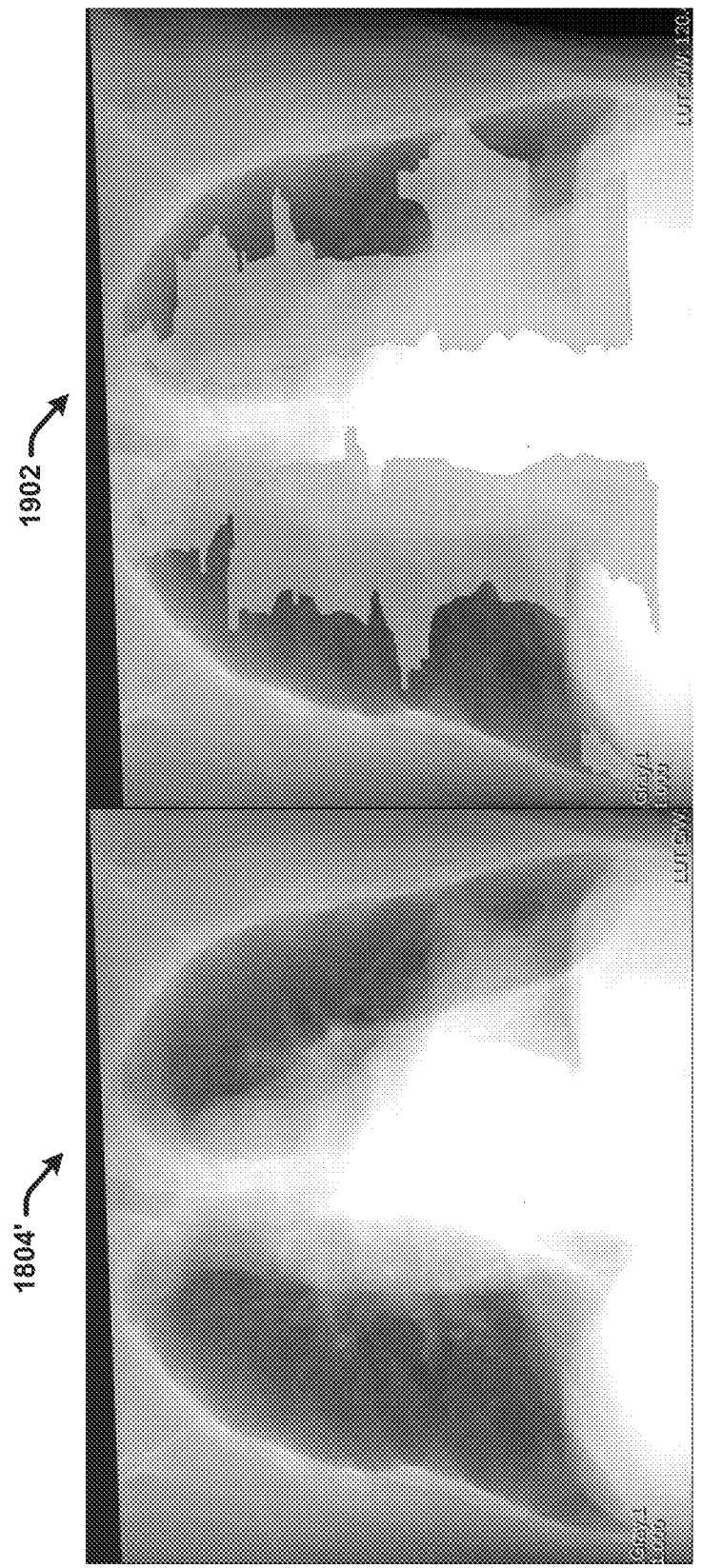
FIG. 19B presents comparative images of the best registered SXR with and without the transferred mask in accordance with one or more embodiments of the disclosed subject matter.
Figure 19C:
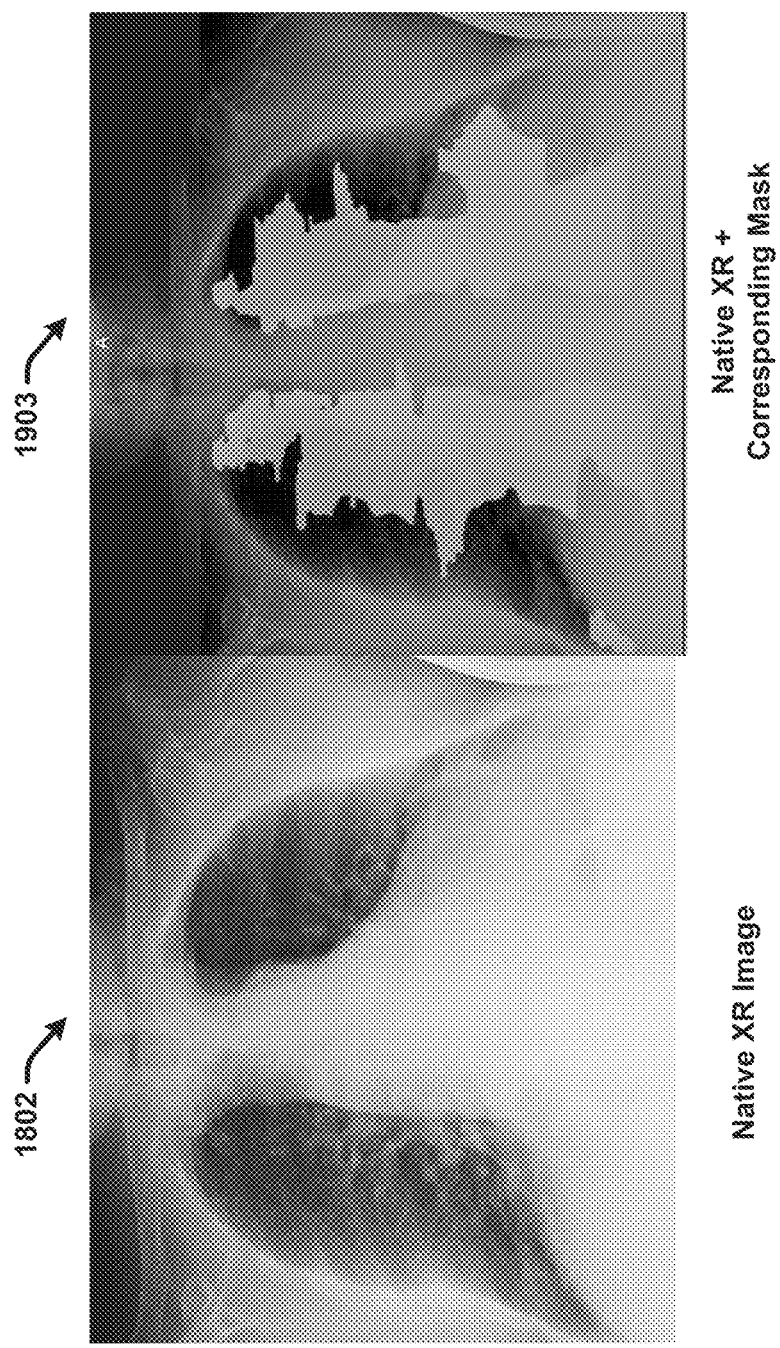
FIG. 19C presents comparative images of the native XR with and without the transferred mask in accordance with one or more embodiments of the disclosed subject matter.

FIGS. 19A-19C present the results of different mask transfers in association with registration and selection of the best matching candidate SXR and its corresponding mask in accordance with the example implementations demonstrated in FIGS. 17 and 18.

With reference to FIG. 19A, image 1901 presents best match SXR image prior to registration (e.g., selected from the candidate SXR images 1702) with its transferred projection mask. Image 1902, presents the best match the registered best match SXR image (e.g., selected from the registered candidate SXR images 1804) with the corresponding projection mask applied. Image 1903 presents the native XR image (e.g., XR image 802) with the corresponding projection mask applied thereto. In accordance with this example, the mask applied to each of the images are the same projection mask that was generated for the best matching SXR image selected from the projection masks 1704. As can be seen by comparison of image 1901 to image 1902, the transferred mask fits the registered SXR image better than the unregistered SXR image. In addition, the transferred mask accurately fits the native XR image, demonstrating how the disclosed techniques can be used to accurately transfer ground truth data from a 3D image to a corresponding native 2D image.

FIG. 19B presents comparative images of the best registered SXR 1804' (e.g., selected from the registered candidate SXR images 1804) with and without the transferred mask in accordance with one or more embodiments of the disclosed subject matter.

FIG. 19C presents comparative images of the native XR image 1802 with and without the transferred mask in accordance with one or more embodiments of the disclosed subject matter.

Figure 20:
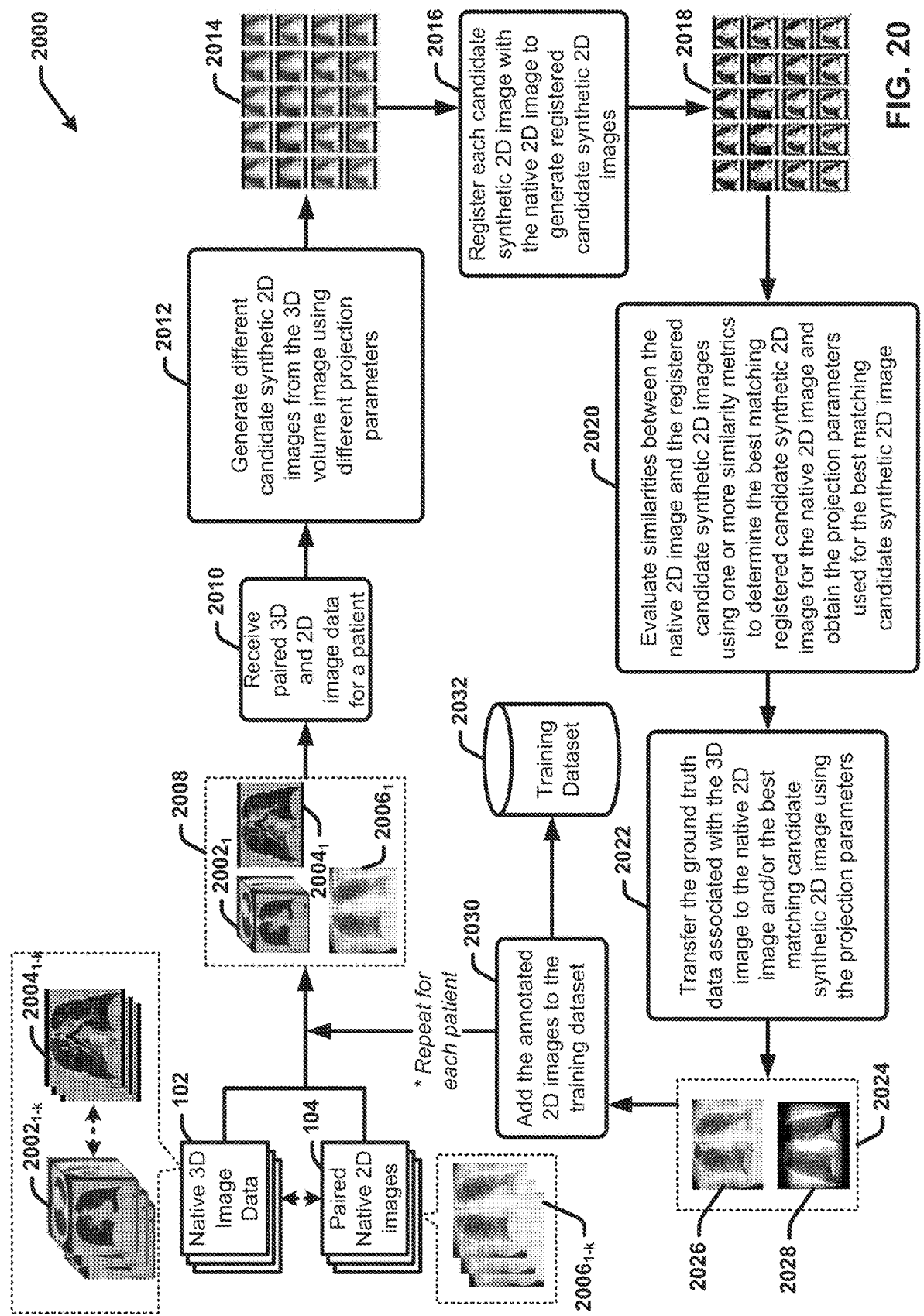
FIG. 20 presents an example process for transferring ground truth data from paired 3D modality volumes to 2D modality images for further modelling in accordance with one or more embodiments of the disclosed subject matter.

FIG. 20 presents an example process 2000 for transferring ground truth data from paired 3D modality volumes to 2D modality images for further modelling in accordance with one or more embodiments of the disclosed subject matter.

In accordance with process 2000 the multimodal training data generation module 1600 can facilitate training a multimodal image analysis network for a medical condition manifested in an anatomical region using multimodal image data including paired 3D images from a first modality and native 2D images $2006_{1-k}$ from a second modality of a number of patients 1-*k*, wherein each image pair corresponds to images acquired of the anatomic region with a similar state of at least one medical condition of the patient. The 3D image for each pair can be provided in the native 3D image data 102 and the 2D image for each pair can be provided in the paired native 2D image data. In the embodiment shown, the native 3D image data 102 can include 3D volume images $2002_{1-k}$ (e.g., CT volume images) and the corresponding scan images $2004_{1-k}$ (e.g., CT scan images) used to generate the corresponding volume images. Thus, paired 3D and 2D data 2008 for each patient 1-*k* can include a 3D volume image $2002_1$, its corresponding scan images $2004_1$, and a corresponding native $2006_1$.

In one or more embodiments, at 2010, the multimodal training data generation module 1600 can receive paired 3D and 3D image data 2008 for a patient. At 2012, the projection component 206 can generate different candidate synthetic 2D images from the 3D volume image $2002_1$ using different projection parameters, resulting in candidate synthetic 2D images 2014. At 2016, the registration component 812 can register each candidate synthetic 2D image with the native 2D image $2006_1$ to generate registered candidate synthetic 2D images 2018. At 2020, the selection component 1602 can evaluate similarities between the native 2D image and the registered candidate synthetic 2D images using one or more similarity metrics to determine the best matching registered candidate synthetic 2D image for the native 2D image. The projection component 206 can further obtain the projection parameters used for the best matching synthetic 2D image.

At 2022, the annotation transfer component 114 can transfer the ground truth data associated with the 3D image to the native 2D image and/or the best matching candidate synthetic 2D image using the projection parameters. This results in generation of annotated 2D image data 2024 in the target capture modality. For example, image 2026 corresponds to the annotated native 2D image and image 2028 corresponds to the annotated synthetic 2D image. At 2030, the multimodal training data generation module 1600 can add the annotated 2D image data 2024 to a training dataset 2032.

Process 2000 can be repeated for each patient for all the paired images from all the patients to obtain a high-quality, annotated images of the second modality and the resulting annotated synthetic and/or native 2D imaged data can be added to a training dataset 2303. The training module 124 can further employ the high-quality annotated images or derived images of the second modality included in the training dataset along with the first modality to enable multi-modal models for classification/triaging, segmentation and quantification.

Figure 21A:
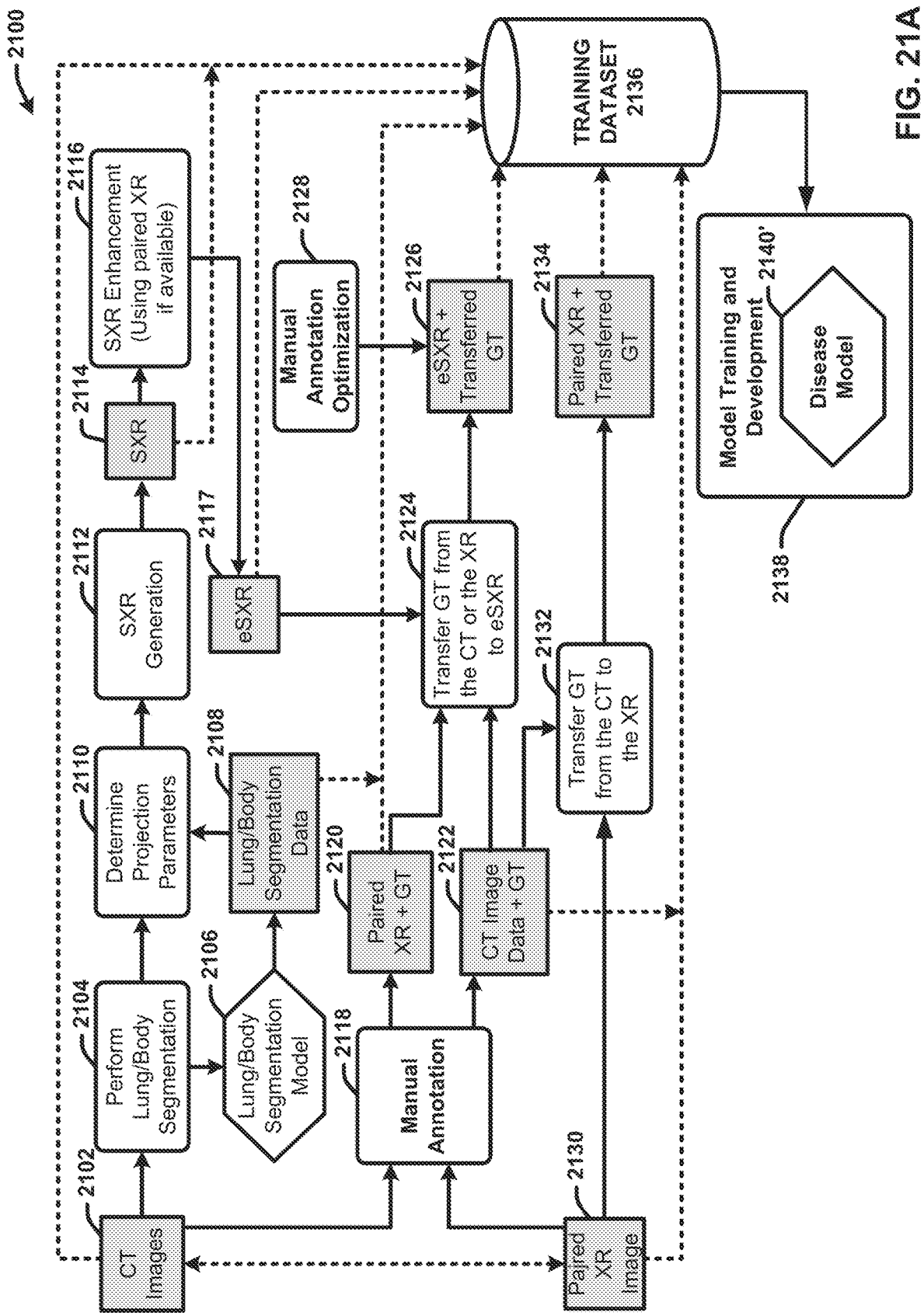
FIG. 21A presents an example multimodal framework for medical image model training and deployment using multimodal input images in accordance with one or more embodiments of the disclosed subject matter.

FIG. 21A presents an example multimodal framework 2100 for medical image model training and deployment using multimodal input images in accordance with one or more embodiments of the disclosed subject matter. Multimodal framework 2100 presents an example framework that can be employed by one or more of the multimodal training data generation modules disclosed herein to generate high-quality annotated medical image training data (e.g., training data 122) using medical image data depicting a same anatomical region and medical condition yet captured using different modalities, including 2D and 3D modalities.

Multimodal framework 2100 is demonstrated wherein the different capture modalities include a CT modality and an XR modality and wherein the respective images depict a patient's chest in association with a manifested respiratory disease. However, it should be appreciated that the anatomical region and the type of medical condition evaluated can vary. In addition, the multimodal input images are not limited to CT and XR modality images and can include other 3D and 2D medical imaging modalities.

In accordance with multimodal framework 2100, the input image data comprises CT images 2102 and a paired XR image 2130 for the CT images, wherein the respective images were captured for a single patient within a timeframe such that the state of the medical condition (e.g., respiratory disease) has not significantly changed. For example, in implementations in which the medical condition is fast moving disease such as pneumonia caused by COVID-19, the preferred time is within 48 hours and more preferably within 24 hours. It should be appreciated however that multimodal framework 2100 can be applied to corresponding image data captured for a plurality of patients to generate a plurality of corresponding training data.

In various implementations, the CT images 2102 can include a CT volume image generated from a plurality of CT images captured during a CT imaging study of the patient. In some implementations, the CT images 2102 can additionally or alternatively include one or more of the plurality of CT image (e.g., one or more representative 2D CT scan images).

In accordance with embodiments in which a paired XR image 2130 is provided for the CT images 2102 as depicted in FIG. 21A, the multimodal framework 2100 can process both the CT images 2102 and the paired XR image 21 in parallel, using both images to generate the training data. However, multimodal framework 2100 can also be applied to only XR data for a patient and only CT data for a patient in implementations in which paired XR and CT image data for the patient is not available.

With reference to the CT image processing pathway, at 2104, lung and body segmentation can be applied to one or more of the CT images 2102 (e.g., via segmentation component 604) using a lung/body segmentation model 2106 to generate lung/body segmentation data 2108. For example, the lung/body segmentation data 2108 can include image data that segments the lungs from the reset of the body in the one or more CT images and or corresponding information that defines the relative geometry of the lungs and spatial location of the lungs in the body (e.g., relative to the front/back body, etc.) as appearing in the CT image data. At 2110, the optimal projection parameters can be determined (e.g., via the projection parameter component 608) using the lung/body segmentation data 2108. Additionally, or alternatively, the optimal projection parameters can be determined using a plurality of candidate SXRs and the paired XR image 2130 and process 2000.

At 2112, SXR generation can be performed (e.g., via the projection component 206) using the projection processing of the CT volume image (e.g., wherein the CT images 2102 include the CT volume image) and the optimal projection parameters to generate an SXR image 2114 (e.g., as described with reference to FIG. 7. Additionally, or alternatively, a plurality of SXR images can be generated as described with reference to FIG. 14. At 2116, one or more SXR enhancement procedures can be applied to the SXR image 2114 (e.g., via the enhancement component 802), as described with reference to FIGS. 8-12, resulting in generation of an enhanced SXR (eSXR) image 2117. In implementations in which the paired XR image 2130 is provided, the paired XR image 2130 can be used for the enhancement (e.g., as the reference image for harmonization and for SXR registration).

At 2124, ground truth (GT) data can be transferred to the eSXR image 2117 (e.g., via the annotation transfer component 114). In the embodiment shown, this can include transferring GT data from the CT image data to the eSXR image 2117 or GT data from the paired XR image 2130 to the eSXR image 2117. The type of the GT information transferred can vary. For example, in some embodiments, the GT data can include mark-up image data applied to the CT image data and transferred to the eSXR image 2117 using the same projection parameters used to generate the eSXR image 2117. For instance, the mark-up image data can include masks or boundary marks identifying specific disease regions, specific organs of interest, measurement data, or the like. The GT data can also include metadata associated with the CT image that describes a radiologist's interpretation of various relevant attributes or features in the image data for training a medical image inferencing model to automatically identify or determine. For example, in various embodiments, the GT metadata can include classification information that classifies a disease in the image data as being present or absent, a valuation of the severity of the disease, or the like.

In accordance with multimodal framework 2100, this GT data can be manually applied at 2118. In this regard, in some embodiments, at 2118, the one or more CT images 2102 (e.g., the CT volume image and/or a representative 2D CT scan slice) can be manually annotated with GT data (e.g., as facilitated by the annotation component 106). The resulting CT image data with the ground truth data applied thereto is represented in FIG. 21A as CT image data+GT 2122. With these embodiments, at 2124, the CT image data+GT 2122 can be transferred to the eSXR image 2117 to generate an annotated eSXR image with the GT data applied thereto, represented in FIG. 21A as eSXR+transferred GT 2126. In other embodiments, at 2118, the paired XR image 2130 can be manually annotated with GT data (e.g., as facilitated by the annotation component 106). The resulting native XR image with the ground truth data applied thereto is represented in FIG. 21A as paired XR+GT 2120. With these embodiments, at 2124, the paired XR+GT 2120 can be transferred to the eSXR image 2117 to generate the annotated eSXR image with the GT data applied thereto, that is, eSXR+transferred GT 2126.

In the embodiment shown, at 2128, the eSXR image 2117 with the transferred GT applied thereto (i.e., eSXR+transferred GT 2126) can (optionally) be manually reviewed and revised as needed. In this regard, the annotation component 106 can present the eSXR image with the transferred GT to one or more annotators for manual review and adjustment. In some embodiments, the annotation component 106 can present the eSXR image with the GT applied thereto to one or more annotators for review based on the difference in capture time between the CT images 2102 and the paired XR image 2130 (e.g., as determined based on timestamp data associated with the respective images) exceeding a threshold time difference (e.g., 24 hours, 48 hours, etc.). The threshold time difference can vary based on the disease/medical condition being evaluated (e.g., shorter for fast changing disease such as pneumonia relative to evaluation of broken bone for example).

In some embodiments (e.g., in which the paired XR image is not manually annotated), at 2132, the CT image data+GT 2122 can be transferred to the paired XR image 2130 to generate an annotated XR image with the GT data applied thereto, represented in FIG. 21A as paired XR+transferred GT 2134. With these embodiments, at 2128, the annotated XR image with the GT data applied thereto (i.e., paired XR+transferred GT 2134) can also (optionally) be manually reviewed and revised as needed. In this regard, the annotation component 106 can present the XR image with the transferred GT to one or more annotators for manual review and adjustment. In some embodiments, the annotation component 106 can present the XR image with the GT applied thereto to one or more annotators for review based on the difference in capture time between the CT images 2102 and the paired XR image 2130 (e.g., as determined based on timestamp data associated with the respective images) exceeding a threshold time difference (e.g., 24 hours, 48 hours, etc.). The threshold time difference can vary based on the disease/medical condition being evaluated (e.g., shorter for fast changing disease such as pneumonia relative to evaluation of broken bone for example).

In accordance with multimodal framework 2100, all of the image data represented in grey boxes can be added to a training dataset 2136. At 2138, the training data included in the training dataset 2136 can further be used to train and develop a disease model 2140' (or another medical image inferencing model). The type of the disease model can vary. For example, in some implementations, the disease model 2140' can include a model configured to classify presence or absence of a medical condition (e.g., pneumonia) in an input medical image. In other implementations, the disease model 2140' can include a model configured segment or mark a disease region depicted in an input image. In various embodiments, the disease model 2140' can be trained to process XR image data as opposed to CT image data, demonstrating how multimodal framework 2100 can employ multimodality image data (e.g., 2D and 3D image data) to generate mono-modality training data (e.g., 2D) that can be used to train and develop a mono-modality inferencing model (e.g., 2D). In the embodiment shown, the asterisk is used for the disease model reference numeral 2140' to indicate that the model is undergoing training and development. In various implementations, the disease model 2140' can be or include a disease region identification model configured to identify and mark (e.g., with a mask or the like) the disease region in chest XR images.

Figure 21B:
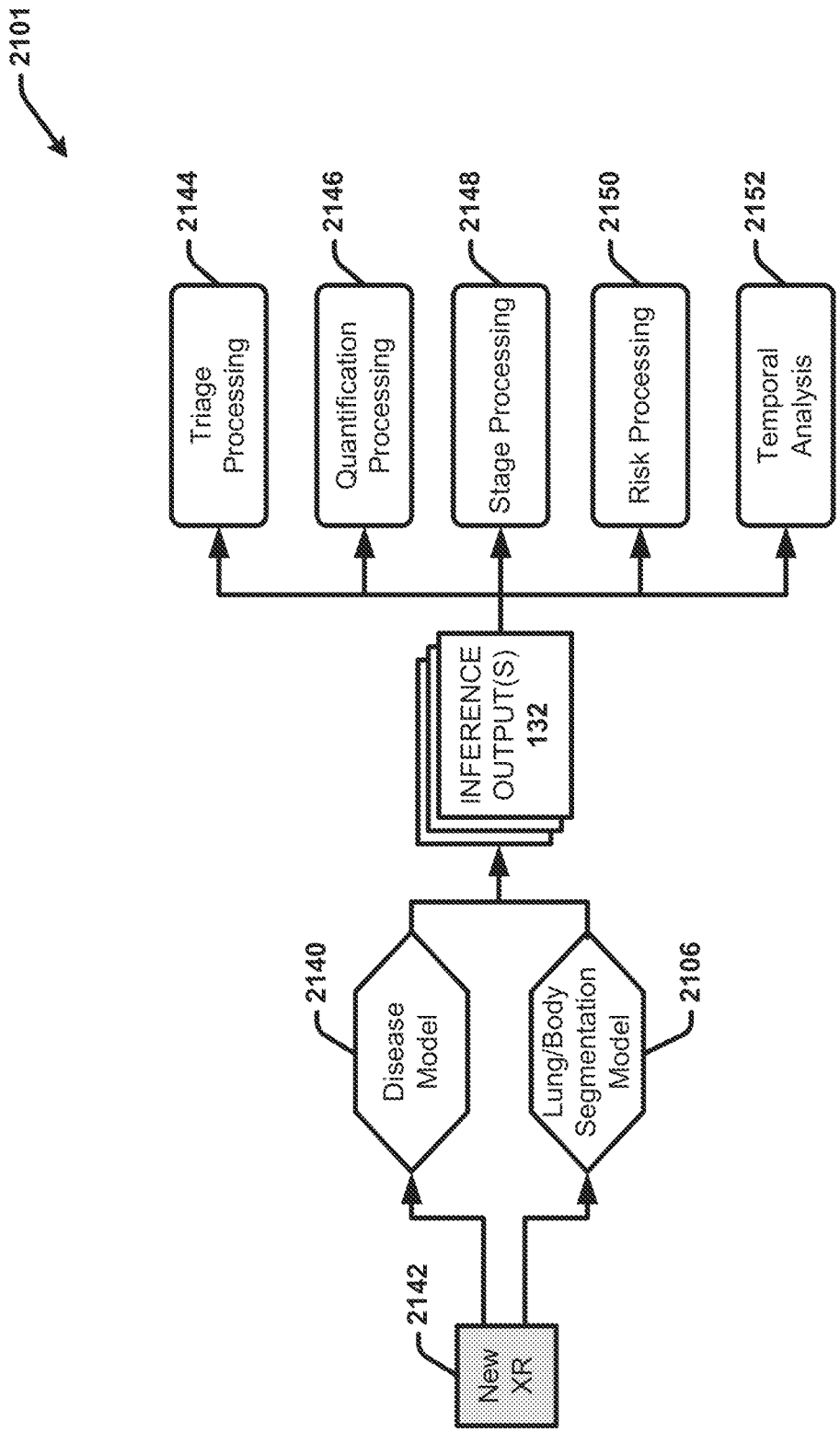
FIG. 21B presents an example inferencing pipeline for medical image processing using mono-modality input images in accordance with one or more embodiments of the disclosed subject matter.

FIG. 21B presents an example inferencing pipeline 2101 for medical image processing using mono-modality input images in accordance with one or more embodiments of the disclosed subject matter. Repetitive description of like elements employed in respective embodiments is omitted for sake of brevity.

Inferencing pipeline 2101 demonstrates an example application of the disease model 2140 once trained using the image data included in the training dataset 2136 to process XR images. In this example application, the disease model 2140 can be applied to a new XR image 2412 to perform an inferencing task related to a medical condition that may or may not be present in the image data, resulting in the generation of one or more inference outputs 132. For example, in implementations in which the disease model 2140 comprises a classification model, the disease model 2140 can classify or diagnose presence or absence of the medical condition in the XR image 2142. With this example, the one or more inference outputs 132 can include a diagnosis (e.g., either disease present or disease absent). In another example implementation, the disease model 2140 can be configured to automatically identify and mark the disease region in the XR image 2140, if detected. With this example, the one or more inference outputs 132 can include a marked-up version of the XR image identifying the disease region, information describing the geometry and position of the disease region, and the like. The lung/body segmentation model 2106 can also be applied to the XR image 2142 to segment the lungs and body. In various embodiments, the inference outputs 132 of these respective models can further be employed for various purposes, including triage processing 2144, quantification processing 2146, stage processing 2148, risk processing 2150, temporal analysis 2152, and the like.

Figure 22A:
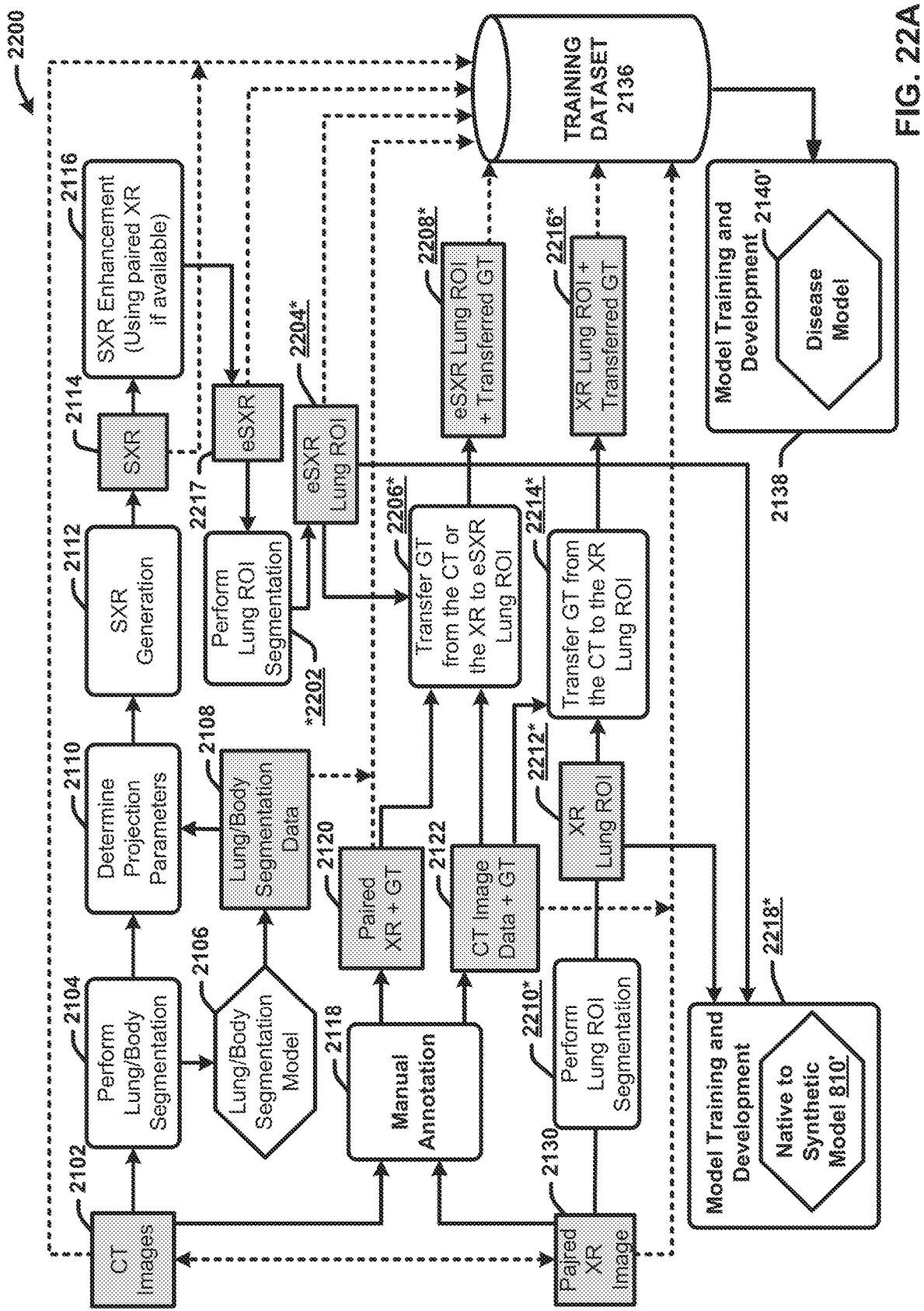
FIG. 22A presents another example multimodal framework for medical image model training and deployment using multimodal input images in accordance with one or more embodiments of the disclosed subject matter.

FIG. 22A presents another example multimodal framework 2200 for medical image model training and deployment using multimodal input images in accordance with one or more embodiments of the disclosed subject matter. Multimodal framework 2200 is similar to multimodal framework 2100 with some differenced noted with new reference numerals that are underlined and stared for ease of identification. Repetitive description of like elements employed in respective embodiments is omitted for sake of brevity.

In accordance with multimodal framework 2200, at 2202, the eSXR image 2217 can be processed using lung ROI segmentation to extract the specific RIO from the sXR image data, which in this example use case in the lungs. In this regard, the resulting eSXR lung ROI image 2204 can isolate the lung image data from other parts of the body present in the eSXR image 2217. At 2206, GT data can be transferred to the eSXR lung ROI image 2204 (e.g., via the annotation transfer component 114). In the embodiment shown, this can include transferring GT data from the CT image data to the eSXR lung ROI image 2204 or GT data from the paired XR image 2130 to the eSXR lung ROI image 2204. The type of the GT information transferred can vary. For example, in some embodiments, the GT data can include mark-up image data applied to the CT image data and transferred to the eSXR lung ROI image 2204 using the same projection parameters used to generate the eSXR image 2117. For instance, the mark-up image data can include masks or boundary marks identifying specific disease regions, specific organs of interest, measurement data, or the like. The GT data can also include metadata associated with the CT image that describes a radiologist's interpretation of various relevant attributes or features in the image data for training a medical image inferencing model to automatically identify or determine. For example, in various embodiments, the GT metadata can include classification information that classifies a disease in the image data as being present or absent, a valuation of the severity of the disease, or the like.

In accordance with multimodal framework 2200, this GT data can also be manually applied at 2118. In this regard, in some embodiments, at 2118, the one or more CT images 2102 (e.g., the CT volume image and/or a representative 2D CT scan slice) can be manually annotated with GT data (e.g., as facilitated by the annotation component 106). The resulting CT image data with the ground truth data applied thereto is represented in FIG. 22A as CT image data+GT 2122. With these embodiments, at 2124, the CT image data+GT 2122 can be transferred to the eSXR lung ROI image 2204 to generate an annotated eSXR lung ROI image with the GT data applied thereto, represented in FIG. 22A as eSXR lung ROI+transferred GT 2208. In other embodiments, at 2118, the paired XR image 2130 can be manually annotated with GT data (e.g., as facilitated by the annotation component 106). The resulting native XR image with the ground truth data applied thereto is represented in FIG. 22A as paired XR+GT 2120. With these embodiments, at 2206, the paired XR+GT 2120 can be transferred to the eSXR lung ROI image 2204 to generate the annotated eSXR lung ROI image with the GT data applied thereto, that is, eSXR lung ROI+transferred GT 2108.

In the embodiment shown, unlike multimodal frame 2100, manual review and revision of the transferred annotation to the eSXR lung ROI image is not performed because the difference in capture time between the CT images 2102 and the paired XR image 2130 (e.g., as determined based on timestamp data associated with the respective images) is less than a defined timeframe (e.g., less than 24 hours).

Also different from multimodal framework 2100, at 2210, lung ROI segmentation can also be performed on the paired XR image 2130, resulting in an XR lung ROI image 2212. In some embodiments (e.g., in which the paired XR image is not manually annotated), at 2214, the CT image data+GT 2122 can be transferred to the XR lung ROI image 2212 to generate an annotated XR lung ROI image with the GT data applied thereto, represented in FIG. 22B as XR lung ROI+transferred GT 2216. Manual review of the XR lung ROI+transferred GT 2216 is again not performed because the difference in capture time between the CT images 2102 and the paired XR image 2130 (e.g., as determined based on timestamp data associated with the respective images) is less than the defined timeframe (e.g., less than 24 hours).

Similar to multimodal framework 2100, with multimodal framework 2200, all of the image data represented in grey boxes can be added to a training dataset 2136. At 2138, the training data included in the training dataset 2136 can further be used to train and develop the disease model 2140' (or another medical image inferencing model). The type of the disease model can vary. For example, in some implementations, the disease model 2140' can include a model configured to classify presence or absence of a medical condition (e.g., pneumonia) in an input medical image. In other implementations, the disease model 2140' can include a model configured segment or mark a disease region depicted in an input image. In various embodiments, the disease model 2140' can be trained to process XR image data as opposed to CT image data, demonstrating how multimodal framework 2100 can employ multimodality image data (e.g., 2D and 3D image data) to generate mono-modality training data (e.g., 2D) that can be used to train and develop a mono-modality inferencing model (e.g., 2D). In the embodiment shown, the asterisk is used for the disease model reference numeral 2140' to indicate that the model is undergoing training and development. In various implementations, the disease model 2140' can be or include a disease region identification model configured to identify and mark (e.g., with a mask or the like) the disease region in chest XR images.

At 2218, multimodal framework 2200 further employs the XR lung ROI 2212 and the eSXR lung ROI 2204 to train and develop the native to synthetic model 810'. In this regard, the native to synthetic model 810' can be trained to transform or adapt a native XR lung ROI image to appear more similar to the eSXR lung ROI image 2204. In the embodiment shown, the asterisk is used for the native to synthetic model 810' to indicate that the model is undergoing training and development.

Figure 22B:
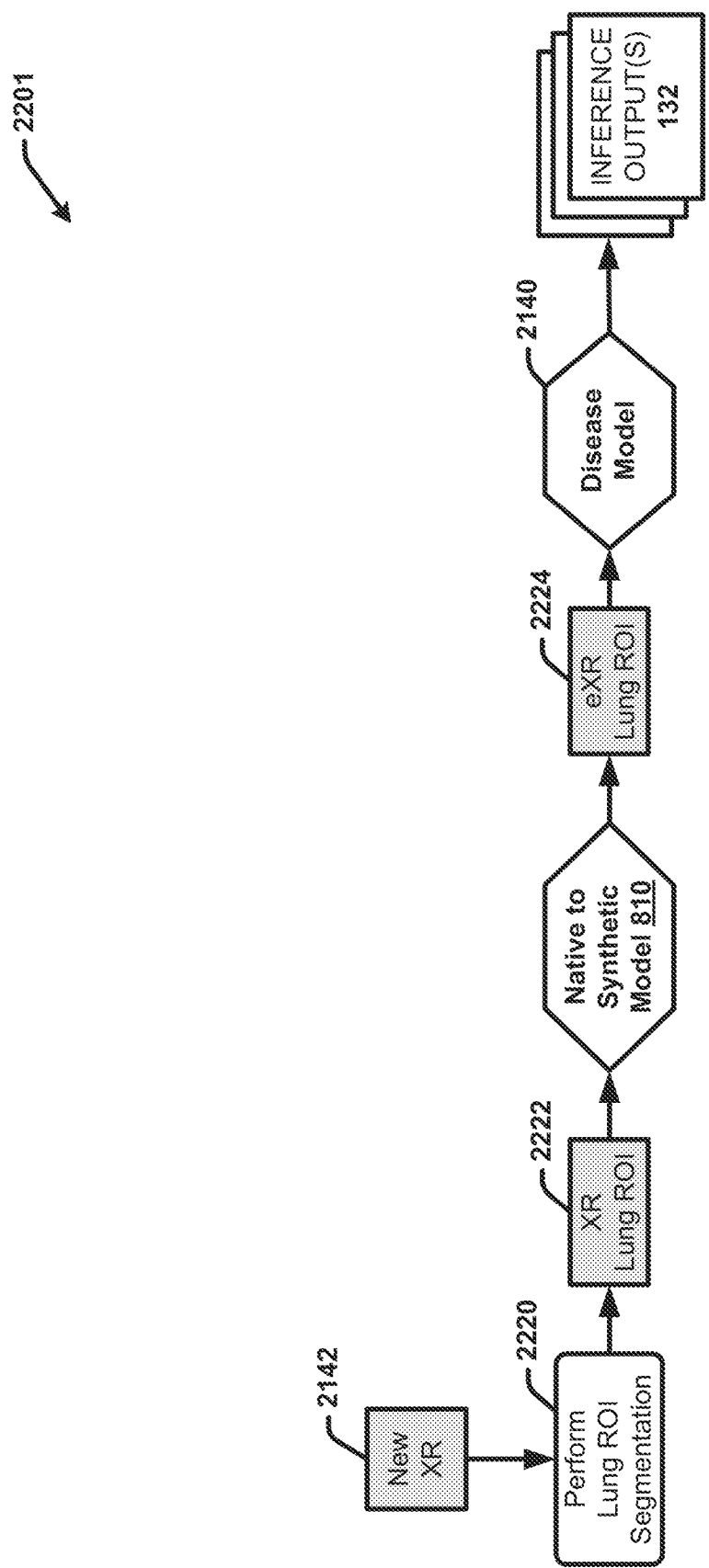
FIG. 22B presents another example inferencing pipeline for medical image processing using mono-modality input images in accordance with one or more embodiments of the disclosed subject matter.

FIG. 22B presents another example inferencing pipeline 2201 for medical image processing using mono-modality input images in accordance with one or more embodiments of the disclosed subject matter. Repetitive description of like elements employed in respective embodiments is omitted for sake of brevity.

Inferencing pipeline 2201 demonstrates another example application of the disease model 2140 once trained using the image data included in the training dataset 2136 to process XR images. In accordance with inferencing pipeline 2201, at 2220, lung ROI segmentation can be performed on the new XR image 2142 to generate a lung ROI image 2222. The now trained native to synthetic model 810 can further be applied to the XR lung ROI image 2222 to generate an enhanced XR (eXR) lung ROI image that has an appearance that is more similar to that of the eSXR lung ROI image 2204. The eXR lung ROI image 2224 can further be processed by the disease model 2140 to generate the one or more inference outputs 132.

In this example application, the disease model 2140 can also be applied to the eXR lung ROI image 2224 to perform an inferencing task related to a medical condition that may or may not be present in the image data, resulting in the generation of one or more inference outputs 132. For example, in implementations in which the disease model 2140 comprises a classification model, the disease model 2140 can classify or diagnose presence or absence of the medical condition in the eXR lung ROI image 2224. With this example, the one or more inference outputs 132 can include a diagnosis (e.g., either disease present or disease absent). In another example implementation, the disease model 2140 can be configured to automatically identify and mark the disease region in the eXR lung ROI image 2224, if detected. With this example, the one or more inference outputs 132 can include a marked-up version of the XR image identifying the disease region, information describing the geometry and position of the disease region, and the like.

Figure 23:
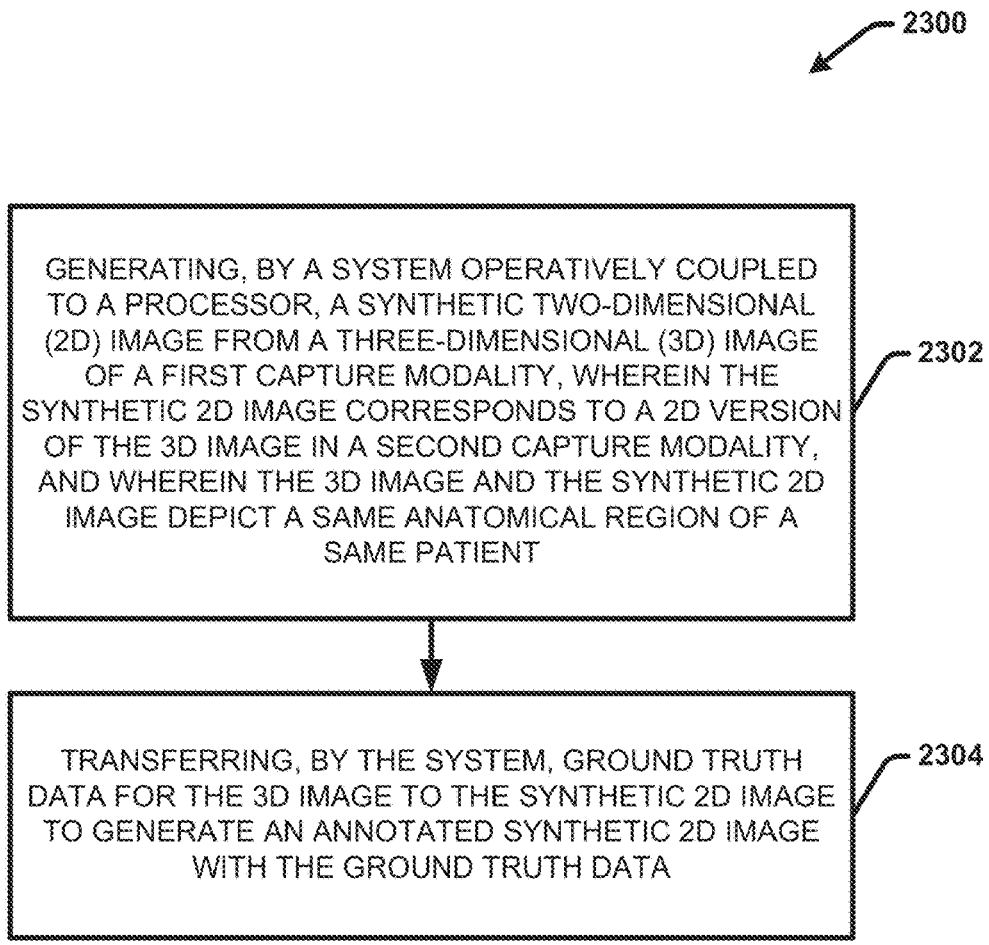
FIG. 23 presents a high-level flow diagram of an example computer-implemented process for generating annotated synthetic 2D images from corresponding 3D image data in accordance with one or more embodiments of the disclosed subject matter.

FIG. 23 presents a high-level flow diagram of an example computer-implemented process 2300 for generating annotated synthetic 2D images from corresponding 3D image data in accordance with one or more embodiments of the disclosed subject matter.

At 2302, a system operatively coupled to a processor (e.g., system 100 and multimodal training data generation module 101, multimodal training data generation module 600, multimodal training data generation module 800, multimodal training data generation module 1600, or like) generates (e.g., using transformation component 202) a synthetic 2D image (e.g., a synthetic 2D image 116) from a 3D image (e.g., a 3D volume and/or image included in the native 3D image data 102) of a first capture modality (e.g., a CT modality), wherein the synthetic 2D image corresponds to a 2D version of the 3D image in a second capture modality (e.g., a XR modality), and wherein the 3D image and the synthetic 2D image depict a same anatomical region of a same patient. At 2304, the system transfers (e.g., using annotation transfer component 114) ground truth data for the 3D image (e.g., included in annotated native 3D images 110) to the synthetic 2D image to generate an annotated synthetic 2D image with the ground truth data (e.g., an annotated synthetic 2D image 118).

Figure 24:
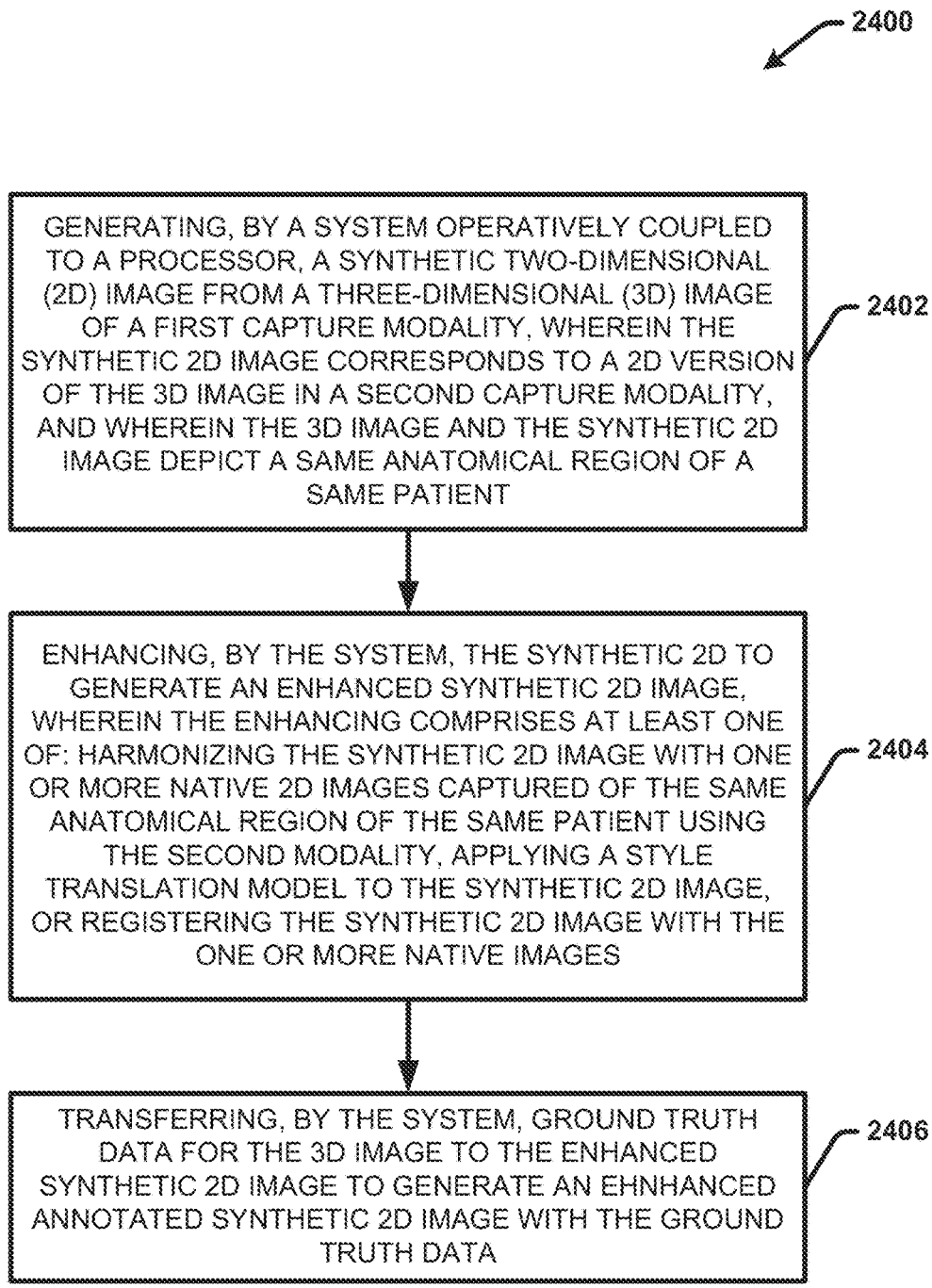
FIG. 24 presents a high-level flow diagram of an example computer-implemented process for generating enhanced annotated synthetic 2D images from corresponding 3D image data in accordance with one or more embodiments of the disclosed subject matter.

FIG. 24 presents a high-level flow diagram of an example computer-implemented process 2400 for generating enhanced annotated synthetic 2D images from corresponding 3D image data in accordance with one or more embodiments of the disclosed subject matter.

At 2402, a system operatively coupled to a processor (e.g., system 100 and multimodal training data generation module 101, multimodal training data generation module 600, multimodal training data generation module 800, multimodal training data generation module 1600, or like) generates (e.g., using transformation component 202) a synthetic 2D image (e.g., a synthetic 2D image 116) from a 3D image (e.g., a 3D volume and/or image included in the native 3D image data 102) of a first capture modality (e.g., a CT modality), wherein the synthetic 2D image corresponds to a 2D version of the 3D image in a second capture modality (e.g., a XR modality), and wherein the 3D image and the synthetic 2D image depict a same anatomical region of a same patient.

At 2404, the system enhances the synthetic 2D (e.g., using enhancement component 802) to generate an enhanced synthetic 2D image (e.g., an enhanced synthetic 2D image 816), wherein the enhancing comprises at least one of: harmonizing (e.g., using harmonization component 804) the synthetic 2D image with one or more native 2D images captured of the same anatomical region of the same patient using the second capture modality, applying a style translation model to the synthetic 2D image (e.g., using style translation component 806), or registering the synthetic 2D image with the one or more native images (e.g., using registration component 812).

At 2406, the system transfers (e.g., using annotation transfer component 114) ground truth data for the 3D image (e.g., included in annotated native 3D images 110) to the enhanced synthetic 2D image to generate an annotated synthetic 2D image with the ground truth data (e.g., an enhanced annotated synthetic 2D image 818).

Figure 25:
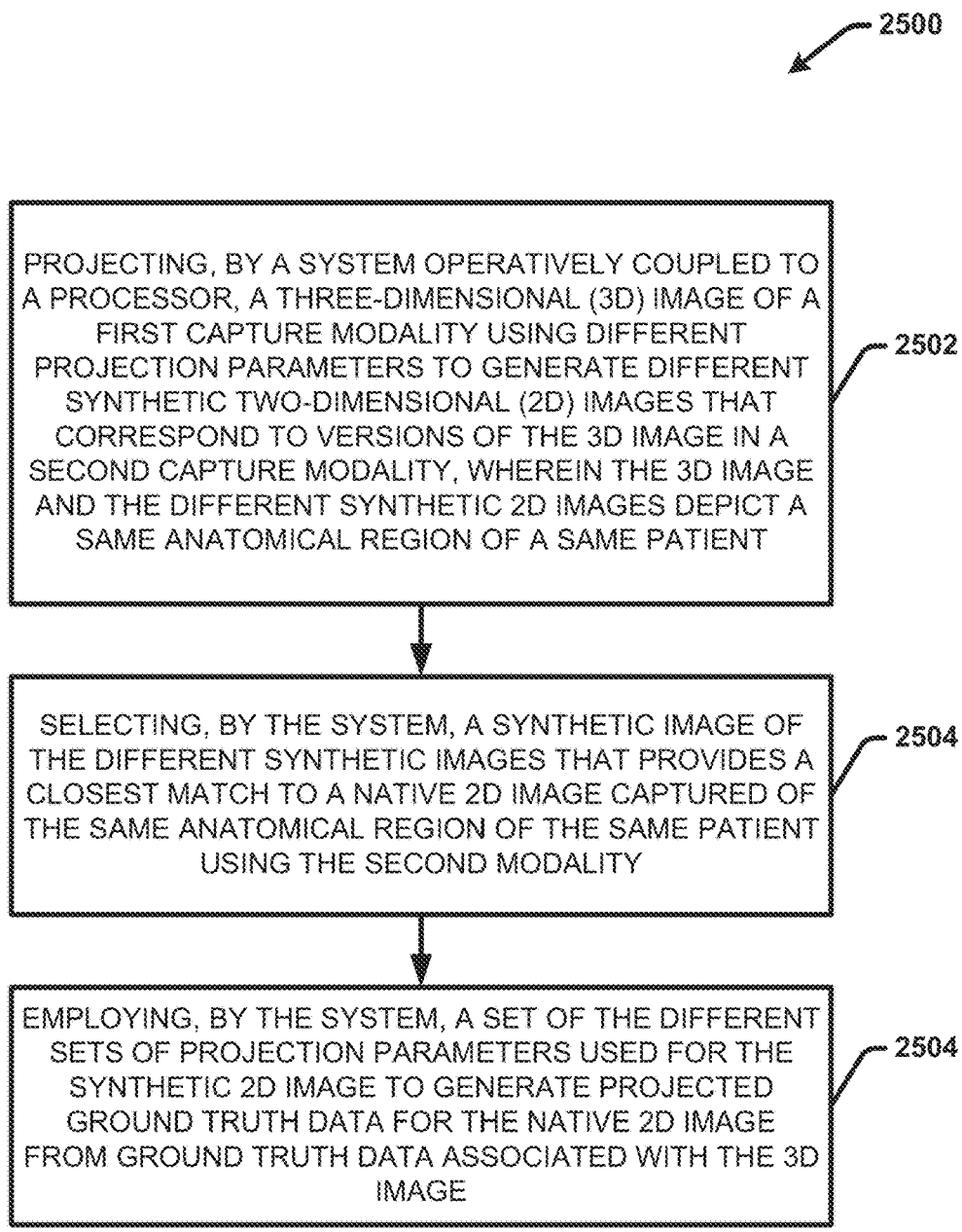
FIG. 25 presents a high-level flow diagram of an example computer-implemented process for generating annotated native 2D images from corresponding 3D image data in accordance with one or more embodiments of the disclosed subject matter.

FIG. 25 presents a high-level flow diagram of an example computer-implemented process 2500 for generating annotated native 2D images from corresponding 3D image data in accordance with one or more embodiments of the disclosed subject matter.

At 2502, a system operatively coupled to a processor (e.g., system 100 and multimodal training data generation module 101, multimodal training data generation module 600, multimodal training data generation module 800, multimodal training data generation module 1600, or like) projects (e.g., using projection component 206) a 3D image of a first capture modality (e.g., a 3D volume image included in the native 3D image data 102) using different projection parameters to generate different synthetic 2D images that correspond to versions of the 3D image in a second modality, wherein the 3D image and the different synthetic 2D image depict a same anatomical region of a same patient. At 2504, the system selects (e.g., using selection component 1602) a synthetic image of the different synthetic images that provides a closest match to a native 2D image captured of the same anatomical region of the same patient using the second modality. At 2506, the system employs a set of the different sets of projection parameters used for the synthetic 2D image to generate projected ground truth data for the native 2D image from ground truth data associated with the 3D image (e.g., using projection component 206). In various embodiments, the annotation transfer component 114 can further transfer the projected ground truth data to the native 2D image to generate the annotated native 2D image.

Example Operating Environment

One or more embodiments can be a system, a method, and/or a computer program product at any possible technical detail level of integration. The computer program product can include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium can be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punchcards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network can comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention can be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions can execute entirely on the user's computer, partly on the user's computer, as a stand-alone software package, partly on the user's computer and partly on a remote computer or entirely on the remote computer or server. In the latter scenario, the remote computer can be connected to the user's computer through any type of network, including a local area network (LAN) or a wide area network (WAN), or the connection can be made to an external computer (for example, through the Internet using an Internet Service Provider). In some embodiments, electronic circuitry including, for example, programmable logic circuitry, field-programmable gate arrays (FPGA), or programmable logic arrays (PLA) can execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It can be understood that each block of the flowchart illustrations and/or block diagrams, and combinations of blocks in the flowchart illustrations and/or block diagrams, can be implemented by computer readable program instructions.

These computer readable program instructions can be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions can also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions can also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams can represent a module, segment, or portion of instructions, which comprises one or more executable instructions for implementing the specified logical function(s). In some alternative implementations, the functions noted in the blocks can occur out of the order noted in the Figures. For example, two blocks shown in succession may, in fact, be executed substantially concurrently, or the blocks can sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

In connection with FIG. 26, the systems and processes described below can be embodied within hardware, such as a single integrated circuit (IC) chip, multiple ICs, an application specific integrated circuit (ASIC), or the like. Further, the order in which some or all of the process blocks appear in each process should not be deemed limiting. Rather, it should be understood that some of the process blocks can be executed in a variety of orders, not all of which can be explicitly illustrated herein.

Figure 26:
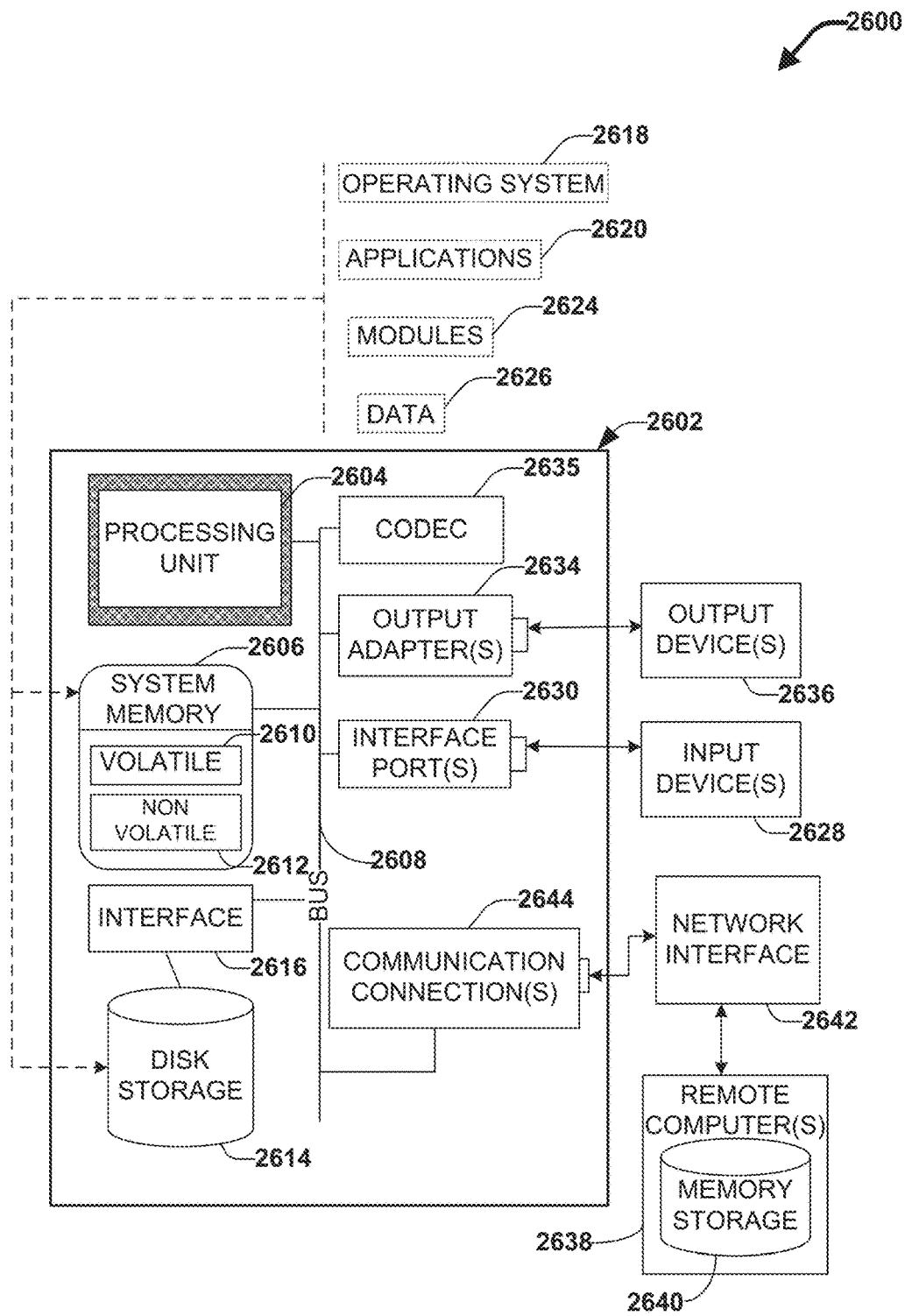
FIG. 26 illustrates a block diagram of an example, non-limiting operating environment in which one or more embodiments described herein can be facilitated.

With reference to FIG. 26, an example environment 2600 for implementing various aspects of the claimed subject matter includes a computer 2602. The computer 2602 includes a processing unit 2604, a system memory 2606, a codec 2635, and a system bus 2608. The system bus 2608 couples system components including, but not limited to, the system memory 2606 to the processing unit 2604. The processing unit 2604 can be any of various available processors. Dual microprocessors and other multiprocessor architectures also can be employed as the processing unit 2604.

The system bus 2608 can be any of several types of bus structure(s) including the memory bus or memory controller, a peripheral bus or external bus, or a local bus using any variety of available bus architectures including, but not limited to, Industrial Standard Architecture (ISA), Micro-Channel Architecture (MSA), Extended ISA (EISA), Intelligent Drive Electronics (IDE), VESA Local Bus (VLB), Peripheral Component Interconnect (PCI), Card Bus, Universal Serial Bus (USB), Advanced Graphics Port (AGP), Personal Computer Memory Card International Association bus (PCMCIA), Firewire (IEEE 1394), and Small Computer Systems Interface (SCSI).

The system memory 2606 includes volatile memory 2610 and non-volatile memory 2612, which can employ one or more of the disclosed memory architectures, in various embodiments. The basic input/output system (BIOS), containing the basic routines to transfer information between elements within the computer 2602, such as during start-up, is stored in non-volatile memory 2612. In addition, according to present innovations, codec 2635 can include at least one of an encoder or decoder, wherein the at least one of an encoder or decoder can consist of hardware, software, or a combination of hardware and software. Although, codec 2635 is depicted as a separate component, codec 2635 can be contained within non-volatile memory 2612. By way of illustration, and not limitation, non-volatile memory 2612 can include read only memory (ROM), programmable ROM (PROM), electrically programmable ROM (EPROM), electrically erasable programmable ROM (EEPROM), Flash memory, 3D Flash memory, or resistive memory such as resistive random access memory (RRAM). Non-volatile memory 2612 can employ one or more of the disclosed memory devices, in at least some embodiments. Moreover, non-volatile memory 2612 can be computer memory (e.g., physically integrated with computer 2602 or a mainboard thereof), or removable memory. Examples of suitable removable memory with which disclosed embodiments can be implemented can include a secure digital (SD) card, a compact Flash (CF) card, a universal serial bus (USB) memory stick, or the like. Volatile memory 2610 includes random access memory (RAM), which acts as external cache memory, and can also employ one or more disclosed memory devices in various embodiments. By way of illustration and not limitation, RAM is available in many forms such as static RAM (SRAM), dynamic RAM (DRAM), synchronous DRAM (SDRAM), double data rate SDRAM (DDR SDRAM), and enhanced SDRAM (ESDRAM) and so forth.

Computer 2602 can also include removable/non-removable, volatile/non-volatile computer storage medium. FIG. 26 illustrates, for example, disk storage 2614. Disk storage 2614 includes, but is not limited to, devices like a magnetic disk drive, solid state disk (SSD), flash memory card, or memory stick. In addition, disk storage 2614 can include storage medium separately or in combination with other storage medium including, but not limited to, an optical disk drive such as a compact disk ROM device (CD-ROM), CD recordable drive (CD-R Drive), CD rewritable drive (CD-RW Drive) or a digital versatile disk ROM drive (DVD-ROM). To facilitate connection of the disk storage 2614 to the system bus 2608, a removable or non-removable interface is typically used, such as interface 2616. It is appreciated that disk storage 2614 can store information related to a user. Such information might be stored at or provided to a server or to an application running on a user device. In one embodiment, the user can be notified (e.g., by way of output device(s) 2636) of the types of information that are stored to disk storage 2614 or transmitted to the server or application. The user can be provided the opportunity to opt-in or opt-out of having such information collected or shared with the server or application (e.g., by way of input from input device(s) 2628).

It is to be appreciated that FIG. 26 describes software that acts as an intermediary between users and the basic computer resources described in the suitable operating environment 2600. Such software includes an operating system 2618. Operating system 2618, which can be stored on disk storage 2614, acts to control and allocate resources of the computer 2602. Applications 2620 take advantage of the management of resources by operating system 2618 through program modules 2624, and program data 2626, such as the boot/shutdown transaction table and the like, stored either in system memory 2606 or on disk storage 2614. It is to be appreciated that the claimed subject matter can be implemented with various operating systems or combinations of operating systems.

A user enters commands or information into the computer 2602 through input device(s) 2628. Input devices 2628 include, but are not limited to, a pointing device such as a mouse, trackball, stylus, touch pad, keyboard, microphone, joystick, game pad, satellite dish, scanner, TV tuner card, digital camera, digital video camera, web camera, and the like. These and other input devices connect to the processing unit 2604 through the system bus 2608 via interface port(s) 2630. Interface port(s) 2630 include, for example, a serial port, a parallel port, a game port, and a universal serial bus (USB). Output device(s) 2636 use some of the same type of ports as input device(s) 2628. Thus, for example, a USB port can be used to provide input to computer 2602 and to output information from computer 2602 to an output device 2636. Output adapter 2634 is provided to illustrate that there are some output devices 2636 like monitors, speakers, and printers, among other output devices 2636, which require special adapters. The output adapters 2634 include, by way of illustration and not limitation, video and sound cards that provide a means of connection between the output device 2636 and the system bus 2608. It should be noted that other devices or systems of devices provide both input and output capabilities such as remote computer(s) 2638.

Computer 2602 can operate in a networked environment using logical connections to one or more remote computers, such as remote computer(s) 2638. The remote computer(s) 2638 can be a personal computer, a server, a router, a network PC, a workstation, a microprocessor based appliance, a peer device, a smart phone, a tablet, or other network node, and typically includes many of the elements described relative to computer 2602. For purposes of brevity, only a memory storage device 2640 is illustrated with remote computer(s) 2638. Remote computer(s) 2638 is logically connected to computer 2602 through a network interface 2642 and then connected via communication connection(s) 2644. Network interface 2642 encompasses wire or wireless communication networks such as local-area networks (LAN) and wide-area networks (WAN) and cellular networks. LAN technologies include Fiber Distributed Data Interface (FDDI), Copper Distributed Data Interface (CDDI), Ethernet, Token Ring and the like. WAN technologies include, but are not limited to, point-to-point links, circuit switching networks like Integrated Services Digital Networks (ISDN) and variations thereon, packet switching networks, and Digital Subscriber Lines (DSL).

Communication connection(s) 2644 refers to the hardware/software employed to connect the network interface 2642 to the bus 2608. While communication connection 2644 is shown for illustrative clarity inside computer 2602, it can also be external to computer 2602. The hardware/software necessary for connection to the network interface 2642 includes, for exemplary purposes only, internal and external technologies such as, modems including regular telephone grade modems, cable modems and DSL modems, ISDN adapters, and wired and wireless Ethernet cards, hubs, and routers.

While the subject matter has been described above in the general context of computer-executable instructions of a computer program product that runs on a computer and/or computers, those skilled in the art will recognize that this disclosure also can or can be implemented in combination with other program modules. Generally, program modules include routines, programs, components, data structures, etc. that perform particular tasks and/or implement particular abstract data types. Moreover, those skilled in the art will appreciate that the inventive computer-implemented methods can be practiced with other computer system configurations, including single-processor or multiprocessor computer systems, mini-computing devices, mainframe computers, as well as computers, hand-held computing devices (e.g., PDA, phone), microprocessor-based or programmable consumer or industrial electronics, and the like. The illustrated aspects can also be practiced in distributed computing environments where tasks are performed by remote processing devices that are linked through a communications network. However, some, if not all aspects of this disclosure can be practiced on stand-alone computers. In a distributed computing environment, program modules can be located in both local and remote memory storage devices.

As used in this application, the terms "component," "system," "platform," "interface," and the like, can refer to and/or can include a computer-related entity or an entity related to an operational machine with one or more specific functionalities. The entities disclosed herein can be either hardware, a combination of hardware and software, software, or software in execution. For example, a component can be, but is not limited to being, a process running on a processor, a processor, an object, an executable, a thread of execution, a program, and/or a computer. By way of illustration, both an application running on a server and the server can be a component. One or more components can reside within a process and/or thread of execution and a component can be localized on one computer and/or distributed between two or more computers. In another example, respective components can execute from various computer readable media having various data structures stored thereon. The components can communicate via local and/or remote processes such as in accordance with a signal having one or more data packets (e.g., data from one component interacting with another component in a local system, distributed system, and/or across a network such as the Internet with other systems via the signal). As another example, a component can be an apparatus with specific functionality provided by mechanical parts operated by electric or electronic circuitry, which is operated by a software or firmware application executed by a processor. In such a case, the processor can be internal or external to the apparatus and can execute at least a part of the software or firmware application. As yet another example, a component can be an apparatus that provides specific functionality through electronic components without mechanical parts, wherein the electronic components can include a processor or other means to execute software or firmware that confers at least in part the functionality of the electronic components. In an aspect, a component can emulate an electronic component via a virtual machine, e.g., within a cloud computing system.

In addition, the term "or" is intended to mean an inclusive "or" rather than an exclusive "or." That is, unless specified otherwise, or clear from context, "X employs A or B" is intended to mean any of the natural inclusive permutations. That is, if X employs A; X employs B; or X employs both A and B, then "X employs A or B" is satisfied under any of the foregoing instances. Moreover, articles "a" and "an" as used in the subject specification and annexed drawings should generally be construed to mean "one or more" unless specified otherwise or clear from context to be directed to a singular form. As used herein, the terms "example" and/or "exemplary" are utilized to mean serving as an example, instance, or illustration and are intended to be non-limiting. For the avoidance of doubt, the subject matter disclosed herein is not limited by such examples. In addition, any aspect or design described herein as an "example" and/or "exemplary" is not necessarily to be construed as preferred or advantageous over other aspects or designs, nor is it meant to preclude equivalent exemplary structures and techniques known to those of ordinary skill in the art.

As it is employed in the subject specification, the term "processor" can refer to substantially any computing processing unit or device comprising, but not limited to, single-core processors; single-processors with software multithread execution capability; multi-core processors; multi-core processors with software multithread execution capability; multi-core processors with hardware multithread technology; parallel platforms; and parallel platforms with distributed shared memory. Additionally, a processor can refer to an integrated circuit, an application specific integrated circuit (ASIC), a digital signal processor (DSP), a field programmable gate array (FPGA), a programmable logic controller (PLC), a complex programmable logic device (CPLD), a discrete gate or transistor logic, discrete hardware components, or any combination thereof designed to perform the functions described herein. Further, processors can exploit nano-scale architectures such as, but not limited to, molecular and quantum-dot based transistors, switches and gates, in order to optimize space usage or enhance performance of user equipment. A processor can also be implemented as a combination of computing processing units. In this disclosure, terms such as "store," "storage," "data store," data storage," "database," and substantially any other information storage component relevant to operation and functionality of a component are utilized to refer to "memory components," entities embodied in a "memory," or components comprising a memory. It is to be appreciated that memory and/or memory components described herein can be either volatile memory or nonvolatile memory, or can include both volatile and nonvolatile memory. By way of illustration, and not limitation, nonvolatile memory can include read only memory (ROM), programmable ROM (PROM), electrically programmable ROM (EPROM), electrically erasable ROM (EEPROM), flash memory, or non-volatile random access memory (RAM) (e.g., ferroelectric RAM (FeRAM). Volatile memory can include RAM, which can act as external cache memory, for example. By way of illustration and not limitation, RAM is available in many forms such as synchronous RAM (SRAM), dynamic RAM (DRAM), synchronous DRAM (SDRAM), double data rate SDRAM (DDR SDRAM), enhanced SDRAM (ESDRAM), Synchlink DRAM (SLDRAM), direct Rambus RAM (DR-RAM), direct Rambus dynamic RAM (DRDRAM), and Rambus dynamic RAM (RDRAM). Additionally, the disclosed memory components of systems or computer-implemented methods herein are intended to include, without being limited to including, these and any other suitable types of memory.

What has been described above include mere examples of systems and computer-implemented methods. It is, of course, not possible to describe every conceivable combination of components or computer-implemented methods for purposes of describing this disclosure, but one of ordinary skill in the art can recognize that many further combinations and permutations of this disclosure are possible. Furthermore, to the extent that the terms "includes," "has," "possesses," and the like are used in the detailed description, claims, appendices and drawings such terms are intended to be inclusive in a manner similar to the term "comprising" as "comprising" is interpreted when employed as a transitional word in a claim. The descriptions of the various embodiments have been presented for purposes of illustration, but are not intended to be exhaustive or limited to the embodiments disclosed. Many modifications and variations can be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A system, comprising:
   a memory that stores computer executable components; and
   a processor that executes the computer executable components stored in the memory, wherein the computer executable components comprise:
      a transformation component that generates a synthetic two-dimensional (2D) image from a three-dimensional (3D) image of a first capture modality, wherein the synthetic 2D image corresponds to a 2D version of the 3D image in a second capture modality, and wherein the 3D image and the synthetic 2D image depict a same anatomical region of a same patient;
      a projection component that projects the 3D image using different projection parameters to generate different synthetic 2D images respectively corresponding to 2D versions of the 3D image in the second capture modality, the different synthetic 2D images including the synthetic 2D image;
      a selection component that selects the synthetic 2D image from amongst the different synthetic 2D images based on a determination that, relative to other synthetic 2D images of the different synthetic 2D images, the synthetic 2D provides a closest match to a native 2D image captured of the same anatomical region of the same patient using the second capture modality; and
      an annotation transfer component that transfers ground truth data for the 3D image to the synthetic 2D image to generate an annotated synthetic 2D image with the ground truth data.

2. The system of claim 1, wherein the computer executable components further comprise:
   a training module that employs the synthetic 2D image and the annotated synthetic 2D image to train one or more machine learning models to perform a medical inferencing task related to a medical condition reflected in the same anatomical region.

3. The system of claim 2, wherein the one or more machine learning models comprise at least one model configured to perform the medical inferencing task on 2D input images as input as opposed to 3D input images.

4. The system of claim 3, wherein the computer executable components can further comprise:
   an inferencing module that applies at least one machine learning model to the 2D images to generate inference outputs.

5. The system of claim 4, wherein the 2D input images are selected from a group consisting of: native 2D images, synthetic 2D images and enhanced synthetic 2D images.

6. The system of claim 1, wherein the transformation component employs 3D to 2D transformation model to generate the synthetic 2D image from the 3D image.

7. The system of claim 1, wherein the transformation component generates the synthetic 2D image using a projection process selected from a group consisting of: parallel projection of the 3D image or point source projection of the 3D image with optimal projection parameters, and wherein the projection process involves removing one or more objects from the 3D image that are excluded from 2D images captured using the second capture modality.

8. The system of claim 7, wherein the 3D image comprises a 3D volume image, and wherein the computer executable components further comprise:
   a pre-projection processing component that determines the optimal projection parameters for the point source projection process based on segmentation of one or more 3D objects taken from the 3D volume image, and wherein the transformation component performs the projection process using the optimal projection parameters.

9. The system of claim 8, wherein the ground truth data comprises projected ground truth data, and wherein the projection component generates the projected ground truth data based on projection of the ground truth data using the projection process and the optimal projection parameters.

10. The system of claim 1, wherein the annotation transfer component further transfers the ground truth data for the 3D image to the different synthetic 2D images using corresponding projection parameters of the different synthetic 2D images to generate ground truth data for the different synthetic 2D images, and wherein the computer executable components further comprise:
  a training module that employs the different synthetic 2D images and the ground truth data for the synthetic 2D images to train one or more machine learning models to perform a medical inferencing task related to a medical condition reflected in the same anatomical region.

11. The system of claim 1, wherein the selection component determines that the synthetic 2D image provides the closest match based on comparison of the native 2D image to the different synthetic 2D images using one or more similarity evaluation metrics.

12. The system of claim 11, wherein the computer executable components further comprise:
  a registration component that registers the different synthetic 2D images with the native 2D image prior to the comparison.

13. The system of claim 12, wherein the registration results in transformation of the synthetic 2D image into a registered synthetic 2D image, and wherein the annotation transfer component further transfers the ground truth data to the registered synthetic 2D image using a subset of the different projection parameters used to generate the synthetic 2D image, resulting in generation of an annotated registered synthetic 2D image.

14. The system of claim 1, wherein based on selection of the synthetic 2D image, the annotation transfer component further transfers the ground truth data to the native 2D image using a subset of the different projection parameters used for the synthetic 2D image.

15. A method comprising:
  generating, by a system operatively coupled to a processor, a synthetic two-dimensional (2D) image from a three-dimensional (3D) image of a first capture modality, wherein the synthetic 2D image corresponds to a 2D version of the 3D image in a second capture modality, and wherein the 3D image and the synthetic 2D image depict a same anatomical region of a same patient;
  projecting, by the system, the 3D image using different projection parameters to generate different synthetic 2D images respectively corresponding to versions of the 3D image in the second capture modality, the different synthetic 2D images including the synthetic 2D image;
  selecting, by the system, the synthetic 2D image from amongst the different synthetic 2D images based on a determination that, relative to other synthetic 2D images of the different synthetic 2D images, the synthetic 2D provides a closest match to a native 2D image captured of the same anatomical region of the same patient using the second capture modality; and
  transferring, by the system, ground truth data for the 3D image to the synthetic 2D image to generate an annotated synthetic 2D image with the ground truth data.

16. The method of claim 15, further comprising:
  employing, by the system, the synthetic 2D image and the annotated synthetic 2D image to train one or more machine learning models to perform a medical inferencing task related to a medical condition reflected in the same anatomical region.

17. The method of claim 16, wherein the one or more machine learning models comprise at least one model configured to perform the medical inferencing task on 2D input images as input as opposed to 3D input images.

18. The method of claim 17, further comprising:
  applying, by the system, the at least one machine learning model to the 2D images to generate inference outputs.

19. The method of claim 18, wherein the 2D input images are selected from a group consisting of: native 2D images, synthetic 2D images, and enhanced synthetic 2D images.

20. The method of claim 15, wherein the 3D image comprises a 3D volume image and wherein generating the synthetic 2D image comprises using a projection process selected from a group consisting of: parallel projection of the 3D volume image and point source projection of the 3D volume image.

21. The method of claim 15, wherein the 3D image comprises a 3D volume image and wherein generating the synthetic 2D image comprises using point source projection of the 3D volume image, and wherein the method further comprises:
  determining, by the system, optimal projection parameters for the projection process based on segmentation of a 3D object from the 3D volume image; and
  performing, by the system, the point source projection using the optimal projection parameters.

22. The method of claim 21, wherein the ground truth data comprises projected ground truth data, and wherein the method further comprises:
  generating, by the system, the projected ground truth data based on projection of the ground truth data using the projection process and the optimal projection parameters.

23. The method of claim 15, further comprising:
  based on selection of the synthetic 2D image, transferring, by the system, the ground truth data to the native 2D image using a subset of the different projection parameters used for the synthetic 2D image.

24. A non-transitory machine-readable storage medium, comprising executable instructions that, when executed by a processor, facilitate performance of operations, comprising:
  generating a synthetic two-dimensional (2D) image from a three-dimensional (3D) image of a first capture modality, wherein the synthetic 2D image corresponds to a 2D version of the 3D image in a second capture modality, and wherein the 3D image and the synthetic 2D image depict a same anatomical region of a same patient;
  projecting the 3D image using different projection parameters to generate different synthetic 2D images respectively corresponding to versions of the 3D image in the second capture modality, the different synthetic 2D images including the synthetic 2D image;
  selecting the synthetic 2D image from amongst the different synthetic 2D images based on a determination that, relative to other synthetic 2D images of the different synthetic 2D images, the synthetic 2D provides a closest match to a native 2D image captured of the same anatomical region of the same patient using the second capture modality; and
  transferring ground truth data for the 3D image to the synthetic 2D image to generate an annotated synthetic 2D image with the ground truth data.

25. The non-transitory machine-readable storage medium of claim 24, wherein the operations further comprise:
  employing the synthetic 2D image and the annotated synthetic 2D image to train one or more machine learning models to perform a medical inferencing task related to a medical condition reflected in the same anatomical region.

26. The non-transitory machine-readable storage medium of claim 25, wherein the one or more machine learning models comprise at least one model configured to perform the medical inferencing task on 2D input images as input as opposed to 3D input images.

27. The non-transitory machine-readable storage medium of claim 26, wherein the operations further comprise:
applying the at least one machine learning model to the 2D images to generate inference outputs.

28. The non-transitory machine-readable storage medium of claim 24, wherein the 2D input images are selected from a group consisting of: native 2D images, synthetic 2D images, and enhanced synthetic 2D images.

29. The non-transitory machine-readable storage medium of claim 24, wherein the 3D image comprises a 3D volume image and wherein generating the synthetic 2D image comprises using a projection process selected from a group consisting of: parallel projection of the 3D volume image and point source projection of the 3D volume image.

30. The non-transitory machine-readable storage medium of claim 24, wherein the 3D image comprises a 3D volume image and wherein generating the synthetic 2D image comprises using point source projection of the 3D volume image, and wherein the operations further comprise:
determining optimal projection parameters for the projection process based on segmentation of a 3D object from the 3D volume image; and
performing the point source projection using the optimal projection parameters.

31. The non-transitory machine-readable storage medium of claim 24, wherein the operations further comprise:
based on selection of the synthetic 2D image, transferring the ground truth data to the native 2D image using a subset of the different projection parameters used for the synthetic 2D image.

\* \* \* \* \*